US012102671B2

(12) United States Patent
Collins et al.

(10) Patent No.: US 12,102,671 B2
(45) Date of Patent: Oct. 1, 2024

(54) METHOD OF VACCINATION WITH AN ATTENUATED RSV VACCINE FORMULATION

(71) Applicant: The USA, as represented by the Secretary, Department of Health and Human Services, Bethesda, MD (US)

(72) Inventors: Peter L. Collins, Silver Spring, MD (US); Ursula J. Buchholz, Silver Spring, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 100 days.

(21) Appl. No.: 15/773,653

(22) PCT Filed: Nov. 4, 2016

(86) PCT No.: PCT/US2016/060672
§ 371 (c)(1),
(2) Date: May 4, 2018

(87) PCT Pub. No.: WO2017/079651
PCT Pub. Date: May 11, 2017

(65) Prior Publication Data
US 2018/0318411 A1 Nov. 8, 2018

Related U.S. Application Data

(60) Provisional application No. 62/251,030, filed on Nov. 4, 2015, provisional application No. 62/259,472, filed on Nov. 24, 2015, provisional application No. 62/263,405, filed on Dec. 4, 2015.

(51) Int. Cl.
*A61K 39/155* (2006.01)
*A61K 39/12* (2006.01)
*A61K 39/00* (2006.01)

(52) U.S. Cl.
CPC ............ *A61K 39/12* (2013.01); *A61K 39/155* (2013.01); *A61K 2039/5254* (2013.01); *A61K 2039/543* (2013.01); *A61K 2039/545* (2013.01); *A61K 2039/55* (2013.01); *C12N 2760/18523* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | |
|---|---|---|---|
| 6,264,957 B1 | 7/2001 | Collins | |
| 6,713,066 B1 | 3/2004 | Collins et al. | |
| 6,790,449 B2 | 9/2004 | Collins et al. | |
| 6,830,748 B1 | 12/2004 | Jin et al. | |
| 7,205,013 B2 | 4/2007 | Jin et al. | |
| 7,465,574 B2 | 12/2008 | Jin et al. | |
| 7,572,904 B2 | 8/2009 | Cheng et al. | |
| 8,163,530 B2 | 4/2012 | Cheng et al. | |
| 2005/0084947 A1 | 4/2005 | Jin et al. | |
| 2005/0164175 A1 | 7/2005 | Jin et al. | |
| 2008/0279892 A1 | 11/2008 | Jin et al. | |
| 2009/0117150 A1 | 5/2009 | Jin et al. | |
| 2009/0175899 A1 | 7/2009 | Jin et al. | |
| 2009/0274727 A1 | 11/2009 | Jin et al. | |
| 2010/0028377 A1 | 2/2010 | Jin et al. | |
| 2012/0282673 A1 | 11/2012 | Hong et al. | |
| 2012/0308602 A1 | 12/2012 | Jin et al. | |
| 2016/0228536 A1* | 8/2016 | Schickli | A61K 39/12 |

FOREIGN PATENT DOCUMENTS

WO WO 2015/041924 3/2015

OTHER PUBLICATIONS

Anderson et al. Strategic priorities for respiratory syncytial virus (RSV) vaccine development. Vaccine. Apr. 18, 2013;31 Suppl 2: B209-15.*

International Search Report and Written Opinion prepared by the European Patent Office on Jan. 30, 2017, for International Application No. PCT/US2016/060672.
Bermingham et al. "The M2-2 protein of human respiratory syncytial virus is a regulatory factor involved in the balance between RNA replication and transcription," PNAS, Sep. 1999, vol. 96, No. 2, pp. 11259-11264.
Bernstein et al. "Phase 1 study of the safety and immunogenicity of a live, attenuated respiratory syncytial virus and parainfluenza virus type 3 vaccine in seronegative children." The Pediatric Infectious Disease Journal, Feb. 2012, vol. 31, No. 2, pp. 109-114.
Bukreyev et al. "Granulocyte-Macrophage Colony—Stimulating Factor Expressed by Recombinant Respiratory Syncytial Virus Attenuates Viral Replication and Increases the Level of Pulmonary Antigen-Presenting Cells," Journal of Virology, Dec. 2001, vol. 75, No. 24, pp. 12128-12240.

Cheng et al. "Chimeric Subgroup A Respiratory Syncytial Virus with the Glycoproteins Substituted by Those of Subgroup B and RSV without the M2-2 Gene Are Attenuated in African Green Monkeys," Virology, Apr. 2001, vol. 283, No. 1, pp. 59-68.

Collins et al. "Respiratory Syncytial Virus: Reverse Genetics and Vaccine Strategies," Virology, May 2002, vol. 296, No. 2, pp. 204-211.

(Continued)

*Primary Examiner* — Nianxiang Zou

(74) *Attorney, Agent, or Firm* — McBee Moore & Vanik IP, LLC

(57) ABSTRACT

Respiratory syncytial virus (RSV) infection may lead to severe respiratory illness in young children. Thus, there is a need for a live attenuated vaccine, which would mimic the natural course of infection without causing illness; however, restricting viral replication also reduces the immune response. Reported herein is a method of vaccination using a single dose of a recombinant RSV lacking the M2-2 protein that surprisingly induced a stronger immune response to RSV than previous vaccine candidates despite being more restricted in replication.

14 Claims, 15 Drawing Sheets

Specification includes a Sequence Listing.

(56) References Cited

OTHER PUBLICATIONS

Collins et al. "Progress in understanding and controlling respiratory syncytial virus: Still crazy after all these years," Virus Research, Dec. 2011, vol. 162, No. 1-2, pp. 80-99.
Collins et al. "Production of infectious human respiratory syncytial virus from cloned cDNA confirms an essential role for the transcription elongation factor from the 5' proximal open reading frame of the M2 mRNA in gene expression and provides a capability for vaccine development," PNAS, Dec. 1995, vol. 92, No. 25, pp. 11563-11567.
Connors et al. "Cotton rats previously immunized with a chimeric RSV FG glycoprotein develop enhanced pulmonary pathology when infected with RSV, a phenomenon not encountered following immunization with vaccinia-RSV recombinants or RSV," Vaccine, 1992, vol. 10, No. 7, pp. 475-484 (Abstract Only).
Djupesland "Nasal drug delivery devices: characteristics and performance in a clinical perspective—a review," Drug Delivery and Translational Research, Feb. 2013, vol. 3, No. 1, pp. 42-62.
Englund et al. "Safety and Infectivity of Two Doses of Live—Attenuated Recombinant Cold—Passaged Human Parainfluenza Type 3 Virus Vaccine rHPIV3cp45 in HPIV3-Seronegative Young Children," Vaccine, Nov. 2013, vol. 31, No. 48, pp. 5706-5712.
Graham et al. "Challenges and opportunities for respiratory syncytial virus vaccines." Current Topics in Microbiology and Immunology, 2013, vol. 372, pp. 391-404 (Abstract Only).
Groothuis et al. "Prophylactic Administration of Respiratory Syncytial Virus Immune Globulin to High-Risk Infants and Young Children," The New England Journal of Medicine, Nov. 1993, vol. 329, No. 21, pp. 1524-1530.
Hall et al. "The Burden of Respiratory Syncytial Virus Infection in Young Children," The New England Journal of Medicine, Feb. 2009, vol. 360, No. 6, pp. 588-598.
Jin et al. "Recombinant Respiratory Syncytial Viruses with Deletions in the NS1, NS2, Sh, and M2-2 Genes Are Attenuated in Vitro and in Vivo," Virology, Jul. 2000, vol. 273, No. 1, pp. 210-218.
Jin et al. "Respiratory syncytial Virus That Lacks Open Reading Frame 2 of the M2 Gene (M2-2) Has Altered Growth Characteristics and Is Attenuated in Rodents," Journal of Virology, Jan. 2000, vol. 74, No. 1, pp. 74-82.
Karron et al. "Identification of a Recombinant Live Attenuated Respiratory Syncytial Virus Vaccine Candidate That is Highly Attenuated in Infants," Journal of Infectious Diseases, Apr. 2005, vol. 191, pp. 1093-1103.
Karron et al. "Evaluation of Two Live, Cold-Passaged, Temperature-Sensitive Respiratory Syncytial Virus Vaccines in Chimpanzees and in Human Adults, Infants, and Children," The Journal of Infectious Diseases, Dec. 1997, vol. 176, No. 6, pp. 1428-1436.
Karron et al. "Live-Attenuated Respiratory Syncytial Virus Vaccines," Current Topics in Microbiology and Immunology, 2013, vol. 372, pp. 259-284.
Lawlor et al. "A single amino acid in the F2 subunit of respiratory syncytial virus fusion protein alters growth and fusogenicity," Journal of General Virology, 2013, vol. 94, pp. 2627-2635.
Malkin et al. "Safety and Immunogenicity of a Live Attenuated RSV Vaccine in Healthy RSV-Seronegative Children 5 60 24 Months of Age," PLOS One, Oct. 2013, vol. 8, No. 10, e77104, 10 pages.
Murphy et al. "Live-attenuated virus vaccines for respiratory syncytial and parainfluenza viruses: applications of reverse genetics," The Journal of Clinical Investigation, Jul. 2002, vol. 110, No. 1, pp. 21-27.
Murphy et al. "An update on approaches to the development of respiratory syncytial virus (RSV) and parainfluenza virus type 3 (PIV3) vaccines," Virus Research, Apr. 1994, vol. 32, No. 1, pp. 13-36 (Abstract Only).
Murphy et al. "Enhanced pulmonary histopathology is observed in cotton rats immunized with formalin-inactivated respiratory syncytial virus (RSV) or purified F glycoprotein and challenged with RSV 3-6 months after immunization," Vaccine, Oct. 1990, vol. 8, No. 5, pp. 497-502 (Abstract Only).
Nair et al. "Global burden of acute lower respiratory infections due to respiratory syncytial virus in young children: a systematic review and meta-analysis," The Lancet, May 2010, vol. 375, No. 9725, pp. 1545-1555 (Summary only).
Neuzil "Progress toward a Respiratory Syncytial Virus Vaccine," Clinical and Vaccine Immunology, Mar. 2016, vol. 23, No. 3, pp. 186-188.
Shay et al. "Bronchiolitis—Associated Hospitalizations Among US Children, 1980-1996," JAMA Oct. 1999, vol. 282, No. 15, pp. 1440-1446.
Smith et al. "Respiratory Syncytial Virus Fusion Glycoprotein Expressed in Insect Cells Form Protein Nanoparticles That Induce Protective Immunity in Cotton Rats," PLOS One, Nov. 2012, vol. 7, No. 11, e50852, 12 pages.
Teng et al. "Recombinant Respiratory Syncytial Virus That Does Not Express the NS1 or M2-2 Protein is Highly Attenuated and Immunogenic in Chimpanzees," Journal of Virology, Oct. 2000, vol. 74, No. 19, pp. 9317-9321.
Weisshaar et al. "Blocking Respiratory Syncytial Virus Entry: A Story with Twists," DNA and Cell Biology, 2015, vol. 34, No. 8, pp. 505-510.
Wright et al. "Evaluation of a Live, Cold-Passaged, Temperature-Sensitive, Respiratory Syncytial Virus Vaccine Candidate in Infancy," The Journal of Infectious Diseases, Nov. 2008, vol. 182, pp. 1331-1342.
Wright et al. "The Interferon Antagonist NS2 Protein of Respiratory Syncytial Virus is an Important Virulence Determinant for Humans," The Journal of Infectious Diseases, Feb. 2006, vol. 193, No. 4, pp. 573-581.
Wright et al. "The Absence of Enhanced Disease with Wild-Type Respiratory Syncytial Virus Infection Occurring After Receipt of Live, Attenuated, Respiratory Syncytial Virus Vaccines," Vaccine, Oct. 2007, vol. 25, No. 42, pp. 7372-7378.
International Preliminary Report on Patentability for International (PCT) Patent Application No. PCT/US2015/060672, dated May 17, 2018 8 pages.
Official Action for European Patent Application No. 16794904.9, dated Jun. 17, 2020 8 pages.
Fearns, Rachel et al., "Mapping the Transcription and Replication Promoters of Respiratory Syncytial Virus", Journal of Virology, Feb. 2002, pp. 1663-1672, vol. 76, No. 4.
Ball, L. Andrew and Carol N. White, "Order of transcription of genes of vesicular stomatitis virus", Proc. Nat. Acad. Sci. USA, Feb. 1976, pp. 442-446, vol. 73, No. 2.
Emerson, Suzanne U., "Reconstitution Studies Detect a Single Polymerase Entry Site on the Vesicular Stomatitis Virus Genome", Cell, Dec. 1982 (part 2), pp. 635-642, vol. 31.
Dickens, Lillian E. et al., "Transcriptional Mapping of Human Respiratory Syncytial Virus", Journal of Virology, Nov. 1984, pp. 364-369, vol. 52, No. 2.
Kuo, Lili et al., "Effect of Mutations in the Gene-Start and Gene-End Sequence Motifs on Transcription of Monocistronic and Dicistronic Minigenomes of Respiratory Syncytial Virus", Journal of Virology, Oct. 1996, pp. 6892-6901, vol. 70, No. 10.
Collins, Peter L. et al., "Rescue of synthetic analogs of respiratory syncytial virus genomic RNA and effect of truncations and mutations on the expression of a foreign reporter gene", Proc. Natl. Acad. Sci USA, Nov. 1991, pp. 9663-9667, vol. 88.
Cowton, Vanessa M. and Rachel Fearns, "Evidence that the respiratory syncytial virus polymerase is recruited to nucleotides 1 to 11 at the 3' end of the nucleocapsid and can scan to access internal signals", Journal of Virology, Sep. 2005, pp. 11311-11322, vol. 79, No. 17, [Abstract].
De, Bishnu P. and Amiya K. Banerjee, "Rescue of Synthetic Analogs of Genome RNA of Human Parainfluenza Virus Type 3", Virology, 1993, pp. 344-348, vol. 196.
Smallwood, Sherin and Sue A. Moyer, "Promoter Analysis of the Vesicular Stomatitis RNA Polymerase", Virology, 1993, pp. 254-263, vol. 192.

(56) References Cited

OTHER PUBLICATIONS

Whitehead, Stephen S et al., "Recombinant Respiratory Syncytial Virus (RSV) Bearing a Set of Mutations from Cold-Passaged RSV is Attenuated in Chimpanzees", Journal of Virology, May 1998, pp. 4467-4471, vol. 72, No. 5.

* cited by examiner

ACGGGAAAAAATGCGTACAACAAACTTGCATAAACCAAAAAAATGGGGCAAATAAGAATTTGATAAGTACCACTT
AAATTTAACTCCCTTGGTTAGAGATGGGCAGCAATTCATTGAGTATGATAAAAGTTAGATTACAAAATTTGTTTGA
CAATGATGAAGTAGCATTGTTAAAAATAACATGCTATACTGATAAATTAATACATTTAACTAATGCTTTGGCTAAGG
CAGTGATACATACAATCAAATTGAATGGCATTGTGTTTGTGCATGTTATTACAAGTAGTGATATTTGCCCTAATAAT
AATATTGTAGTAAAATCCAATTTCACAACAATGCCAGTACTACAAAATGGAGGTTATATATGGGAAATGATGGAAT
TAACACATTGCTCTCAACCTAACGGTCTACTAGATGACAATTGTGAAATTAAATTCTCCAAAAAACTAAGTGATTCA
ACAATGACCAATTATATGAATCAATTATCTGAATTACTTGGATTTGATCTTAATCCATAAATTATAATTAATATCAAC
TAGCAAATCAATGTCACTAACACCATTAGTTAATATAAAACTTAACAGAAGACAAAAATGGGGCAAATAAATCAAT
TCAGCCAACCCAACCATGGACACAACCCACAATGATAATACACCACAAAGACTGATGATCACAGACATGAGACCG
TTGTCACTTGAGACCATAATAACATCACTAACCAGAGACATCATAACACACAAATTTATATACTTGATAAATCATGA
ATGCATAGTGAGAAGACTTGATGAAAGACAGGCCACATTTACATTCCTGGTCAACTATGAAATGAAACTATTACAC
AAAGTAGGAAGCACTAAATATAAAAAATATACTGAATACAACACAAAATATGGCACTTTCCCTATGCCAATATTCA
TCAATCATGATGGGTTCTTAGAATGCATTGGCATTAAGCCTACAAAGCATACTCCCATAATATACAAGTATGATCTC
AATCCATAAATTTCAACACAATATTCACACAATCTAAAACAACAACTCTATGCATAACTATACTCCATAGTCCAGAT
GGAGCCTGAAAATTATAGTAATTTAAAATTAAGGAGAGATATAAGATAGAAGATGGGGCAAATACAAAGATGGC
TCTTAGCAAAGTCAAGTTGAATGATACACTCAACAAGGATCAACTTCTGTCATCCAGCAAATACGCCATCCAACGG
AGCACAGGAGATAGTATTGATACTCCTAATTATGATGTGCAGAAACACATCAATAAGTTATGTGGCATGTTATTAA
TCACAGAAGATGCTAATCATAAATTCACTGGGTTAATAGGTATGTTATATGCGATGTCTAGGTTAGGAAGAGAAG
ACACCATAAAAATACTCAGAGATGCGGGATATCATGTAAAAGCAAATGGAGTAGATGTAACAACACATCGTCAAG
ACATTAATGGAAAAGAAATGAAATTTGAAGTGTTAACATTGGCAAGCTTAACAACTGAAATTCAAATCAACATTGA
GATAGAATCTAGAAAATCCTACAAAAAAATGCTAAAAGAAATGGGAGAGGTAGCTCCAGAATACAGGCATGACTC
TCCTGATTGTGGGATGATAATATTATGTATAGCAGCATTAGTAATAACTAAATTAGCAGCAGGGGACAGATCTGGT
CTTACAGCCGTGATTAGGAGAGCTAATAATGTCCTAAAAAATGAAATGAAACGTTACAAAGGCTTACTACCCAAG
GACATAGCCAACAGCTTCTATGAAGTGTTTGAAAAACATCCCCACTTTATAGATGTTTTTGTTCATTTTGGTATAGC
ACAATCTTCTACCAGAGGTGGCAGTAGAGTTGAAGGGATTTTTGCAGGATTGTTTATGAATGCCTATGGTGCAGG
GCAAGTGATGTTACGGTGGGGAGTCTTAGCAAAATCAGTTAAAAATATTATGTTAGGACATGCTAGTGTGCAAGC
AGAAATGGAACAAGTTGTTGAGGTTTATGAATATGCCCAAAAATTGGGTGGTGAAGCAGGATTCTACCATATATT
GAACAACCCAAAAGCATCATTATTATCTTTGACTCAATTTCCTCACTTCTCCAGTGTAGTATTAGGCAATGCTGCTG
GCCTAGGCATAATGGGAGAGTACAGAGGTACACCGAGGAATCAAGATCTATATGATGCAGCAAAGGCATATGCT
GAACAACTCAAAGAAATGGTGTGATTAACTACAGTGTACTAGACTTGACAGCAGAAGAACTAGAGGCTATCAAA
CATCAGCTTAATCCAAAAGATAATGATGTAGAGCTTTGAGTTAATAAAAAATGGGGCAAATAAATCATCATGGAA
AAGTTTGCTCCTGAATTCCATGGAGAAGATGCAAACAACAGGGCTACTAAATTCCTAGAATCAATAAAGGGCAAA
TTCACATCACCCAAAGATCCCAAGAAAAAAGATAGTATCATATCTGTCAACTCAATAGATATAGAAGTAACCAAAG
AAAGCCCTATAACATCAAATTCAACTATTATCAACCCAACAAATGAGACAGATGATACTGCAGGGAACAAGCCCAA
TTATCAAAGAAAACCTCTAGTAAGTTTCAAAGAAGACCCTACACCAAGTGATAATCCCTTTTCTAAACTATACAAAG
AAACCATAGAAACATTTGATAACAATGAAGAAGAATCCAGCTATTCATACGAAGAAATAAATGATCAGACAAACG
ATAATATAACAGCAAGATTAGATAGGATTGATGAAAATTAAGTGAAATACTAGGAATGCTTCACACATTAGTAGT
GGCAAGTGCAGGACCTACATCTGCTCGGGATGGTATAAGAGATGCCATGGTTGGTTTAAGAGAAGAAATGATAG
AAAAAATCAGAACTGAAGCATTAATGACCAATGACAGATTAGAAGCTATGGCAAGACTCAGGAATGAGGAAAGT
GAAAAGATGGCAAAAGACACATCAGATGAAGTGTCTCTCAATCCAACATCAGAGAAATTGAACAACCTATTGGAA
GGGAATGATAGTGACAATGATCTATCACTTGAAGATTTCTGATTAGTTACCAATCTTCACATCAACACACAATACCA

FIG. 6

```
ACAGAAGACCAACAAACTAACCAACCCAATCATCCAACCAAACATCCATCCGCCAATCAGCCAAACAGCCAACAAA
ACAACCAGCCAATCCAAAACTAACCACCCGGAAAAAATCTATAATATAGTTACAAAAAAAGGAAAGGGTGGGGCA
AATATGGAAACATACGTGAACAAGCTTCACGAAGGCTCCACATACACAGCTGCTGTTCAATACAATGTCTTAGAA
AAGACGATGACCCTGCATCACTTACAATATGGGTGCCCATGTTCCAATCATCTATGCCAGCAGATTTACTTATAAAA
GAACTAGCTAATGTCAACATACTAGTGAAACAAATATCCACACCCAAGGGACCTTCACTAAGAGTCATGATAAACT
CAAGAAGTGCAGTGCTAGCACAAATGCCCAGCAAATTTACCATATGCGCTAATGTGTCCTTGGATGAAAGAAGCA
AACTAGCATATGATGTAACCACACCCTGTGAAATCAAGGCATGTAGTCTAACATGCCTAAAATCAAAAAATATGTT
GACTACAGTTAAAGATCTCACTATGAAGACACTCAACCCTACACATGATATTATTGCTTTATGTGAATTTGAAAACA
TAGTAACATCAAAAAAAGTCATAATACCAACATACCTAAGATCCATCAGTGTCAGAAATAAAGATCTGAACACACT
TGAAAATATAACAACCACTGAATTCAAAAATGCTATCACAAATGCAAAATCATCCCTTACTCAGGATTACTATTAG
TCATCACAGTGACTGACAACAAAGGAGCATTCAAATACATAAAGCCACAAAGTCAATTCATAGTAGATCTTGGAGC
TTACCTAGAAAAGAAAGTATATATTATGTTACCACAAATTGGAAGCACACAGCTACACGATTTGCAATCAAACCC
ATGGAAGATTAACCTTTTTCCTCTACATCAGTGTGTTAATTCATACAAACTTTCTACCTACATTCTTCACTTCACCATC
ACAATCACAAACACTCTGTGGTTCAACCAATCAAACAAAACTTATCTGAAGTCCCAGATCATCCCAAGTCATTGTTT
ATCAGATCTAGTACTCAAATAAGTTAATAAAAAATATACACATGGGGCAAATAATCATTGGAGGAAATCCAACTAA
TCACAATATCTGTTAACATAGACAAGTCCACACACCATACAGAATCAACCAATGGAAAATACATCCATAACAATAG
AATTCTCAAGCAAATTCTGGCCTTACTTTACACTAATACACATGATCACAACAATAATCTCTTTGCTAATCATAATCT
CCATCATGATTGCAATACTAAACAAACTTTGTGAATATAACGTATTCCATAACAAAACCTTTGAGTTACCAAGAGCT
CGAGTCAACACATAGCATTCATCAATCCAACAGCCCAAAACAGTAACCTTGCATTTAAAAATGAACAACCCCTACCT
CTTTACAACACCTCATTAACATCCCACCATGCAAACCACTATCCATACTATAAAGTAGTTAATTAAAAATAGTCATAA
CAATGAACTAGGATATCAAGACTAACAATAACATTGGGGCAAATGCAAACATGTCCAAAAACAAGGACCAACGCA
CCGCTAAGACATTAGAAAGGACCTGGGACACTCTCAATCATTTATTATTCATATCATCGTGCTTATATAAGTTAAAT
CTTAAATCTGTAGCACAAATCACATTATCCATTCTGGCAATGATAATCTCAACTTCACTTATAATTGCAGCCATCATA
TTCATAGCCTCGGCAAACCACAAAGTCACACCAACAACTGCAATCATACAAGATGCAACAAGCCAGATCAAGAACA
CAACCCCAACATACCTCACCCAGAATCCTCAGCTTGGAATCAGTCCCTCTAATCCGTCTGAAATTACATCACAAATC
ACCACCATACTAGCTTCAACAACACCAGGAGTCAAGTCAACCCTGCAATCCACAACAGTCAAGACCAAAAACACAA
CAACAACTCAAACACAACCCAGCAAGCCCACCACAAAACAACGCCAAAACAAACCACCAAGCAAACCCAATAATG
ATTTTCACTTTGAAGTGTTCAACTTTGTACCCTGCAGCATATGCAGCAACAATCCAACCTGCTGGGCTATCTGCAAA
AGAATACCAAACAAAAAACCAGGAAAGAAAACCACTACCAAGCCCACAAAAAAACCAACCCTCAAGACAACCAAA
AAAGATCCCAAACCTCAAACCACTAAATCAAAGGAAGTACCCACCACCAAGCCCACAGAAGAGCCAACCATCAAC
ACCACCAAAACAAACATCATAACTACACTACTCACCTCCAACACCACAGGAAATCCAGAACTCACAAGTCAAATGG
AAACCTTCCACTCAACTTCCTCCGAAGGCAATCCAAGCCCTTCTCAAGTCTCTACAACATCCGAGTACCCATCACAA
CCTTCATCTCCACCCAACACACCACGCCAGTAGTTACTTAAAAACATATTATCACAAAAAGCCATGACCAACTTAAA
CAGAATCAAAGTAAACTCTGGGGCAAATAACAATGGAGTTGCTAATCCTCAAAGCAAATGCAATTACCACAATCCT
CACTGCAGTCACATTTTGTTTTGCTTCTGGTCAAAACATCACTGAAGAATTTTATCAATCAACATGCAGTGCAGTTA
GCAAAGGCTATCTTAGTGCTCTGAGAACTGGTTGGTATACCAGTGTTATAACTATAGAATTAAGTAATATCAAGAA
AAATAAGTGTAATGGAACAGATGCTAAGGTAAAATTGATAAAACAAGAATTAGATAAATATAAAAATGCTGTAAC
AGAATTGCAGTTGCTCATGCAAAGCACACAAGCAACAAACAATCGAGCCAGAAGAGAACTACCAAGGTTTATGAA
TTATACACTCAACAATGCCAAAAAAACCAATGTAACATTAAGCAAGAAAAGGAAAAGAAGATTTCTTGGTTTTTTG
TTAGGTGTTGGATCTGCAATCGCCAGTGGCGTTGCTGTATCTAAGGTCCTGCACCTAGAAGGGGAAGTGAACAAG
ATCAAAAGTGCTCTACTATCCACAAACAAGGCTGTAGTCAGCTTATCAAATGGAGTCAGTGTCTTAACCAGCAAAG
```

FIG. 6 - CONTINUED

```
TGTTAGACCTCAAAAACTATATAGATAAACAATTGTTACCTATTGTGAACAAGCAAAGCTGCAGCATATCAAATAT
AGAAACTGTGATAGAGTTCCAACAAAAGAACAACAGACTACTAGAGATTACCAGGGAATTTAGTGTTAATGCAGG
TGTAACTACACCTGTAAGCACTTACATGTTAACTAATAGTGAATTATTGTCATTAATCAATGATATGCCTATAACAA
ATGATCAGAAAAAGTTAATGTCCAACAATGTTCAAATAGTTAGACAGCAAAGTTACTCTATCATGTCCATAATAAA
AGAGGAAGTCTTAGCATATGTAGTACAATTACCACTATATGGTGTTATAGATACACCCTGTTGGAAACTACACACA
TCCCCTCTATGTACAACCAACACAAAAGAAGGGTCCAACATCTGTTTAACAAGAACTGACAGAGGATGGTACTGTG
ACAATGCAGGATCAGTATCTTTCTTCCCACAAGCTGAAACATGTAAAGTTCAATCAAATCGAGTATTTTGTGACACA
ATGAACAGTTTAACATTACCAAGTGAAGTAAATCTCTGCAATGTTGACATATTCAACCCCAAATATGATTGTAAAAT
TATGACTTCAAAAACAGATGTAAGCAGCTCCGTTATCACATCTCTAGGAGCCATTGTGTCATGCTATGGCAAAACT
AAATGTACAGCATCCAATAAAAATCGTGGAATCATAAAGACATTTTCTAACGGGTGCGATTATGTATCAAATAAAG
GGGTGGACACTGTGTCTGTAGGTAACACATTATATTATGTAAATAAGCAAGAAGGTAAAAGTCTCTATGTAAAAG
GTGAACCAATAATAAATTTCTATGACCCATTAGTATTCCCCTCTGATGAATTTGATGCATCAATATCTCAAGTCAAC
GAGAAGATTAACCAGAGCCTAGCATTTATTCGTAAATCCGATGAATTATTACATAATGTAAATGCCGGTAAATCCA
CCACAAATATCATGATAACTACTATAATTATAGTGATTATAGTAATATTGTTATCATTAATTGCTGTTGGACTGCTCT
TATACTGTAAGGCCAGAAGCACACCAGTCACACTAAGCAAAGATCAACTGAGTGGTATAAATAATATTGCATTTAG
TAACTAAATAAAAATAGCACCTAATCATGTTCTTACAATGGTTTACTATCTGCTCATAGACAACCCATCTGTCATTG
GATTTTCTTAAAATCTGAACTTCATTGAAACTCTCATCTATAAACCATCTCACTTACACTATTTAAGTAGATTCCTAGT
TTATAGTTATATAAAACACAATTGAATGCCAGATTAACTTACCATCTGTAAAAATGAAAACTGGGGCAAATATGTC
ACGAAGGAATCCTTGCAAATTTGAAATTCGAGGTCATTGCTTAAATGGTAAGAGGTGTCATTTTAGTCATAATTATT
TTGAATGGCCACCGCATGCACTGCTTGTAAGACAAAACTTTATGTTAAACAGAATACTTAAGTCTATGGATAAAAG
TATAGATACCTTATCAGAAATAAGTGGAGCTGCAGAGTTGGACAGAACAGAAGAGTATGCTCTTGGTGTAGTTGG
AGTGCTAGAGAGTTATATAGGATCAATAAACAATATAACTAAACAATCAGCATGTGTTGCCATGAGCAAACTCCTC
ACTGAACTCAATAGTGATGATATCAAAAAGCTGAGGGACAATGAAGAGCTAAATTCACCCAAGATAAGAGTGTAC
AATACTGTCATATCATATATTGAAAGCAACAGGAAAAACAATAAACAAACTATCCATCTGTTAAAAAGATTGCCAG
CAGACGTATTGAAGAAAACCATCAAAAACACATTGGATATCCATAAGAGCATAACCATCAACAACCCAAAAGAATC
AACTGTTAGTGATACAAATGACCATGCCAAAAATAATGATACTACCTGACAAATAAGCTTCAATTCTAACACTCACC
ACATCGTTACATTATTAATTCAAACAATTCAAGTTGTGGGACAAAATGGATCCCATTATTAATGGAAATTCTGCTAA
TGTTTATCTAACCGATAGTTATTTAAAAGGTGTTATCTCTTTCTCAGAGTGTAATGCTTTAGGAAGTTACATATTCAA
TGGTCCTTATCTCAAAAATGATTATACCAACTTAATTAGTAGACAAAATCCATTAATAGAACACATGAATCTAAAGA
AACTAAATATAACACAGTCCTTAATATCTAAGTATCATAAAGGTGAAATAAAATTAGAAGAACCTACTTATTTTCAG
TCATTACTTATGACATACAAGAGTATGACCTCGTCAGAACAGATTGCTACCACTAATTTACTTAAAAAGATAATAAG
AAGAGCTATAGAAATAAGTGATGTCAAAGTCTATGCTATATTGAATAAACTAGGGCTTAAAGAAAAGGACAAGAT
TAAATCCAACAATGGACAAGATGAAGACAACTCAGTTATTACGACCATAATCAAAGATGATATACTTTCAGCTGTT
AAAGATAATCAATCTCATCTTAAAGCAGACAAAAATCACTCTACAAAACAAAAAGACACAATCAAAACAACACTCT
TGAAGAAATTGATGTGTTCAATGCAACATCCTCCATCATGGTTAATACATTGGTTTAACTTATACACAAAATTAAAC
AACATATTAACACAGTATCGATCAAATGAGGTAAAAAACCATGGGTTTACATTGATAGATAATCAAACTCTTAGTG
GATTTCAATTTATTTTGAACCAATATGGTTGTATAGTTTATCATAAGGAACTCAAAAGAATTACTGTGACAACCTAT
AATCAATTCTTGACATGGAAAGATATTAGCCTTAGTAGATTAAATGTTTGTTTAATTACATGGATTAGTAACTGCTT
GAACACATTAAATAAAAGCTTAGGCTTAAGATGCGGATTCAATAATGTTATCTTGACACAACTATTCCTTTATGGAG
ATTGTATACTAAAGCTATTTCACAATGAGGGGTTCTACATAATAAAAGAGGTAGAGGGATTTATTATGTCTCTAATT
```

FIG. 6 - CONTINUED

```
TTAAATATAACAGAAGAAGATCAATTCAGAAAACGATTTTATAATAGTATGCTCAACAACATCACAGATGCTGCTA
ATAAAGCTCAGAAAAATCTGCTATCAAGAGTATGTCATACATTATTAGATAAGACAGTGTCCGATAATATAATAAA
TGGCAGATGGATAATTCTATTAAGTAAGTTCCTTAAATTAATTAAGCTTGCAGGTGACAATAACCTTAACAATCTGA
GTGAACTATATTTTTTGTTCAGAATATTTGGACACCCAATGGTAGATGAAAGACAAGCCATGGATGCTGTTAAAAT
TAATTGCAATGAGACCAAATTTTACTTGTTAAGCAGTCTGAGTATGTTAAGAGGTGCCTTTATATATAGAATTATAA
AAGGGTTTGTAAATAATTACAACAGATGGCCTACTTTAAGAAATGCTATTGTTTTACCCTTAAGATGGTTAACTTAC
TATAAACTAAACACTTATCCTTCTTTGTTGGAACTTACAGAAAGAGATTTGATTGTGTTATCAGGACTACGTTTCTAT
CGTGAGTTTCGGTTGCCTAAAAAAGTGGATCTTGAAATGATTATAAATGATAAAGCTATATCACCTCCTAAAAATTT
GATATGGACTAGTTTCCCTAGAAATTACATGCCATCACACATACAAAACTATATAGAACATGAAAAATTAAAATTTT
CCGAGAGTGATAAATCAAGAAGAGTATTAGAGTATTATTTAAGAGATAACAAATTCAATGAATGTGATTTATACAA
CTGTGTAGTTAATCAAAGTTATCTCAACAACCCTAATCATGTGGTATCATTGACAGGCAAAGAAAGAGAACTCAGT
GTAGGTAGAATGTTTGCAATGCAACCGGGAATGTTCAGACAGGTTCAAATATTGGCAGAGAAATGATAGCTGAA
AACATTTTACAATTCTTTCCTGAAAGTCTTACAAGATATGGTGATCTAGAACTACAAAAAATATTAGAATTGAAAGC
AGGAATAAGTAACAAATCAAATCGCTACAATGATAATTACAACAATTACATTAGTAAGTGCTCTATCATCACAGAT
CTCAGCAAATTCAATCAAGCATTTCGATATGAAACGTCATGTATTTGTAGTGATGTGCTGGATGAACTGCATGGTG
TACAATCTCTATTTTCCTGGTTACATTTAACTATTCCTCATGTCACAATAATATGCACATATAGGCATGCACCCCCCT
ATATAGGAGATCATATTGTAGATCTTAACAATGTAGATGAACAAAGTGGATTATATAGATATCACATGGGTGGCAT
CGAAGGGTGGTGTCAAAAACTATGGACCATAGAAGCTATATCACTATTGGATCTAATATCTCTCAAAGGGAAATTC
TCAATTACTGCTTTAATTAATGGTGACAATCAATCAATAGATATAAGCAAACCAATCAGACTCATGGAAGGTCAAA
CTCATGCTCAAGCAGATTATTTGCTAGCATTAAATAGCCTTAAATTACTGTATAAAGAGTATGCAGGCATAGGCCA
CAAATTAAAAGGAACTGAGACTTATATATCACGAGATATGCAATTTATGAGTAAAACAATTCAACATAACGGTGTA
TATTACCCAGCTAGTATAAAGAAAGTCCTAAGAGTGGGACCGTGGATAAACACTATACTTGATGATTTCAAAGTGA
GTCTAGAATCTATAGGTAGTTTGACACAAGAATTAGAATATAGAGGTGAAAGTCTATTATGCAGTTTAATATTTAG
AAATGTATGGTTATATAATCAGATTGCTCTACAATTAAAAAAATCATGCATTATGTAACAATAAACTATATTTGGACA
TATTAAAGGTTCTGAAACACTTAAAAACCTTTTTTAATCTTGATAATATTGATACAGCATTAACATTGTATATGAATT
TACCCATGTTATTTGGTGGTGGTGATCCCAACTTGTTATATCGAAGTTTCTATAGAAGAACTCCTGACTTCCTCACA
GAGGCTATAGTTCACTCTGTGTTCATACTTAGTTATTATACAAACCATGACTTAAAAGATAAACTTCAAGATCTGTC
AGATGATAGATTGAATAAGTTCTTAACATGCATAATCACGTTTGACAAAAACCCTAATGCTGAATTCGTAACATTGA
TGAGAGATCCTCAAGCTTTAGGGTCTGAGAGACAAGCTAAAATTACTAGCGAAATCAATAGACTGGCAGTTACAG
AGGTTTTGAGTACAGCTCCAAACAAAATATTCTCCAAAAGTGCACAACATTATACTACTACAGAGATAGATCTAAA
TGATATTATGCAAAATATAGAACCTACATATCCTCATGGGCTAAGAGTTGTTTATGAAAGTTTACCCTTTTATAAAG
CAGAGAAAATAGTAAATCTTATATCAGGTACAAAATCTATAACTAACATACTGGAAAAAACTTCTGCCATAGACTT
AACAGATATTGATAGAGCCACTGAGATGATGAGGAAAAACATAACTTTGCTTATAAGGATACTTCCATTGGATTGT
AACAGAGATAAAAGAGAGATATTGAGTATGGAAAACCTAAGTATTACTGAATTAAGCAAATATGTTAGGGAAAGA
TCTTGGTCTTTATCCAATATAGTTGGTGTTACATCACCCAGTATCATGTATACAATGGACATCAAATATACTACAAG
CACTATATCTAGTGGCATAATTATAGAGAAATATAATGTTAACAGTTTAACACGTGGTGAGAGAGGACCCACTAAA
CCATGGGTTGGTTCATCTACACAAGAGAAAAAAACAATGCCAGTTTATAATAGACAAGTCTTAACCAAAAAACAGA
GAGATCAAATAGATCTATTAGCAAAATTGGATTGGGTGTATGCATCTATAGATAACAAGGATGAATTCATGGAAG
AACTCAGCATAGGAACCCTTGGGTTAACATATGAAAAGGCCAAGAAATTATTTCCACAATATTTAAGTGTCAATTA
TTTGCATCGCCTTACAGTCAGTAGTAGACCATGTGAATTCCCTGCATCAATACCAGCTTATAGAACAACAAATTATC
ACTTTGACACTAGCCCTATTAATCGCATATTAACAGAAAAGTATGGTGATGAAGATATTGACATAGTATTCCAAAA
```

FIG. 6 - CONTINUED

```
CTGTATAAGCTTTGGCCTTAGTTTAATGTCAGTAGTAGAACAATTTACTAATGTATGTCCTAACAGAATTATTCTCAT
ACCTAAGCTTAATGAGATACATTTGATGAAACCTCCCATATTCACAGGTGATGTTGATATTCACAAGTTAAAACAAG
TGATACAAAAACAGCATATGTTTTTACCAGACAAAATAAGTTTGACTCAATATGTGGAATTATTCTTAAGTAATAAA
ACACTCAAATCTGGATCTCATGTTAATTCTAATTTAATATTGGCACATAAAATATCTGACTATTTTCATAATACTTAC
ATTTTAAGTACTAATTTAGCTGGACATTGGATTCTGATTATACAACTTATGAAAGATTCTAAAGGTATTTTTGAAAA
AGATTGGGGAGAGGGATATATAACTGATCATATGTTTATTAATTTGAAAGTTTTCTTCAATGCTTATAAGACCTATC
TCTTGTGTTTTCATAAAGGTTATGGCAAAGCAAAGCTGGAGTGTGATATGAACACTTCAGATCTTCTATGTGTATTG
GAATTAATAGACAGTAGTTATTGGAAGTCTATGTCTAAGGTATTTTTAGAACAAAAAGTTATCAAATACATTCTTAG
CCAAGATGCAAGTTTACATAGAGTAAAAGGATGTCATAGCTTCAAATTATGGTTTCTTAAACGTCTTAATGTAGCA
GAATTCACAGTTTGCCCTTGGGTTGTTAACATAGATTATCATCCAACACATATGAAAGCAATATTAACTTATATAGA
TCTTGTTAGAATGGGATTGATAAATATAGATAGAATACACATTAAAAATAAACACAAATTCAATGATGAATTTTATA
CTTCTAATCTCTTCTACATTAATTATAACTTCTCAGATAATACTCATCTATTAACTAAACATATAAGGATTGCTAATTC
TGAATTAGAAAATAATTACAACAAATTATATCATCCTACACCAGAAACACTAGAGAATATACTAGCCAATCCGATTA
AAAGTAATGACAAAAAGACACTGAATGACTATTGTATAGGTAAAAATGTTGACTCAATAATGTTACCATTGTTATC
TAATAAGAAGCTTATTAAATCGTCTGCAATGATTAGAACCAATTACAGCAAACAAGATTTGTATAATTTATTCCCTA
TGGTTGTGATTGATAGAATTATAGATCATTCAGGCAATACAGCCAAATCCAACCAACTTTACACTACTACTTCCCAC
CAAATATCTTTAGTGCACAATAGCACATCACTTTACTGCATGCTTCCTTGGCATCATATTAATAGATTCAATTTTGTA
TTTAGTTCTACAGGTTGTAAAATTAGTATAGAGTATATTTTAAAAGATCTTAAAATTAAAGATCCCAATTGTATAGC
ATTCATAGGTGAAGGAGCAGGGAATTTATTATTGCGTACAGTAGTGGAACTTCATCCTGACATAAGATATATTTAC
AGAAGTCTGAAAGATTGCAATGATCATAGTTTACCTATTGAGTTTTTAAGGCTGTACAATGGACATATCAACATTG
ATTATGGTGAAAATTTGACCATTCCTGCTACAGATGCAACCAACAACATTCATTGGTCTTATTTACATATAAAGTTT
GCTGAACCTATCAGTCTTTTTGTCTGTGATGCCGAATTGTCTGTAACAGTCAACTGGAGTAAAATTATAATAGAATG
GAGCAAGCATGTAAGAAAGTGCAAGTACTGTTCCTCAGTTAATAAATGTATGTTAATAGTAAAATATCATGCTCAA
GATGATATTGATTTCAAATTAGACAATATAACTATATTAAAAACTTATGTATGCTTAGGCAGTAAGTTAAAGGGATC
GGAGGTTTACTTAGTCCTTACAATAGGTCCTGCGAATATATTCCCAGTATTTAATGTAGTACAAAATGCTAAATTGA
TACTATCAAGAACCAAAAATTTCATCATGCCTAAGAAAGCTGATAAAGAGTCTATTGATGCAAATATTAAAAGTTT
GATACCCTTTCTTTGTTACCCTATAACAAAAAAAGGAATTAATACTGCATTGTCAAAACTAAAGAGTGTTGTTAGTG
GAGATATACTATCATATTCTATAGCTGGACGTAATGAAGTTTTCAGCAATAAACTTATAAATCATAAGCATATGAAC
ATCTTAAAATGGTTCAATCATGTTTTAAATTTCAGATCAACAGAACTAAACTATAACCATTTATATATGGTAGAATCT
ACATATCCTTACCTAAGTGAATTGTTAAACAGCTTGACAACCAATGAACTTAAAAAACTGATTAAAATCACAGGTA
GTCTGTTATACAACTTTCATAATGAATAATGAATAAAGATCTTATAATAAAAATTCCCATAGCTATACACTAACACT
GTATTCAATTATAGTTATTAAAAATTAAAAATCATATAATTTTTTAAATAACTTTTAGTGAACTAATCCTAAAGTTAT
CATTTTAATCTTGGAGGAATAAATTTAAACCCTAATCTAATTGGTTTATATGTGTATTAACTAAATTACGAGATATTA
GTTTTTGACACTTTTTTTCTCGT
```

FIG. 6 - CONTINUED

```
ACGGGAAAAAATGCGTACAACAAACTTGCATAAACCAAAAAAATGGGGCAAATAAGAATTTGATAAGTACCACTT
AAATTTAACTCCCTTGGTTAGAGATGGGCAGCAATTCATTGAGTATGATAAAAGTTAGATTACAAAATTTGTTTGA
CAATGATGAAGTAGCATTGTTAAAAATAACATGCTATACTGATAAATTAATACATTTAACTAATGCTTTGGCTAAGG
CAGTGATACATACAATCAAATTGAATGGCATTGTGTTTGTGCATGTTATTACAAGTAGTGATATTTGCCCTAATAAT
AATATTGTAGTAAAATCCAATTTCACAACAATGCCAGTACTACAAAATGGAGGTTATATATGGGAAATGATGGAAT
TAACACATTGCTCTCAACCTAATGGTCTACTAGATGACAATTGTGAAATTAAATTCTCCAAAAAACTAAGTGATTCA
ACAATGACCAATTATATGAATCAATTATCTGAATTACTTGGATTTGATCTTAATCCATAAATTATAATTAATATCAAC
TAGCAAATCAATGTCACTAACACCATTAGTTAATATAAAACTTAACAGAAGACAAAAATGGGGCAAATAAATCAAT
TCAGCCAACCCAACCATGGACACAACCCACAATGATAATACACCACAAAGACTGATGATCACAGACATGAGACCG
TTGTCACTTGAGACCATAATAACATCACTAACCAGAGACATCATAACACACAAATTTATATACTTGATAAATCATGA
ATGCATAGTGAGAAAACTTGATGAAAGACAGGCCACATTTACATTCCTGGTCAACTATGAAATGAAACTATTACAC
AAAGTAGGAAGCACTAAATATAAAAAATATACTGAATACAACACAAAATATGGCACTTTCCCTATGCCAATATTCA
TCAATCATGATGGGTTCTTAGAATGCATTGGCATTAAGCCTACAAAGCATACTCCCATAATATACAAGTATGATCTC
AATCCATAAATTTCAACACAATATTCACACAATCTAAAACAACAACTCTATGCATAACTATACTCCATAGTCCAGAT
GGAGCCTGAAAATTATAGTAATTTAAAACTTAAGGAGAGATATAAGATAGAAGATGGGGCAAATACAACCATGGC
TCTTAGCAAAGTCAAGTTGAATGATACACTCAACAAAGATCAACTTCTGTCATCCAGCAAATACACCATCCAACGG
AGCACAGGAGATAGTATTGATACTCCTAATTATGATGTGCAGAAACACATCAATAAGTTATGTGGCATGTTATTAA
TCACAGAAGATGCTAATCATAAATTCACTGGGTTAATAGGTATGTTATATGCGATGTCTAGGTTAGGAAGAGAAG
ACACCATAAAAATACTCAGAGATGCGGGATATCATGTAAAAGCAAATGGAGTAGATGTAACAACACATCGTCAAG
ACATTAATGGAAAAGAAATGAAATTTGAAGTGTTAACATTGGCAAGCTTAACAACTGAAATTCAAATCAACATTGA
GATAGAATCTAGAAAATCCTACAAAAAAATGCTAAAAGAAATGGGAGAGGTAGCTCCAGAATACAGGCATGACTC
TCCTGATTGTGGGATGATAATATTATGTATAGCAGCATTAGTAATAACTAAATTAGCAGCAGGGGACAGATCTGGT
CTTACAGCCGTGATTAGGAGAGCTAATAATGTCCTAAAAAATGAAATGAAACGTTACAAAGGCTTACTACCCAAG
GACATAGCCAACAGCTTCTATGAAGTGTTTGAAAAACATCCCCACTTTATAGATGTTTTTGTTCATTTTGGTATAGC
ACAATCTTCTACCAGAGGTGGCAGTAGAGTTGAAGGGATTTTTGCAGGATTGTTTATGAATGCCTATGGTGCAGG
GCAAGTGATGTTACGGTGGGGAGTCTTAGCAAAATCGATTAAAAATATTATGTTAGGACATGCTAGTGTGCAAGC
AGAAATGGAACAAGTTGTTGAGGTTTATGAATATGCCCAAAAATTGGGTGGTGAAGCAGGATTCTACCATATATT
GAACAACCCAAAAGCATCATTATTATCTTTGACTCAATTTCCTCACTTCTCCAGTGTAGTATTAGGCAATGCTGCTG
GCCTAGGCATAATGGGAGAGTACAGAGGTACACCGAGGAATCAAGATCTATATGATGCAGCAAAGGCATATGCT
GAACAACTCAAAGAAAATGGTGTGATTAACTACAGTGTACTAGACTTGACAGCAGAAGAACTAGAGGCTATCAAA
CATCAGCTTAATCCAAAAGATAATGATGTAGAGCTTTGAGTTAATAAAAAATGGGGCAAATAAATCATCATGGAA
AAGTTTGCTCCTGAATTCCATGGAGAAGATGCAAACAACAGGGCTACTAAATTCCTAGAATCAATAAAGGGCAAA
TTCACATCACCCAAAGATCCCAAGAAAAAAGATAGTATCATATCTGTCAACTCAATAGATATAGAAGTAACCAAAG
AAAGCCCTATAACATCAAATTCAACTATTATCAACCCAACAAATGAGACAGATGATACTGCAGGGAACAAGCCCAA
TTATCAAAGAAAACCTCTAGTAAGTTTCAAAGAAGACCCTACACCAAGTGATAATCCCTTTTCTAAACTATACAAAG
AAACCATAGAAACATTTGATAACAATGAAGAAGAATCCAGCTATTCATACGAAGAAATAAATGATCAGACAAACG
ATAATATAACAGCAAGATTAGATAGGATTGATGAAAAATTAAGTGAAATACTAGGAATGCTTCACACATTAGTAGT
GGCAAGTGCAGGACCTACATCTGCTCGGGATGGTATAAGAGATGCCATGGTTGGTTTAAGAGAAGAAATGATAG
AAAAAATCAGAACTGAAGCATTAATGACCAATGACAGATTAGAAGCTATGGCAAGACTCAGGAATGAGGAAAGT
GAAAAGATGGCAAAAGACACATCAGATGAAGTGTCTCTCAATCCAACATCAGAGAAATTGAACAACCTATTGGAA
GGGAATGATAGTGACAATGATCTATCACTTGAAGATTTCTGATTAGTTACCAATCTTCACATCAACACACAATACCA
```

FIG. 7

```
ACAGAAGACCAACAAACTAACCAACCCAATCATCCAACCAAACATCCATCCGCCAATCAGCCAAACAGCCAACAAA
ACAACCAGCCAATCCAAAACTAACCACCCGGAAAAAATCTATAATATAGTTACAAAAAAAGGAAAGGGTGGGGCA
AATATGGAAACATACGTGAACAAGCTTCACGAAGGCTCCACATACACAGCTGCTGTTCAATACAATGTCTTAGAAA
AAGACGATGACCCTGCATCACTTACAATATGGGTGCCCATGTTCCAATCATCTATGCCAGCAGATTTACTTATAAAA
GAACTAGCTAATGTCAACATACTAGTGAAACAAATATCCACACCCAAGGGACCTTCACTAAGAGTCATGATAAACT
CAAGAAGTGCAGTGCTAGCACAAATGCCCAGCAAATTTACCATATGCGCTAATGTGTCCTTGGATGAAAGAAGCA
AACTAGCATATGATGTAACCACACCCTGTGAAATCAAGGCATGTAGTCTAACATGCCTAAAATCAAAAAATATGTT
GACTACAGTTAAAGATCTCACTATGAAGACACTCAACCCTACACATGATATTATTGCTTTATGTGAATTTGAAAACA
TAGTAACATCAAAAAAAGTCATAATACCAACATACCTAAGATCCATCAGTGTCAGAAATAAAGATCTGAACACACT
TGAAAATATAACAACCACTGAATTCAAAAATGCTATCACAAATGCAAAAATCATCCCTTACTCAGGATTACTATTAG
TCATCACAGTGACTGACAACAAAGGAGCATTCAAATACATAAAGCCACAAAGTCAATTCATAGTAGATCTTGGAGC
TTACCTAGAAAAAGAAAGTATATATTATGTTACCACAAATTGGAAGCACACAGCTACACGATTTGCAATCAAACCC
ATGGAAGATTAACCTTTTTCCTCTACATCAGTGTGTTAATTCATACAAACTTTCTACCTACATTCTTCACTTCACCATC
ACAATCACAAACACTCTGTGGTTCAACCAATCAAACAAAACTTATCTGAAGTCCCAGATCATCCCAAGTCATTGTTT
ATCAGATCTAGTACTCAAATAAGTTAATTAAAAATAGTCATAACAATGAACTAGGATATCAAGACTAACAATAACA
TTGGGGCAAATGCAAACATGTCCAAAAACAAGGACCAACGCACCGCTAAGACATTAGAAAGGACCTGGGACACTC
TCAATCATTTATTATTCATATCATCGTGCTTATATAAGTTAAATCTTAAATCTGTAGCACAAATCACATTATCCATTCT
GGCAATGATAATCTCAACTTCACTTATAATTGCAGCCATCATATTCATAGCCTCGGCAAACCACAAAGTCACACCAA
CAACTGCAATCATACAAGATGCAACAAGCCAGATCAAGAACACAACCCCAACATACCTCACCCAGAATCCTCAGCT
TGGAATCAGTCCCTCTAATCCGTCTGAAATTACATCACAAATCACCACCATACTAGCTTCAACAACACCAGGAGTCA
AGTCAACCCTGCAATCCACAACAGTCAAGACCAAAAACACAACAACAACTCAAACACAACCCAGCAAGCCCACCAC
AAAACAACGCCAAAACAAACCACCAAGCAAACCCAATAATGATTTTCACTTTGAAGTGTTCAACTTTGTACCCTGCA
GCATATGCAGCAACAATCCAACCTGCTGGGCTATCTGCAAAAGAATACCAAACAAAAAACCAGGAAAGAAAACCA
CTACCAAGCCCACAAAAAAACCAACCCTCAAGACAACCAAAAAAGATCCCAAACCTCAAACCACTAAATCAAAGGA
AGTACCCACCACCAAGCCCACAGAAGAGCCAACCATCAACACCACCAAAACAAACATCATAACTACACTACTCACC
TCCAACACCACAGGAAATCCAGAACTCACAAGTCAAATGGAAACCTTCCACTCAACTTCCTCCGAAGGCAATCCAA
GCCCTTCTCAAGTCTCTACAACATCCGAGTACCCATCACAACCTTCATCTCCACCCAACACACCACGCCAGTAGTTAC
TTAAAAACATATTATCACAAAAGGCCTTGACCAACTTAAACAGAATCAAAATAAACTCTGGGGCAAATAACAATGG
AGTTGCTAATCCTCAAAGCAAATGCAATTACCACAATCCTCACTGCAGTCACATTTTGTTTTGCTTCTGGTCAAAAC
ATCACTGAAGAATTTTATCAATCAACATGCAGTGCAGTTAGCAAAGGCTATCTTAGTGCTCTGAGAACTGGTTGGT
ATACCAGTGTTATAACTATAGAATTAAGTAATATTAAGGAAAATAAGTGTAATGGAACAGATGCTAAGGTAAAATT
GATAAAACAAGAATTAGATAAATATAAAAATGCTGTAACAGAATTGCAGTTGCTCATGCAAAGTACTCCAGCAACA
AACAATCGAGCCAGAAGAGAACTACCAAGGTTTATGAATTATACACTCAACAATGCCAAAAAAACCAATGTAACAT
TAAGCAAGAAAAGGAAAAGAAGATTTCTTGGTTTTTTGTTAGGTGTTGGATCTGCAATCGCCAGTGGCGTTGCTGT
ATCTAAGGTCCTGCACCTAGAAGGGGAAGTGAACAAGATCAAAAGTGCTCTACTATCCACAAACAAGGCTGTAGT
CAGCTTATCAAATGGAGTTAGTGTTTTAACCAGCAAAGTGTTAGACCTCAAAAACTATATAGATAAACAATTGTTAC
CTATTGTGAACAAGCAAAGCTGCAGCATATCAAATATCGCGACTGTGATAGAGTTCCAACAAAAGAACAACAGAC
TACTAGAGATTACCAGGGAATTTAGTGTTAATGCAGGCGTAACTACACCTGTAAGCACTTACATGTTAACTAATAG
TGAATTATTGTCATTAATCAATGATATGCCTATAACAAATGATCAGAAAAAGTTAATGTCCAACAATGTTCAAATAG
TTAGACAGCAAAGTTACTCTATCATGTCCATAATAAAGAGGAAGTCTTAGCATATGTAGTACAATTACCACTATAT
GGTGTTATAGATACACCCTGTTGGAAACTACACACATCCCCTCTATGTACAACCAACACAAAAGAAGGGTCCAACA
```

FIG. 7 - CONTINUED

```
TCTGTTTAACAAGAACTGACAGAGGATGGTACTGTGACAATGCAGGATCAGTATCTTTCTTCCCACAAGCTGAAAC
ATGTAAAGTTCAATCAAATCGAGTATTTTGTGACACAATGAACAGTTTAACATTACCAAGTGAAGTAAATCTCTGCA
ATGTTGACATATTCAACCCCAAATATGATTGTAAAATTATGACTTCAAAAACAGATGTAAGCAGCTCCGTTATCACA
TCTCTAGGAGCCATTGTGTCATGCTATGGCAAAACTAAATGTACAGCATCCAATAAAAATCGTGGAATCATAAAGA
CATTTTCTAACGGGTGCGATTATGTATCAAATAAAGGGGTGGACACTGTGTCTGTAGGTAACACATTATATTATGT
AAATAAGCAAGAAGGTAAAAGTCTCTATGTAAAAGGTGAACCAATAATAAATTTCTATGACCCATTAGTATTCCCC
TCTGATGAATTTGATGCATCAATATCTCAAGTCAACGAGAAGATTAACCAGAGCCTAGCATTTATTCGTAAATCCGA
TGAATTATTACATAATGTAAATGCTGGTAAATCCACCATTAATATCATGATAACTACTATAATTATAGTGATTATAGT
AATATTGTTATCATTAATTGCTGTTGGACTGCTCTTATACTGTAAGGCCAGAAGCACACCAGTCACACTAAGCAAA
GATCAACTGAGTGGTATAAATAATATTGCATTTAGTAACTAAATAAAAATAGCACCTAATCATGTTCTTACAATGGT
TTACTATCTGCTCATAGACAACCCATCTGTCATTGGATTTTCTTAAAATCTGAACTTCATCGAAACTCTCATCTATAA
ACCATCTCACTTACACTATTTAAGTAGATTCCTAGTTTATAGTTATATAAAACACAATTGCATGCCAGATTAACTTAC
CATCTGTAAAAATGAAAACTGGGGCAAACATGTCGCGAAGGAATCCTTGCAAATTTGAAATTCGAGGTCATTGCTT
AAATGGTAAGAGGTGTCATTTTAGTCATAATTATTTTGAATGGCCACCCCATGCACTGCTTGTAAGACAAAACTTTA
TGTTAAACAGAATACTTAAGTCTATGGATAAAAGTATAGATACCTTATCAGAAATAAGTGGAGCTGCAGAGTTGG
ACAGAACAGAAGAGTATGCTCTTGGTGTAGTTGGAGTGCTAGAGAGTTATATAGGATCAATAAACAATATAACTA
AACAATCAGCATGTGTTGCCATGAGCAAACTCCTCACTGAACTCAATAGTGATGATATCAAAAGCTGAGGGACA
ATGAAGAGCTAAATTCACCCAAGATAAGAGTGTACAATACTGTCATATCATATATTGAAAGCAACAGGAAAAACA
ATAAACAAACTATCCATCTGTTAAAAAGATTGCCAGCAGACGTATTGAAGAAAACCATCAAAAACACATTGGATAT
CCATAAGAGCATAACCATCAACAACCCAAAAGAATCAACTGTTAGTGATACAAATGACCATGCCAAAAATAATGAT
ACTACCTGACAAATATCCTTGTAGTATAACTTCCATACTAATAACAAGTAGATGTAGAGTTACTATGTATAATCAAA
AGAACACACTATATTTCAATCAAAACAACCCAAATAACCATATGTACTCACCGAATCAAACATTCAATGAAATCCAT
TGGACCTCTCAAGAATTGATTGACACAATTCAAAATTTTCTACAACATCTAGGTATTATTGAGGATATATATACAAT
ATATATATTAGTGTCATAACACTCAATTCTAACACTCACCACATCGTTACATTATTAATTCAAACAATTCAAGTTGTG
GGACAAAATGGATCCCATTATTAATGGAAATTCTGCTAATGTTTATCTAACCGATAGTTATTTAAAAGGTGTTATCT
CTTTCTCAGAGTGTAATGCTTTAGGAAGTTACATATTCAATGGTCCTTATCTCAAAAATGATTATACCAACTTAATTA
GTAGACAAAATCCATTAATAGAACACATGAATCTAAAGAAACTAAATATAACACAGTCCTTAATATCTAAGTATCAT
AAAGGTGAAATAAAATTAGAAGAACCTACTTATTTTCAGTCATTACTTATGACATACAAGAGTATGACCTCGTCAG
AACAGATTGCTACCACTAATTTACTTAAAAAGATAATAAGAAGAGCTATAGAAATAAGTGATGTCAAAGTCTATGC
TATATTGAATAAACTAGGGCTTAAAGAAAAGGACAAGATTAAATCCAACAATGGACAAGATGAAGACAACTCAGT
TATTACGACCATAATCAAAGATGATATACTTTCAGCTGTTAAAGATAATCAATCTCATCTTAAAGCAGACAAAAATC
ACTCTACAAAACAAAAAGACACAATCAAAACAACACTCTTGAAGAAATTGATGTGTTCAATGCAACATCCTCCATC
ATGGTTAATACATTGGTTTAACTTATACACAAAATTAAACAACATATTAACACAGTATCGATCAAATGAGGTAAAA
AACCATGGGTTTACATTGATAGATAATCAAACTCTTAGTGGATTTCAATTTATTTTGAACCAATATGGTTGTATAGT
TTATCATAAGGAACTCAAAAGAATTACTGTGACAACCTATAATCAATTCTTGACATGGAAAGATATTAGCCTTAGTA
GATTAAATGTTTGTTTAATTACATGGATTAGTAACTGCTTGAACACATTAAATAAAAGCTTAGGCCTAAGGTGCGG
ATTCAATAATGTTATCTTGACACAACTATTCCTTTATGGAGATTACATACTAAAGCTATTTCACAATGAGGGGTTCT
ACATAATAAAAGAGGTAGAGGGATTTATTATGTCTCTAATTTTAAATATAACAGAAGAAGATCAATTCAGAAAACG
ATTTTATAATAGTATGCTCAACAACATCACAGATGCTGCTAATAAAGCTCAGAAAAATCTGCTATCAAGAGTATGTC
ATACATTATTAGATAAGACAGTGTCCGATAATATAATAAATGGCAGATGGATAATTCTATTAAGTAAGTTCCTTAAA
```

```
TTAATTAAGCTTGCAGGTGACAATAACCTTAACAATCTGAGTGAACTATATTTTTTGTTCAGAATATTTGGACACCC
AATGGTAGATGAAAGACAAGCCATGGATGCTGTTAAAATTAATTGCAATGAGACCAAATTTTACTTGTTAAGCAGT
CTGAGTATGTTAAGAGGTGCCTTTATATATAGAATTATAAAAGGGTTTGTAAATAATTACAACAGATGGCCTACTTT
AAGAAATGCTATTGTTTTACCCTTAAGATGGTTAACTTACTATAAACTAAACACTTATCCTTCTTTGTTGGAACTTAC
AGAAAGAGATTTGATTGTGTTATCAGGACTACGTTTCTATCGTGAGTTTCGGTTGCCTAAAAAAGTGGATCTTGAA
ATGATTATAAATGATAAAGCTATATCACCTCCTAAAAATTTGATATGGACTAGTTTCCCTAGAAATTACATGCCATC
ACACATACAAAACTATATAGAACATGAAAAATTAAAATTTTCCGAGAGTGATAAATCAAGAAGAGTATTAGAGTAT
TATTTAAGAGATAACAAATTCAATGAATGTGATTTATACAACTGTGTAGTTAATCAAAGTTATCTCAACAACCCTAA
TCATGTGGTATCATTGACAGGCAAAGAAAGAGAACTCAGTGTAGGTAGAATGTTTGCAATGCAACCGGGAATGTT
CAGACAGGTTCAAATATTGGCAGAGAAAATGATAGCTGAAAACATTTTACAATTCTTTCCTGAAAGTCTTACAAGA
TATGGTGATCTAGAACTACAAAAAATATTAGAACTGAAAGCAGGAATAAGTAACAAATCAAATCGCTACAATGAT
AATTACAACAATTACATTAGTAAGTGCTCTATCATCACAGATCTCAGCAAATTCAATCAAGCATTTCGATATGAAAC
GTCATGTATTTGTAGTGATGTGCTGGATGAACTGCATGGTGTACAATCTCTATTTTCCTGGTTACATTTAACTATTCC
TCATGTCACAATAATATGCACATATAGGCATGCACCCCCCTATATAGGAGATCATATTGTAGATCTTAACAATGTAG
ATGAACAAAGTGGATTATATAGATATCACATGGGTGGCATCGAAGGGTGGTGTCAAAAACTATGGACCATAGAAG
CTATATCACTATTGGATCTAATATCTCTCAAAGGGAAATTCTCAATTACTGCTTTAATTAATGGTGACAATCAATCAA
TAGATATAAGCAAACCAATCAGACTCATGGAAGGTCAAACGCATGCTCTGGCAGATTATTTGCTAGCATTAAATAG
CCTTAAATTACTGTATAAAGAGTATGCAGGCATAGGCCACAAATTAAAAGGAACTGAGACTTATATATCACGAGAT
ATGCAATTTATGAGTAAAACAATTCAACATAACGGTGTATATTACCCAGCTAGTATAAAGAAAGTCCTAAGAGTGG
GACCGTGGATAAACACTATACTTGATGATTTCAAAGTGAGTCTAGAATCTATAGGTAGTTTGACACAAGAATTAGA
ATATAGAGGTGAAAGTCTATTATGCAGTTTAATATTTAGAAATGTATGGTTATATAATCAGATTGCTCTACAATTAA
AAAATCATGCATTATGTAACAATAAACTATATTTGGACATATTAAAGGTTCTGAAACACTTAAAAACCTTTTTTAATC
TTGATAATATTGATACAGCATTAACATTGTATATGAATTTACCCATGTTATTTGGTGGTGGTGATCCCAACTTGTTAT
ATCGAAGTTTCTATAGAAGAACTCCTGACTTCCTCACAGAGGCTATAGTTCACTCTGTGTTCATACTTAGTTATTATA
CAAACCATGACTTAAAAGATAAACTTCAAGATCTGTCAGATGATAGATTGAATAAGTTCTTAACATGCATAATCAC
GTTTGACAAAAACCCTAATGCTGAATTCGTAACATTGATGAGAGATCCTCAAGCTTTAGGGTCTGAGAGACAAGCT
AAAATTACTAGCGAAATCAATAGACTGGCAGTTACAGAGGTTTTGAGTACAGCTCCAAACAAAATATTCTCCAAAA
GTGCACAACATTATACTACTACAGAGATAGATCTAAATGATATTATGCAAAATATAGAACCTACGTATCCTCATGG
GCTAAGAGTTGTTTATGAAAGTTTACCCTTTTATAAAGCAGAGAAAATAGTAAATCTTATATCAGGTACAAAATCTA
TAACTAACATACTGGAAAAAACTTCTGCCATAGACTTAACAGATATTGATAGAGCCACTGAGATGATGAGGAAAA
ACATAACTTTGCTTATAAGGATACTTCCACTCGAGTGTAACAGAGATAAAAGAGAGATATTGAGTATGGAAAACCT
AAGTATTACTGAATTAAGCAAATATGTTAGGGAAAGATCTTGGTCTTTATCCAATATAGTTGGTGTTACATCACCCA
GTATCATGTATACAATGGACATCAAATATACTACAAGCACTATATCTAGTGGCATAATTATAGAGAAATATAATGTT
AACAGTTTAACACGTGGTGAGAGAGGACCCACTAAACCATGGGTTGGTTCATCTACACAAGAGAAAAAAACAATG
CCAGTTTATAATAGACAAGTCTTAACCAAAAAACAGAGAGATCAAATAGATCTATTAGCAAAATTGGATTGGGTGT
ATGCATCTATAGATAACAAGGATGAATTCATGGAAGAACTCAGCATAGGAACCCTTGGGCTAACAAATGAAAAGG
CCAAGAAATTATTTCCACAATATTTAAGTGTCAATTATTTGCATCGCCTTACAGTCAGTAGTAGACCATGTGAATTC
CCTGCATCAATACCAGCTTATAGAACAACAAATTATCACTTTGACACTAGCCCTATTAATCGCATATTAACAGAAAA
GTATGGTGATGAAGATATTGACATAGTATTCCAAAACTGTATAAGCTTTGGCCTTAGTTTAATGTCAGTAGTAGAA
CAATTTACTAATGTATGTCCTAACAGAATTATTCTCATACCTAAGCTTAATGAGATACATTTGATGAAACCTCCCATA
```

```
TTCACAGGTGATGTTGATATTCACAAGTTAAAACAAGTGATACAAAAACAGCATATGTTTTTACCAGACAAAATAA
GTTTGACTCAATATGTGGAATTATTCTTAAGTAATAAAACACTCAAATCTGGATCTCATGTTAATTCTAATTTAATAT
TGGCACATAAAATATCTGACTATTTTCATAATACTTACATTTTAAGTACTAATTTAGCTGGACATTGGATTCTGATTA
TACAACTTATGAAAGATTCTAAAGGTATTTTTGAAAAAGATTGGGGAGAGGGATATATAACTGATCATATGTTTAT
TAATTTGAAAGTTTTCTTCAATGCTTATAAGACCTATCTCTTGTGTTTTCATAAAGGTTATGGCAAAGCAAAGCTGG
AGTGTGATATGAACACTTCAGATCTTCTATGTGTATTGGAATTAATAGACAGTAGTTATTGGAAGTCTATGTCTAAG
GTATTTTTAGAACAAAAAGTTATCAAATACATTCTTAGCCAAGATGCAAGTTTACATAGAGTAAAAGGATGTCATA
GCTTCAAATTATGGTTTCTTAAACGTTTAAACGTAGCAGAATTCACAGTTTGCCCTTGGGTTGTTAACATAGATTAT
CATCCAACACATATGAAAGCAATATTAACTTATATAGATCTTGTTAGAATGGGATTGATAAATATAGATAGAATAC
ACATTAAAAATAAACACAAATTCAATGATGAATTTTATACTTCTAATCTCTTCTACATTAATTATAACTTCTCAGATA
ATACTCATCTGTTAACTAAATACATAAGGATTGCTAATTCTGAATTAGAAAATAATTACAACAAATTATATCATCCTA
CACCAGAAACCCTAGAGAATATACTAGCCAATCCGATTAAAAGTAATGACAAAAAGACACTGAATGACTATTGTAT
AGGTAAAAATGTTGACTCAATAATGTTACCATTGTTATCTAATAAGAAGCTTATTAAATCGTCTGCAATGATTAGAA
CCAATTACAGCAAACAAGATTTGTATAATTTATTCCCTATGGTTGTGATTGATAGAATTATAGATCATTCAGGCAAT
ACAGCCAAATCCAACCAACTTTACACTACTACTTCCCACCAAATATCCTTAGTGCACAATAGCACATCACTTTACTGC
ATGCTTCCTTGGCATCATATTAATAGATTCAATTTTGTATTTAGTTCTACAGGTTGTAAAATTAGTATAGAGTATATT
TTAAAAGATCTTAAAATTAAAGATCCCAATTGTATAGCATTCATAGGTGAAGGAGCAGGGAATTTATTATTGCGGA
CCGTAGTGGAACTTCATCCTGACATAAGATATATTTACAGAAGTCTGAAAGATTGCAATGATCATAGTTTACCTATT
GAGTTTTTAAGGCTGTACAATGGACATATCAACATTGATTATGGTGAAAATTTGACCATTCCTGCTACAGATGCAA
CCAACAACATTCATTGGTCTTATTTACATATAAAGTTTGCTGAACCTATCAGTCTTTTTGTCTGTGATGCCGAATTGT
CGGTAACCGTCAACTGGAGTAAAATTATAATAGAATGGAGCAAGCATGTAAGAAAGTGCAAGTACTGTTCCTCAG
TTAATAAATGTATGTTAATAGTAAAATATCATGCTCAAGATGATATTGATTTCAAATTAGACAATATAACTATATTA
AAAACTTACGTATGCTTAGGCAGTAAGTTAAAGGGATCGGAGGTTTACTTAGTCCTTACAATAGGTCCTGCGAATA
TATTCCCAGTATTTAATGTAGTACAAAATGCTAAATTGATACTATCAAGAACCAAAAATTTCATCATGCCTAAGAAA
GCTGATAAAGAGTCTATTGATGCAAATATTAAAAGTTTGATACCCTTTCTTTGTTACCCTATAACAAAAAAAGGAAT
TAATACTGCATTGTCAAAACTAAAGAGTGTTGTTAGTGGAGATATACTATCATATTCTATAGCTGGACGTAATGAA
GTTTTCAGCAATAAACTTATAAATCATAAGCATATGAACATCTTAAAATGGTTCAATCATGTTTTAAATTTCAGATCA
ACAGAACTAAACTATAACCATTTATATATGGTAGAATCTACATATCCTTACCTAAGTGAATTGTTAAACAGCTTGAC
AACCAATGAACTTAAAAAACTGATTAAAATCACAGGTAGTCTGTTATACAACTTTCATAATGAATAATGAATAAAG
ATCTTATAATAAAAATTCCCATAGCTATACACTAACACTGTATTCAATTATAGTTATTAAAAATTAAAAATCATATAA
TTTTTTAAATAACTTTTAGTGAACTAATCCTAAAGTTATCATTTTAATCTTGGAGGAATAAATTTAAACCCTAATCTA
ATTGGTTTATATGTGTATTAACTAAATTACGAGATATTAGTTTTTGACACTTTTTTTCTCGT
```

FIG. 7 – CONTINUED

SEQUENCE LISTING

<160> NUMBER OF SEQ ID NOS: 2

<210> SEQ ID NO 1
<211> LENGTH: 14988
<212> TYPE: DNA
<213> ORGANISM: Artificial Sequence
<220> FEATURE:
<223> OTHER INFORMATION: MEDI RSV DM2-2

<400> SEQUENCE: 1

```
acgggaaaaa atgcgtacaa caaacttgca taaaccaaaa aaatgggca aataagaatt      60
tgataagtac cacttaaatt taactcccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taacggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaga    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
```

-continued

```
aattatagta atttaaaatt aaggagagat ataagataga agatggggca aatacaaaga    1140
tggctcttag caaagtcaag ttgaatgata cactcaacaa ggatcaactt ctgtcatcca    1200
gcaaatacgc catccaacgg agcacaggag atagtattga tactcctaat tatgatgtgc    1260
agaaacacat caataagtta tgtggcatgt tattaatcac agaagatgct aatcataaat    1320
tcactgggtt aataggtatg ttatatgcga tgtctaggtt aggaagagaa gacaccataa    1380
aaatactcag agatgcggga tatcatgtaa aagcaaatgg agtagatgta acaacacatc    1440
gtcaagacat taatggaaaa gaaatgaaat tgaagtgtt aacattggca agcttaacaa     1500
ctgaaattca aatcaacatt gagatagaat ctagaaaatc ctacaaaaaa atgctaaaag    1560
aaatgggaga ggtagctcca gaatacaggc atgactctcc tgattgtggg atgataatat    1620
tatgtatagc agcattagta ataactaaat tagcagcagg ggacagatct ggtcttacag    1680
ccgtgattag gagagctaat aatgtcctaa aaatgaaat gaaacgttac aaaggcttac     1740
tacccaagga catagccaac agcttctatg aagtgtttga aaaacatccc cactttatag    1800 atgttttgt tcattttggt atagcacaat cttctaccag aggtggcagt agagttgaag     1860 ggattttgc aggattgttt atgaatgcct atggtgcagg gcaagtgatg ttacggtggg     1920
gagtcttagc aaaatcagtt aaaaatatta tgttaggaca tgctagtgtg caagcagaaa    1980
tggaacaagt tgttgaggtt tatgaatatg cccaaaaatt gggtggtgaa gcaggattct    2040
accatatatt gaacaaccca aaagcatcat tattatcttt gactcaattt cctcacttct    2100
ccagtgtagt attaggcaat gctgctggcc taggcataat gggagagtac agaggtacac    2160
cgaggaatca agatctatat gatgcagcaa aggcatatgc tgaacaactc aaagaaaatg    2220
gtgtgattaa ctacagtgta ctagacttga cagcagaaga actagaggct atcaaacatc    2280
agcttaatcc aaaagataat gatgtagagc tttgagttaa taaaaatgg ggcaaataaa     2340 tcatcatgga aaagtttgct cctgaattcc atggagaaga tgcaaacaac agggctacta    2400
aattcctaga atcaataaag ggcaaattca catcacccaa agatcccaag aaaaagata     2460 gtatcatatc tgtcaactca atagatatag aagtaaccaa agaaagccct ataacatcaa    2520
attcaactat tatcaaccca acaaatgaga cagatgatac tgcagggaac aagcccaatt    2580
atcaaagaaa acctctagta agtttcaaag aagaccctac accaagtgat aatcccttt     2640 ctaaactata caaagaaacc atagaaacat ttgataacaa tgaagaagaa tccagctatt    2700
catacgaaga aataaatgat cagacaaacg ataatataac agcaagatta gataggattg    2760
atgaaaaatt aagtgaaata ctaggaatgc ttcacacatt agtagtggca agtgcaggac    2820
ctacatctgc tcgggatggt ataagagatg ccatggttgg tttaagagaa gaatgataga    2880 aaaaatcag aactgaagca ttaatgacca atgacagatt agaagctatg gcaagactca    2940
ggaatgagga agtgaaaag atggcaaaag acacatcaga tgaagtgtct ctcaatccaa     3000
catcagagaa attgaacaac ctattggaag ggaatgatag tgacaatgat ctatcacttg    3060
aagatttctg attagttacc aatcttcaca tcaacacaca ataccaacag aagaccaaca    3120
aactaaccaa cccaatcatc caaccaaaca tccatccgcc aatcagccaa acagccaaca    3180
aaacaaccag ccaatccaaa actaaccacc cggaaaaaat ctataatata gttacaaaaa    3240
aaggaagggg tggggcaaat atggaaacat acgtgaacaa gcttcacgaa ggctccacat    3300
acacagctgc tgttcaatac aatgtcttag aaaagacga tgaccctgca tcacttacaa    3360
tatgggtgcc catgttccaa tcatctatgc cagcagattt acttataaaa gaactagcta    3420
atgtcaacat actagtgaaa caaatatcca cacccaaggg accttcacta agagtcatga    3480
```

```
taaactcaag aagtgcagtg ctagcacaaa tgcccagcaa atttaccata tgcgctaatg    3540
tgtccttgga tgaaagaagc aaactagcat atgatgtaac cacaccctgt gaaatcaagg    3600
catgtagtct aacatgccta aaatcaaaaa atatgttgac tacagttaaa gatctcacta    3660
tgaagacact caaccctaca catgatatta ttgctttatg tgaatttgaa acatagtaa     3720 catcaaaaaa agtcataata ccaacatacc taagatccat cagtgtcaga ataaagatc     3780 tgaacacact tgaaaatata acaaccactg aattcaaaaa tgctatcaca aatgcaaaaa    3840 tcatcccctta ctcaggatta ctattagtca tcacagtgac tgacaacaaa ggagcattca   3900
aatacataaa gccacaaagt caattcatag tagatcttgg agcttaccta gaaaaagaaa    3960
gtatatatta tgttaccaca aattggaagc acacagctac acgatttgca atcaaaccca    4020
tggaagatta acctttttcc tctacatcag tgtgttaatt catacaaact ttctacctac    4080
attcttcact tcaccatcac aatcacaaac actctgtggt tcaaccaatc aaacaaaact    4140
tatctgaagt cccagatcat cccaagtcat tgtttatcag atctagtact caaataagtt    4200 aataaaaat atacacatgg ggcaaataat cattggagga aatccaacta atcacaatat     4260
ctgttaacat agacaagtcc acacaccata cagaatcaac caatggaaaa tacatccata    4320
acaatagaat tctcaagcaa attctggcct tactttacac taatacacat gatcacaaca    4380
ataatctctt tgctaatcat aatctccatc atgattgcaa tactaaacaa actttgtgaa    4440
tataacgtat tccataacaa aacctttgag ttaccaagag ctcgagtcaa cacatagcat    4500
tcatcaatcc aacagcccaa aacagtaacc ttgcatttaa aaatgaacaa cccctacctc    4560
tttacaacac ctcattaaca tcccaccatg caaaccacta tccatactat aaagtagtta    4620
attaaaaata gtcataacaa tgaactagga tatcaagact aacaataaca ttggggcaaa    4680
tgcaaacatg tccaaaaaca aggaccaacg caccgctaag acattagaaa ggacctggga    4740
cactctcaat catttattat tcatatcatc gtgcttatat aagttaaatc ttaaatctgt    4800
agcacaaatc acattatcca ttctggcaat gataatctca acttcactta taattgcagc    4860
catcatattc atagcctcgg caaaccacaa agtcacacca acaactgcaa tcatacaaga    4920
tgcaacaagc cagatcaaga acacaacccc aacatacctc acccagaatc ctcagcttgg    4980
aatcagtccc tctaatccgt ctgaaattac atcacaaatc accaccatac tagcttcaac    5040
aacaccagga gtcaagtcaa ccctgcaatc cacaacagtc aagaccaaaa acacaacaac    5100
aactcaaaca caacccagca agcccaccac aaaacaacgc caaaacaaac caccaagcaa    5160
acccaataat gattttcact ttgaagtgtt caactttgta ccctgcagca tatgcagcaa    5220
caatccaacc tgctgggcta tctgcaaaag aataccaaac aaaaaccag gaaagaaaac    5280 cactaccaag cccacaaaaa aaccaaccct caagacaacc aaaaagatc ccaaacctca     5340 aaccactaaa tcaaaggaag tacccaccac caagcccaca gaagagccaa ccatcaacac    5400
caccaaaaca aacatcataa ctacactact cacctccaac accacaggaa atccagaact    5460
cacaagtcaa atggaaaacct tccactcaac ttcctccgaa ggcaatccaa gcccttctca   5520
agtctctaca acatccgagt acccatcaca accttcatct ccacccaaca caccacgcca    5580
gtagttactt aaaaacatat tatcacaaaa agccatgacc aacttaaaca gaatcaaagt    5640
aaactctggg gcaaataaca atggagttgc taatcctcaa agcaaatgca attaccacaa    5700
tcctcactgc agtcacattt tgttttgctt ctggtcaaaa catcactgaa gaattttatc    5760
aatcaacatg cagtgcagtt agcaaaggct atcttagtgc tctgagaact ggttggtata    5820
```

```
ccagtgttat aactatagaa ttaagtaata tcaagaaaaa taagtgtaat ggaacagatg    5880
ctaaggtaaa attgataaaa caagaattag ataaatataa aaatgctgta acagaattgc    5940
agttgctcat gcaaagcaca caagcaacaa acaatcgagc cagaagagaa ctaccaaggt    6000
ttatgaatta tacactcaac aatgccaaaa aaccaatgt aacattaagc aagaaaagga     6060
aaagaagatt tcttggtttt tgttaggtg ttggatctgc aatcgccagt ggcgttgctg      6120
tatctaaggt cctgcaccta aaggggaag tgaacaagat caaaagtgct ctactatcca     6180
caaacaaggc tgtagtcagc ttatcaaatg gagtcagtgt cttaaccagc aaagtgttag    6240
acctcaaaaa ctatatagat aaacaattgt tacctattgt gaacaagcaa agctgcagca    6300
tatcaaatat agaaactgtg atagagttcc aacaaaagaa caacagacta ctagagatta    6360
ccagggaatt tagtgttaat gcaggtgtaa ctacacctgt aagcacttac atgttaacta    6420
atagtgaatt attgtcatta atcaatgata tgcctataac aaatgatcag aaaaagttaa    6480
tgtccaacaa tgttcaaata gttagacagc aaagttactc tatcatgtcc ataataaaag    6540
aggaagtctt agcatatgta gtacaattac cactatatgg tgttatagat acaccctgtt    6600
ggaaactaca cacatcccct ctatgtacaa ccaacacaaa agaagggtcc aacatctgtt    6660
taacaagaac tgacagagga tggtactgtg acaatgcagg atcagtatct ttcttcccac    6720
aagctgaaac atgtaaagtt caatcaaatc gagtattttg tgacacaatg aacagtttaa    6780
cattaccaag tgaagtaaat ctctgcaatg ttgacatatt caaccccaaa tatgattgta    6840
aaattatgac ttcaaaaaca gatgtaagca gctccgttat cacatctcta ggagccattg    6900
tgtcatgcta tggcaaaact aaatgtacag catccaataa aaatcgtgga atcataaaga    6960
cattttctaa cgggtgcgat tatgtatcaa ataaggggt ggacactgtg tctgtaggta     7020
acacattata ttatgtaaat aagcaagaag gtaaaagtct ctatgtaaaa ggtgaaccaa    7080
taataaattt ctatgaccca ttagtattcc cctctgatga atttgatgca tcaatatctc    7140
aagtcaacga gaagattaac cagagcctag catttattcg taaatccgat gaattattac    7200
ataatgtaaa tgccggtaaa tccaccacaa atatcatgat aactactata attatagtga    7260
ttatagtaat attgttatca ttaattgctg ttggactgct cttatactgt aaggccagaa    7320
gcacaccagt cacactaagc aaagatcaac tgagtggtat aaataatatt gcatttagta    7380
actaaataaa aatagcacct aatcatgttc ttacaatggt ttactatctg ctcatagaca    7440
acccatctgt cattggattt tcttaaaatc tgaacttcat tgaaactctc atctataaac    7500
catctcactt acactatttta agtagattcc tagtttatag ttatataaaa cacaattgaa    7560
tgccagatta acttaccatc tgtaaaaatg aaaactgggg caaatatgtc acgaaggaat    7620
ccttgcaaat ttgaaattcg aggtcattgc ttaaatggta agaggtgtca ttttagtcat    7680
aattattttg aatggccacc gcatgcactg cttgtaagac aaaactttat gttaaacaga    7740
atacttaagt ctatggataa aagtatagat accttatcag aaataagtgg agctgcagag    7800
ttggacagaa cagaagagta tgctcttggt gtagttggag tgctagagag ttatatagga    7860
tcaataaaca atataactaa acaatcagca tgtgttgcca tgagcaaact cctcactgaa    7920
ctcaatagtg atgatatcaa aaagctgagg gacaatgaag agctaaattc acccaagata    7980
agagtgtaca atactgtcat atcatatatt gaaagcaaca ggaaaaacaa taaacaaact    8040
atccatctgt taaaaagatt gccagcagac gtattgaaga aaccatcaa aaacacattg      8100 gatatccata gagcataac catcaacaac ccaaaagaat caactgttag tgatacaaat     8160
gaccatgcca aaaataatga tactacctga caaataagct tcaattctaa cactcaccac    8220
```

```
atcgttacat tattaattca aacaattcaa gttgtgggac aaaatggatc ccattattaa    8280
tggaaattct gctaatgttt atctaaccga tagttattta aaaggtgtta tctctttctc    8340
agagtgtaat gctttaggaa gttacatatt caatggtcct tatctcaaaa atgattatac    8400
caacttaatt agtagacaaa atccattaat agaacacatg aatctaaaga aactaaatat    8460
aacacagtcc ttaatatcta agtatcataa aggtgaaata aaattagaag aacctactta    8520
ttttcagtca ttacttatga catacaagag tatgacctcg tcagaacaga ttgctaccac    8580
taatttactt aaaaagataa taagaagagc tatagaaata agtgatgtca aagtctatgc    8640
tatattgaat aaactagggc ttaaagaaaa ggacaagatt aaatccaaca atggacaaga    8700
tgaagacaac tcagttatta cgaccataat caaagatgat atactttcag ctgttaaaga    8760
taatcaatct catcttaaag cagacaaaaa tcactctaca aaacaaaaag acacaatcaa    8820
aacaacactc ttgaagaaat tgatgtgttc aatgcaacat cctccatcat ggttaataca    8880
ttggtttaac ttatacacaa aattaaacaa catattaaca cagtatcgat caaatgaggt    8940
aaaaaaccat gggtttacat tgatagataa tcaaactctt agtggatttc aatttatttt    9000
gaaccaatat ggttgtatag tttatcataa ggaactcaaa agaattactg tgacaaccta    9060
taatcaattc ttgacatgga aagatattag ccttagtaga ttaaatgttt gtttaattac    9120
atggattagt aactgcttga acacattaaa taaaagctta ggcttaagat gcggattcaa    9180
taatgttatc ttgacacaac tattcctttta tggagattgt atactaaagc tatttcacaa    9240
tgaggggttc tacataataa aagaggtaga gggatttatt atgtctctaa ttttaaaatat    9300 aacagaagaa gatcaattca gaaaacgatt ttataatagt atgctcaaca acatcacaga    9360
tgctgctaat aaagctcaga aaaatctgct atcaagagta tgtcatacat tattagataa    9420
gacagtgtcc gataatataa aaatggcag atggataatt ctattaagta agttccttaa    9480
attaattaag cttgcaggtg acaataacct taacaatctg agtgaactat attttttgtt    9540
cagaatattt ggacacccaa tggtagatga aagacaagcc atggatgctg ttaaaattaa    9600
ttgcaatgag accaaatttt acttgttaag cagtctgagt atgttaagag gtgcctttat    9660
atatagaatt ataaagggt ttgtaaataa ttacaacaga tggcctactt taagaaatgc    9720
tattgtttta cccttaagat ggttaactta ctataaacta aacacttatc cttctttgtt    9780
ggaacttaca gaaagagatt tgattgtgtt atcaggacta cgtttctatc gtgagtttcg    9840
gttgcctaaa aaagtggatc ttgaaatgat tataaatgat aaagctatat cacctcctaa    9900
aaatttgata tggactagtt tccctagaaa ttacatgcca tcacacatac aaaactatat    9960
agaacatgaa aaattaaaat tttccgagag tgataaatca agaagagtat tagagtatta    10020
tttaagagat aacaaattca atgaatgtga tttatacaac tgtgtagtta atcaaagtta    10080
tctcaacaac cctaatcatg tggtatcatt gacaggcaaa gaaagagaac tcagtgtagg    10140
tagaatgttt gcaatgcaac cgggaatgtt cagacaggtt caaatattgg cagagaaaat    10200
gatagctgaa aacatttac aattctttcc tgaaagtctt acaagatatg gtgatctaga    10260
actacaaaaa atattagaat tgaaagcagg aataagtaac aaatcaaatc gctacaatga    10320
taattacaac aattacatta gtaagtgctc tatcatcaca gatctcagca aattcaatca    10380
agcatttcga tatgaaacgt catgtatttg tagtgatgtg ctggatgaac tgcatggtgt    10440
acaatctcta tttttcctggt tacatttaac tattcctcat gtcacaataa tatgcacata    10500
taggcatgca cccccctata taggagatca tattgtagat cttaacaatg tagatgaaca    10560
```

-continued

```
aagtggatta tatagatatc acatgggtgg catcgaaggg tggtgtcaaa aactatggac    10620
catagaagct atatcactat tggatctaat atctctcaaa gggaaattct caattactgc    10680
tttaattaat ggtgacaatc aatcaataga tataagcaaa ccaatcagac tcatggaagg    10740
tcaaactcat gctcaagcag attatttgct agcattaaat agccttaaat tactgtataa    10800
agagtatgca ggcataggcc acaaattaaa aggaactgag acttatatat cacgagatat    10860
gcaatttatg agtaaaacaa ttcaacataa cggtgtatat tacccagcta gtataaagaa    10920
agtcctaaga gtgggaccgt ggataaacac tatacttgat gatttcaaag tgagtctaga    10980
atctataggt agtttgacac aagaattaga atatagaggt gaaagtctat tatgcagttt    11040
aatatttaga aatgtatggt tatataatca gattgctcta caattaaaaa atcatgcatt    11100
atgtaacaat aaactatatt tggacatatt aaaggttctg aaacacttaa aaacctttt    11160 taatcttgat aatattgata cagcattaac attgtatatg aatttaccca tgttatttgg    11220
tggtggtgat cccaacttgt tatatcgaag tttctataga agaactcctg acttcctcac    11280
agaggctata gttcactctg tgttcatact tagttattat acaaaccatg acttaaaaga    11340
taaacttcaa gatctgtcag atgatagatt gaataagttc ttaacatgca taatcacgtt    11400
tgacaaaaac cctaatgctg aattcgtaac attgatgaga gatcctcaag ctttagggtc    11460
tgagagacaa gctaaaatta ctagcgaaat caatagactg gcagttacag aggttttgag    11520
tacagctcca aacaaaatat tctccaaaag tgcacaacat tatactacta cagagataga    11580
tctaaatgat attatgcaaa atatagaacc tacatatcct catgggctaa gagttgttta    11640
tgaaagttta ccctttttata aagcagagaa aatagtaaat cttatatcag gtacaaaatc    11700
tataactaac atactggaaa aaacttctgc catagactta acagatattg atagagccac    11760
tgagatgatg aggaaaaaca taactttgct tataaggata cttccattgg attgtaacag    11820
agataaaaga gagatattga gtatggaaaa cctaagtatt actgaattaa gcaaatatgt    11880
tagggaaaga tcttggtctt tatccaatat agttggtgtt acatcaccca gtatcatgta    11940
tacaatggac atcaaatata ctacaagcac tatatctagt ggcataatta tagagaaata    12000
taatgttaac agtttaacac gtggtgagag aggaccccact aaaccatggg ttggttcatc    12060
tacacaagag aaaaaaacaa tgccagttta taatagacaa gtcttaacca aaaaacagag    12120
agatcaaata gatctattag caaaattgga ttgggtgtat gcatctatag ataacaagga    12180
tgaattcatg gaagaactca gcataggaac ccttgggtta acatatgaaa aggccaagaa    12240
attatttcca caatatttaa gtgtcaatta tttgcatcgc cttacagtca gtagtagacc    12300
atgtgaattc cctgcatcaa taccagctta tagaacaaca aattatcact ttgacactag    12360
ccctattaat cgcatattaa cagaaaagta tggtgatgaa gatattgaca tagtattcca    12420
aaactgtata agctttggcc ttagtttaat gtcagtagta gaacaattta ctaatgtatg    12480
tcctaacaga attattctca tacctaagct taatgagata catttgatga aacctcccat    12540
attcacaggt gatgttgata ttcacaagtt aaaacaagtg atacaaaaac agcatatgtt    12600
tttaccagac aaaataagtt tgactcaata tgtggaatta ttcttaagta ataaaacact    12660
caaatctgga tctcatgtta attctaattt aatattggca cataaaatat ctgactattt    12720
tcataatact tacattttaa gtactaattt agctggacat tggattctga ttatacaact    12780
tatgaaagat tctaaaggta tttttgaaaa agattgggga gagggatata taactgatca    12840
tatgtttatt aatttgaaag ttttcttcaa tgcttataag acctatctct gtgtttttca    12900
taaaggttat ggcaaagcaa agctggagtg tgatatgaac acttcagatc ttctatgtgt    12960
```

```
attggaatta atagacagta gttattggaa gtctatgtct aaggtatttt tagaacaaaa   13020
agttatcaaa tacattctta gccaagatgc aagtttacat agagtaaaag gatgtcatag   13080
cttcaaatta tggtttctta aacgtcttaa tgtagcagaa ttcacagttt gcccttgggt   13140
tgttaacata gattatcatc caacacatat gaaagcaata ttaacttata tagatcttgt   13200
tagaatggga ttgataaata tagatagaat acacattaaa ataaacaca aattcaatga    13260 tgaattttat acttctaatc tcttctacat taattataac ttctcagata atactcatct   13320
attaactaaa catataagga ttgctaattc tgaattagaa ataattaca acaaattata    13380 tcatcctaca ccagaaacac tagagaatat actagccaat ccgattaaaa gtaatgacaa   13440
aaagacactg aatgactatt gtataggtaa aaatgttgac tcaataatgt taccattgtt   13500
atctaataag aagcttatta aatcgtctgc aatgattaga accaattaca gcaaacaaga   13560
tttgtataat ttattcccta tggttgtgat tgatagaatt atagatcatt caggcaatac   13620
agccaaatcc aaccaacttt acactactac ttcccaccaa atatctttag tgcacaatag   13680
cacatcactt tactgcatgc ttccttggca tcatattaat agattcaatt ttgtatttag   13740
ttctacaggt tgtaaaatta gtatagagta tattttaaaa gatcttaaaa ttaaagatcc   13800
caattgtata gcattcatag gtgaaggagc agggaattta ttattgcgta cagtagtgga   13860
acttcatcct gacataagat atatttacag aagtctgaaa gattgcaatg atcatagttt   13920
acctattgag tttttaaggc tgtacaatgg acatatcaac attgattatg gtgaaaattt   13980
gaccattcct gctacagatg caaccaacaa cattcattgg tcttatttac atataaagtt   14040
tgctgaacct atcagtcttt ttgtctgtga tgccgaattg tctgtaacag tcaactggag   14100
taaaattata atagaatgga gcaagcatgt aagaaagtgc aagtactgtt cctcagttaa   14160
taaatgtatg ttaatagtaa aatatcatgc tcaagatgat attgatttca aattagacaa   14220
tataactata ttaaaaactt atgtatgctt aggcagtaag ttaaagggat cggaggttta   14280
cttagtcctt acaataggtc ctgcgaatat attcccagta tttaatgtag tacaaaatgc   14340
taaattgata ctatcaagaa ccaaaaattt catcatgcct aagaaagctg ataaagagtc   14400
tattgatgca aatattaaaa gtttgatacc ctttctttgt acccctataa caaaaaaagg   14460
aattaatact gcattgtcaa aactaaagag tgttgttagt ggagatatac tatcatattc   14520
tatagctgga cgtaatgaag ttttcagcaa taaacttata aatcataagc atatgaacat   14580
cttaaaatgg ttcaatcatg ttttaaattt cagatcaaca gaactaaact ataaccatt   14640 atatatggta gaatctacat atccttacct aagtgaattg ttaaacagct tgacaaccaa   14700
tgaacttaaa aaactgatta aaatcacagg tagtctgtta tacaactttc ataatgaata   14760
atgaataaag atcttataat aaaaattccc atagctatac actaacactg tattcaatta   14820
tagttattaa aaattaaaaa tcatataatt ttttaaataa cttttagtga actaatccta   14880
aagttatcat tttaatcttg gaggaataaa tttaaaccct aatctaattg gtttatatgt   14940
gtattaacta aattacgaga tattagtttt tgacactttt tttctcgt                14988
```

<210> SEQ ID NO 2
<211> LENGTH: 14804
<212> TYPE: DNA
<213> ORGANISM: Artificial Sequence
<220> FEATURE:
<223> OTHER INFORMATION: rA2 cp248/404/1030/deltaSH

<400> SEQUENCE: 2

```
acgggaaaaa atgcgtacaa caaacttgca taaaccaaaa aaatgggca  aataagaatt      60
tgataagtac cacttaaatt taactcccct ggttagagat gggcagcaat tcattgagta     120
tgataaaagt tagattacaa aatttgtttg acaatgatga agtagcattg ttaaaaataa     180
catgctatac tgataaatta atacatttaa ctaatgcttt ggctaaggca gtgatacata     240
caatcaaatt gaatggcatt gtgtttgtgc atgttattac aagtagtgat atttgcccta     300
ataataatat tgtagtaaaa tccaatttca caacaatgcc agtactacaa atggaggtt      360
atatatggga aatgatggaa ttaacacatt gctctcaacc taatggtcta ctagatgaca     420
attgtgaaat taaattctcc aaaaaactaa gtgattcaac aatgaccaat tatatgaatc     480
aattatctga attacttgga tttgatctta atccataaat tataattaat atcaactagc     540
aaatcaatgt cactaacacc attagttaat ataaaactta acagaagaca aaaatggggc     600
aaataaatca attcagccaa cccaaccatg gacacaaccc acaatgataa tacaccacaa     660
agactgatga tcacagacat gagaccgttg tcacttgaga ccataataac atcactaacc     720
agagacatca taacacacaa atttatatac ttgataaatc atgaatgcat agtgagaaaa     780
cttgatgaaa gacaggccac atttacattc ctggtcaact atgaaatgaa actattacac     840
aaagtaggaa gcactaaata taaaaaatat actgaataca acacaaaata tggcactttc     900
cctatgccaa tattcatcaa tcatgatggg ttcttagaat gcattggcat taagcctaca     960
aagcatactc ccataatata caagtatgat ctcaatccat aaatttcaac acaatattca    1020
cacaatctaa acaacaact  ctatgcataa ctatactcca tagtccagat ggagcctgaa    1080
aattatagta atttaaaact taaggagaga tataagatag aagatggggc aaatacaacc    1140
atggctctta gcaaagtcaa gttgaatgat acactcaaca agatcaact  tctgtcatcc    1200
agcaaataca ccatccaacg gagcacagga gatagtattg atactcctaa ttatgatgtg    1260
cagaaacaca tcaataagtt atgtggcatg ttattaatca cagaagatgc taatcataaa    1320
ttcactgggt taataggtat gttatatgcg atgtctaggt taggaagaga agacaccata    1380
aaaatactca gagatgcggg atatcatgta aaagcaaatg gagtagatgt aacaacacat    1440
cgtcaagaca ttaatggaaa agaaatgaaa tttgaagtgt taacattggc aagcttaaca    1500
actgaaattc aaatcaacat tgagataaa  tctagaaaat cctacaaaaa aatgctaaaa    1560
gaaatgggag aggtagctcc agaatacagg catgactctc ctgattgtgg gatgataata    1620
ttatgtatag cagcattagt aataactaaa ttagcagcag gggacagatc tggtcttaca    1680
gccgtgatta ggagagctaa taatgtccta aaaaatgaaa tgaaacgtta caaggctta    1740
ctacccaagg acatagccaa cagcttctat gaagtgtttg aaaaacatcc cactttata    1800
gatgtttttg ttcattttgg tatagcacaa tcttctacca gaggtggcag tagagttgaa    1860
gggattttg  caggattgtt tatgaatgcc tatggtgcag gcaagtgat  gttacggtgg    1920
ggagtcttag caaaatcgat taaaaatatt atgttaggac atgctagtgt gcaagcagaa    1980
atggaacaag ttgttgaggt ttatgaatat gcccaaaaat tgggtggtga agcaggattc    2040
taccatatat tgaacaaccc aaaagcatca ttattatctt tgactcaatt tcctcacttc    2100
tccagtgtag tattaggcaa tgctgctggc ctaggcataa tgggagagta cagaggtaca    2160
ccgaggaatc aagatctata tgatgcagca aaggcatatg ctgaacaact caaagaaaat    2220
ggtgtgatta actacagtgt actagacttg acagcagaag aactagaggc tatcaaacat    2280
```

```
cagcttaatc caaaagataa tgatgtagag ctttgagtta ataaaaaatg ggcaaataa    2340 atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca agaaagccc tataacatca    2520 aattcaacta ttatcaaccc aacaaatgag acagatgata ctgcagggaa caagcccaat   2580
tatcaaagaa aacctctagt aagtttcaaa gaagaccct accaagtga taatccttt     2640 tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga gaaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca acagccaac    3180 aaacaaccca gccaatccaa aactaaccac ccggaaaaaa tctataatat agttacaaaa   3240
aaaggaaagg gtgggggcaaa tatggaaaca tacgtgaaca agcttcacga aggtccaca   3300 tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaaattggaag cacacagcta cacgatttgc aatcaaaccc   4020
atggaagatt aaccttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taattaaaaa tagtcataac aatgaactag gatatcaaga ctaacaataa cattggggca   4260
aatgcaaaca tgtccaaaaa caaggaccaa cgcaccgcta agacattaga aaggacctgg   4320
gacactctca atcatttatt attcatatca tcgtgcttat ataagttaaa tcttaaatct   4380
gtagcacaaa tcacattatc cattctggca atgataatct caacttcact tataattgca   4440
gccatcatat tcatagcctc ggcaaaccac aaagtcacac caacaactgc aatcatacaa   4500
gatgcaacaa gccagatcaa gaacacaacc caacatacc tcacccagaa tcctcagctt   4560
ggaatcagtc cctctaatcc gtctgaaatt acatcacaaa tcaccaccat actagcttca   4620
acaacaccag gagtcaagtc aaccctgcaa tcccaaacag tcaagaccaa aaacacaaca   4680
```

```
acaactcaaa cacaacccag caagcccacc acaaaacaac gccaaaacaa accaccaagc    4740
aaacccaata atgattttca ctttgaagtg ttcaactttg taccctgcag catatgcagc    4800
aacaatccaa cctgctgggc tatctgcaaa agaataccaa acaaaaaacc aggaaagaaa    4860
accactacca agcccacaaa aaaaccaacc ctcaagacaa ccaaaaaaga tcccaaacct    4920
caaaccacta aatcaaagga agtacccacc accaagccca cagaagagcc aaccatcaac    4980
accaccaaaa caaacatcat aactacacta ctcacctcca acaccacagg aaatccagaa    5040
ctcacaagtc aaatggaaac cttccactca acttcctccg aaggcaatcc aagcccttct    5100
caagtctcta caacatccga gtacccatca caaccttcat ctccacccaa cacaccacgc    5160
cagtagttac ttaaaaacat attatcacaa aaggccttga ccaacttaaa cagaatcaaa    5220
ataaactctg gggcaaataa caatggagtt gctaatcctc aaagcaaatg caattaccac    5280
aatcctcact gcagtcacat tttgttttgc ttctggtcaa acatcactg  aagaattta    5340 tcaatcaaca tgcagtgcag ttagcaaagg ctatcttagt gctctgagaa ctggttggta    5400
taccagtgtt ataactatag aattaagtaa tattaaggaa aataagtgta atggaacaga    5460
tgctaaggta aaattgataa aacaagaatt agataaatat aaaaatgctg taacagaatt    5520
gcagttgctc atgcaaagta ctccagcaac aaacaatcga gccagaagag aactaccaag    5580
gtttatgaat tatacactca acaatgccaa aaaaaccaat gtaacattaa gcaagaaaag    5640
gaaaagaaga tttcttggtt ttttgttagg tgttggatct gcaatcgcca gtggcgttgc    5700
tgtatctaag gtcctgcacc tagaagggga agtgaacaag atcaaaagtg ctctactatc    5760
cacaaacaag gctgtagtca gcttatcaaa tggagttagt gttttaacca gcaaagtgtt    5820
agacctcaaa aactatatag ataaacaatt gttacctatt gtgaacaagc aaagctgcag    5880
catatcaaat atcgcgactg tgatagagtt ccaacaaaag aacaacagac tactagagat    5940
taccagggaa tttagtgtta atgcaggcgt aactacacct gtaagcactt acatgttaac    6000
taatagtgaa ttattgtcat taatcaatga tatgcctata acaaatgatc agaaaaagtt    6060
aatgtccaac aatgttcaaa tagttagaca gcaaagttac tctatcatgt ccataataaa    6120
agaggaagtc ttagcatatg tagtacaatt accactatat ggtgttatag atacaccctg    6180
ttggaaacta cacacatccc ctctatgtac aaccaacaca aaagaagggt ccaacatctg    6240
tttaacaaga actgacagag gatggtactg tgacaatgca ggatcagtat ctttcttccc    6300
acaagctgaa acatgtaaag ttcaatcaaa tcgagtattt tgtgacacaa tgaacagttt    6360
aacattacca agtgaagtaa atctctgcaa tgttgacata ttcaacccca aatatgattg    6420
taaaattatg acttcaaaaa cagatgtaag cagctccgtt atcacatctc taggagccat    6480
tgtgtcatgc tatggcaaaa ctaaatgtac agcatccaat aaaaatcgtg aatcataaa   6540 gacattttct aacgggtgcg attatgtatc aaataaaggg gtggacactg tgtctgtagg    6600
taacacatta tattatgtaa ataagcaaga aggtaaaagt ctctatgtaa aaggtgaacc    6660
aataataaat ttctatgacc cattagtatt cccctctgat gaatttgatg catcaatatc    6720
tcaagtcaac gagaagatta accagagcct agcatttatt cgtaaatccg atgaattatt    6780
acataatgta aatgctggta atccaccat  taatatcatg ataactacta aattatagt    6840 gattatagta atattgttat cattaattgc tgttggactg ctcttatact gtaaggccag    6900
aagcacacca gtcacactaa gcaaagatca actgagtggt ataaataata ttgcatttag    6960
taactaaata aaaatagcac ctaatcatgt tcttacaatg gtttactatc tgctcataga    7020
```

```
caacccatct gtcattggat tttcttaaaa tctgaacttc atcgaaactc tcatctataa    7080
accatctcac ttacactatt taagtagatt cctagtttat agttatataa aacacaattg    7140
catgccagat taacttacca tctgtaaaaa tgaaaactgg ggcaaacatg tcgcgaagga    7200
atccttgcaa atttgaaatt cgaggtcatt gcttaaatgg taagaggtgt cattttagtc    7260
ataattattt tgaatggcca ccccatgcac tgcttgtaag acaaaacttt atgttaaaca    7320
gaatacttaa gtctatggat aaaagtatag ataccttatc agaaataagt ggagctgcag    7380
agttggacag aacagaagag tatgctcttg gtgtagttgg agtgctagag agttatatag    7440
gatcaataaa caatataact aaacaatcag catgtgttgc catgagcaaa ctcctcactg    7500
aactcaatag tgatgatatc aaaaagctga gggacaatga agagctaaat tcacccaaga    7560
taagagtgta caatactgtc atatcatata ttgaaagcaa caggaaaaac aataaacaaa    7620
ctatccatct gttaaaaaga ttgccagcag acgtattgaa gaaaaccatc aaaaacacat    7680
tggatatcca taagagcata accatcaaca acccaaaaga atcaactgtt agtgatacaa    7740
atgaccatgc caaaaataat gatactacct gacaaatatc cttgtagtat aacttccata    7800
ctaataacaa gtagatgtag agttactatg tataatcaaa agaacacact atatttcaat    7860
caaaacaacc caaataacca tatgtactca ccgaatcaaa cattcaatga aatccattgg    7920
acctctcaag aattgattga cacaattcaa aattttctac aacatctagg tattattgag    7980
gatatatata caatatatat attagtgtca taacactcaa ttctaacact caccacatcg    8040
ttacattatt aattcaaaca attcaagttg tgggacaaaa tggatcccat tattaatgga    8100
aattctgcta atgtttatct aaccgatagt tatttaaaag gtgttatctc tttctcagag    8160
tgtaatgctt taggaagtta catattcaat ggtccttatc tcaaaaatga ttataccaac    8220
ttaattagta gacaaaatcc attaataaga cacatgaatc taaagaaact aaatataaca    8280
cagtccttaa tatctaagta tcataaaggt gaaataaaat tagaagaacc tacttatttt    8340
cagtcattac ttatgacata caagagtatg acctcgtcag aacagattgc taccactaat    8400
ttacttaaaa agataataag aagagctata gaaataagtg atgtcaaagt ctatgctata    8460
ttgaataaac tagggcttaa agaaaaggac aagattaaat ccaacaatgg acaagatgaa    8520
gacaactcag ttattacgac cataatcaaa gatgatatac tttcagctgt taaagataat    8580
caatctcatc ttaaagcaga caaaaatcac tctacaaaac aaaaagacac aatcaaaaca    8640
acactcttga agaaattgat gtgttcaatg caacatcctc catcatggtt aatacattgg    8700
tttaacttat acacaaaatt aaacaacata ttaacacagt atcgatcaaa tgaggtaaaa    8760
aaccatgggt ttacattgat agataatcaa actcttagtg gatttcaatt tattttgaac    8820
caatatggtt gtatagttta tcataaggaa ctcaaaagaa ttactgtgac aacctataat    8880
caattcttga catggaaaga tattagcctt agtagattaa atgtttgttt aattacatgg    8940
attagtaact gcttgaacac attaaataaa agcttaggcc taaggtgcgg attcaataat    9000
gttatcttga cacaactatt cctttatgga gattacatac taaagctatt tcacaatgag    9060
gggttctaca taataaaaga ggtagaggga tttattatgt ctctaatttt aaatataaca    9120
gaagaagatc aattcagaaa acgatttttat aatagtatgc tcaacaacat cacagatgct    9180
gctaataaag ctcagaaaaa tctgctatca agagtatgtc atacattatt agataagaca    9240
gtgtccgata atataataaa tggcagatgg ataattctat taagtaagtt ccttaaatta    9300
attaagcttg caggtgacaa taaccttaac aatctgagtg aactatattt tttgttcaga    9360
atatttggac acccaatggt agatgaaaga caagccatgg atgctgttaa aattaattgc    9420
```

```
aatgagacca aattttactt gttaagcagt ctgagtatgt taagaggtgc ctttatatat   9480
agaattataa aagggtttgt aaataattac aacagatggc ctactttaag aaatgctatt   9540
gttttaccct taagatggtt aacttactat aaactaaaca cttatccttc tttgttggaa   9600
cttacagaaa gagatttgat tgtgttatca ggactacgtt tctatcgtga gtttcggttg   9660
cctaaaaaag tggatcttga aatgattata aatgataaag ctatatcacc tcctaaaaat   9720
ttgatatgga ctagtttccc tagaaattac atgccatcac acatacaaaa ctatatagaa   9780
catgaaaaat taaaattttc cgagagtgat aaatcaagaa gagtattaga gtattattta   9840
agagataaca aattcaatga atgtgattta tacaactgtg tagttaatca aagttatctc   9900
aacaacccta atcatgtggt atcattgaca ggcaaagaaa gagaactcag tgtaggtaga   9960
atgtttgcaa tgcaaccggg aatgttcaga caggttcaaa tattggcaga gaaaatgata  10020
gctgaaaaca ttttacaatt cttccctgaa agtcttacaa gatatggtga tctagaacta  10080
caaaaaatat tagaactgaa agcaggaata agtaacaaat caaatcgcta caatgataat  10140
tacaacaatt acattagtaa gtgctctatc atcacagatc tcagcaaatt caatcaagca  10200
tttcgatatg aaacgtcatg tatttgtagt gatgtgctgg atgaactgca tggtgtacaa  10260
tctctatttt cctggttaca tttaactatt cctcatgtca caataatatg cacatatagg  10320
catgcacccc cctatatagg agatcatatt gtagatctta acaatgtaga tgaacaaagt  10380
ggattatata gatatcacat gggtggcatc gaagggtggt gtcaaaaact atggaccata  10440
gaagctatat cactattgga tctaatatct ctcaaaggga aattctcaat tactgcttta  10500
attaatggtg acaatcaatc aatagatata agcaaaccaa tcagactcat ggaaggtcaa  10560
acgcatgctc tggcagatta tttgctagca ttaaatagcc ttaaattact gtataaagag  10620
tatgcaggca taggccacaa attaaaagga actgagactt atatatcacg agatatgcaa  10680
tttatgagta aaacaattca acataacggt gtatattacc cagctagtat aaagaaagtc  10740
ctaagagtgg gaccgtggat aaacactata cttgatgatt tcaaagtgag tctagaatct  10800
ataggtagtt tgacacaaga attagaatat agaggtgaaa gtctattatg cagtttaata  10860
tttagaaatg tatggttata taatcagatt gctctacaat taaaaaatca tgcattatgt  10920
aacaataaac tatatttgga catattaaag gttctgaaac acttaaaaac ctttttttaat  10980 cttgataata ttgatacagc attaacattg tatatgaatt tacccatgtt atttggtggt  11040
ggtgatccca acttgttata tcgaagtttc tatagaagaa ctcctgactt cctcacagag  11100
gctatagttc actctgtgtt catacttagt tattatacaa accatgactt aaaagataaa  11160
cttcaagatc tgtcagatga tagattgaat aagttcttaa catgcataat cacgtttgac  11220
aaaaacccta atgctgaatt cgtaacattg atgagagatc ctcaagcttt agggtctgag  11280
agacaagcta aaattactag cgaaatcaat agactggcag ttacagaggt tttgagtaca  11340
gctccaaaca aaatattctc caaagtgca caacattata ctactacaga gatagatcta  11400
aatgatatta tgcaaaatat agaacctacg tatcctcatg gctaagagt tgtttatgaa  11460 agtttaccct tttataaagc agagaaaata gtaaatctta tatcaggtac aaaatctata  11520
actaacatac tggaaaaaac ttctgccata gacttaacag atattgatag agccactgag  11580
atgatgagga aaacataac tttgcttata aggatacttc cactcgagtg taacagagat  11640
aaaagagaga tattgagtat ggaaaaccta agtattactg aattaagcaa atatgttagg  11700
gaaagatctt ggtctttatc caatatagtt ggtgttacat cacccagtat catgtataca  11760
```

```
atggacatca aatatactac aagcactata tctagtggca taattataga gaaatataat    11820
gttaacagtt taacacgtgg tgagagagga cccactaaac catgggttgg ttcatctaca    11880
caagagaaaa aaacaatgcc agtttataat agacaagtct taaccaaaaa acagagagat    11940
caaatagatc tattagcaaa attggattgg gtgtatgcat ctatagataa caaggatgaa    12000
ttcatggaag aactcagcat aggaaccctt gggctaacaa atgaaaaggc caagaaatta    12060
tttccacaat atttaagtgt caattatttg catcgcctta cagtcagtag tagaccatgt    12120
gaattccctg catcaatacc agcttataga acaacaaatt atcactttga cactagccct    12180
attaatcgca tattaacaga aaagtatggt gatgaagata ttgacatagt attccaaaac    12240
tgtataagct ttggccttag tttaatgtca gtagtagaac aatttactaa tgtatgtcct    12300
aacagaatta ttctcatacc taagcttaat gagatacatt tgatgaaacc tcccatattc    12360
acaggtgatg ttgatattca caagttaaaa caagtgatac aaaaacagca tatgttttta    12420
ccagacaaaa taagtttgac tcaatatgtg gaattattct taagtaataa aacactcaaa    12480
tctggatctc atgttaattc taatttaata ttggcacata aaatatctga ctatttcat    12540 aatacttaca ttttaagtac taatttagct ggacattgga ttctgattat acaacttatg    12600
aaagattcta aaggtatttt tgaaaaagat tggggagagg gatatataac tgatcatatg    12660
tttattaatt tgaaagtttt cttcaatgct tataagacct atctcttgtg ttttcataaa    12720
ggttatggca aagcaaagct ggagtgtgat atgaacactt cagatcttct atgtgtattg    12780
gaattaatag acagtagtta ttggaagtct atgtctaagg tatttttaga acaaaaagtt    12840
atcaaataca ttcttagcca agatgcaagt ttacatagag taaaaggatg tcatagcttc    12900
aaattatggt ttcttaaacg tttaaacgta gcagaattca cagtttgccc ttgggttgtt    12960
aacatagatt atcatccaac acatatgaaa gcaatattaa cttatataga tcttgttaga    13020
atgggattga taaatataga tagaatacac attaaaaata acacaaatt caatgatgaa    13080 ttttatactt ctaatctctt ctacattaat tataacttct cagataatac tcatctgtta    13140
actaaataca taaggattgc taattctgaa ttagaaaata ttacaacaa attatatcat    13200 cctacaccag aaaccctaga gaatatacta gccaatccga ttaaaagtaa tgacaaaaag    13260
acactgaatg actattgtat aggtaaaaat gttgactcaa taatgttacc attgttatct    13320
aataagaagc ttattaaatc gtctgcaatg attagaacca attacagcaa acaagatttg    13380 tataattta tccctatggt tgtgattgat agaattatag atcattcagg caatacagcc    13440
aaatccaacc aactttacac tactacttcc caccaaatat ccttagtgca caatagcaca    13500
tcactttact gcatgcttcc ttggcatcat attaatagat tcaattttgt atttagttct    13560
acaggttgta aaattagtat agagtatatt ttaaagatc ttaaaattaa agatcccaat    13620
tgtatagcat tcataggtga aggagcaggg aatttattat tgcggaccgt agtggaactt    13680
catcctgaca aagatatat ttacagaagt ctgaaagatt gcaatgatca tagtttacct    13740
attgagtttt taaggctgta caatggacat atcaacattg attatggtga aaattgacc    13800 attcctgcta cagatgcaac caacaacatt cattggtctt atttacatat aaagtttgct    13860
gaacctatca gtctttttgt ctgtgatgcc gaattgtcgg taaccgtcaa ctggagtaaa    13920
attataatag aatggagcaa gcatgtaaga aagtgcaagt actgttcctc agttaataaa    13980
tgtatgttaa tagtaaaata tcatgctcaa gatgatattg atttcaaatt agacaatata    14040
actatattaa aaacttacgt atgcttaggc agtaagttaa agggatcgga ggtttactta    14100
gtccttacaa taggtcctgc gaatatattc ccagtattta atgtagtaca aaatgctaaa    14160
```

```
ttgatactat caagaaccaa aaatttcatc atgcctaaga aagctgataa agagtctatt    14220
gatgcaaata ttaaaagttt gatacccttt ctttgttacc ctataacaaa aaaaggaatt    14280
aatactgcat tgtcaaaact aaagagtgtt gttagtggag atatactatc atattctata    14340
gctggacgta atgaagtttt cagcaataaa cttataaatc ataagcatat gaacatctta    14400
aaatggttca atcatgtttt aaatttcaga tcaacagaac taaactataa ccatttatat    14460
atggtagaat ctacatatcc ttacctaagt gaattgttaa acagcttgac aaccaatgaa    14520
cttaaaaaac tgattaaaat cacaggtagt ctgttataca actttcataa tgaataatga    14580
ataaagatct tataataaaa attcccatag ctatacacta acactgtatt caattatagt    14640
tattaaaaat taaaaatcat ataattttt aaataacttt tagtgaacta atcctaaagt    14700
tatcatttta atcttggagg aataaattta aaccctaatc taattggttt atatgtgtat    14760
taactaaatt acgagatatt agtttttgac actttttttc tcgt                    14804
```

METHOD OF VACCINATION WITH AN ATTENUATED RSV VACCINE FORMULATION

CROSS REFERENCE TO RELATED APPLICATIONS

This application is a national stage application under 35 U.S.C. 371 and claims the benefit of PCT Application No. PCT/US2016/060672 having an international filing date of 4 Nov. 2016, which designated the United States, which PCT application claimed priority to U.S. Provisional Application Ser. No. 62/251,030, filed Nov. 4, 2015, U.S. Provisional Application Ser. No. 62/259,472, filed Nov. 24, 2015, and U.S. Provisional Application Ser. No. 62/263,405, filed Dec. 4, 2015, all of which are incorporated herein by reference in their entireties for all purposes.

GOVERNMENT RIGHTS

The Government of the United States has certain rights in this invention.

SEQUENCE LISTING

The instant application contains a Sequence Listing, created on Nov. 4, 2016, named 6137NIAID-57-PCT_Sequence_Listing_ST25.txt, which is being submitted electronically and is hereby incorporated by reference in its entirety. It is 39 kb in size.

TECHNICAL FIELD

The present invention generally relates to methods and compositions useful in vaccinating against respiratory syncytial virus (RSV).

BACKGROUND

Respiratory syncytial virus (RSV) is the most important viral cause of severe acute lower respiratory illness (LRI) in infants and children worldwide. In the United States, RSV is the leading cause of hospitalization in children less than 1 year of age and is associated with a considerable burden of emergency room and outpatient care, with 10% of children less than 5 years of age receiving medical attention for RSV associated illness each year. Globally, RSV has been estimated to cause >3.5 million hospitalizations and 66,000 to 199,000 deaths annually. The relative importance of RSV as a pulmonary pathogen has also increased because the use of vaccines to prevent bacterial pneumonias has become widespread RSV is a member of the Pneumoviridae family and, as such, is an enveloped virus that replicates in the cytoplasm and matures by budding at the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA that has two overlapping open reading frames (ORFs) encoding two separate proteins M2-1 and M2-2. The 11 RSV proteins are: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. Each gene is flanked by short conserved transcription signals called the gene-start (GS) signal, present on the upstream end of each gene and involved in initiating transcription of the respective gene, and the gene-end (GE) signal, present at the downstream end of each gene and involved in directing synthesis of a polyA tail followed by release of the mRNA.

The RSV F and G proteins are the only RSV proteins known to induce RSV neutralizing antibodies, and are the major protective antigens. The F protein generally is considered to be a more effective neutralization and protective antigen than the G protein. F also is relatively well-conserved among RSV strains, whereas the G protein can be substantially divergent. The divergence in G is a major factor in segregating RSV strains into two antigenic subgroups, A and B (~53% and ~90% amino acid sequence identity between the two subgroups for G and F, respectively).

Because of the substantial global impact of RSV, increased efforts are under way to develop RSV vaccines for use in infancy and early childhood. A live attenuated RSV vaccine would be an attractive strategy for immunization of children and infants. Live attenuated vaccines mimic a mild natural infection and induce durable cellular and humoral immune responses. Furthermore, administration of candidate live attenuated RSV vaccines is not associated with the vaccine-associated enhanced RSV disease that was observed in children who received formalin-inactivated RSV and that also appeared to be associated with administration of RSV subunit vaccines in experimental animals.

Efforts to develop live attenuated RSV vaccines have been underway since the 1970s. The process of attenuation has been challenging because conventional methods, such as passage of virus at suboptimal temperatures or in the presence of mutagens, are targeted imprecisely and are poorly controlled. In addition, clinical attenuation typically is based on restriction of replication, which decreases antigenic load and diminishes the immune response. In the past, achieving a balance between attenuation and immunogenicity has proved difficult: some live attenuated RSV vaccine candidates have been insufficiently attenuated, whereas others were highly attenuated but insufficiently immunogenic. In addition, some candidate vaccines have exhibited genetic instability, with a partial loss of attenuating mutations. Thus, a need exists in the art to provide improved methods of vaccination against RSV.

SUMMARY

In one embodiment of the invention, it includes a method of vaccinating a human subject against respiratory syncytial virus (RSV), comprising administering to the subject a composition comprising an RSV particle that comprises an RSV genome or antigenome, wherein the subject is less than about 24 months of age, wherein the composition is administered in a single dose, and wherein the RSV genome or antigenome comprises a functional deletion in the M2-2 ORF corresponding to a deletion of nucleotides 8201-8434 in Genbank Accession No. M74568; and optionally comprises a characteristic selected from the group consisting of: (i) presence of one or more of, corresponding to the nucleotides in Genbank Accession No. M74568, C4488 in the SH gene, C4491 in the SH gene, A4494 in the SH gene, A4496 in the SH gene, G4497 in the SH gene, and a nucleotide sequence corresponding to nucleotides 4498-4609 in the non-translated region of the SH gene; (ii) presence of G at a nucleotide position corresponding to position 1209 in Genbank Accession No. M74568 encoding an Alanine at position 24 in the N protein; (iii) presence of G at a nucleotide position corresponding to position 779 in Genbank Accession No. M74568 encoding an Arginine at position 51 in the NS2 protein; (iv) presence of one or more nucleotides corresponding to the nucleotides in Genbank Accession No. M74568 selected from the group consisting of: A1138, G1139, A5611, A5615, G5639, T7481 and A7559; (v) presence of one or more nucleotides corresponding to the nucleotides in Genbank Accession No. M74568 selected from the group consisting of: C404 in the NSI gene, G1181 in the N gene, A1937 in the N gene, C6215 in the F gene, C6221 in the F gene, T6386 in the F gene, C7214 in the F gene, G7701 in the M2 gene; T8160 in the M2-2 gene, T8166 in the M2-2 gene, T8178 in the M2-2 gene, A8197 in the M2-2 gene, G8198 in the M2-2 gene, T 10514 in the L gene, A 13633 in the L gene, and T 13900 in the L gene; (vi) presence of T at a nucleotide position corresponding to position 1099 in Genbank Accession No. M74568; and (vii) a combination of the above.

In some embodiments, the single dose of the composition comprises about $10^{3.0}$ to about $10^{7.0}$ plaque-forming units (PFU) of RSV particles. In some embodiments, the single dose of the composition comprises about $10^{4.0}$ to about $10^{6.0}$ plaque-forming units (PFU) of RSV particles. In some embodiments, the single dose of the composition comprises about $10^{4.0}$ plaque-forming units (PFU) of RSV particles. In some embodiments, single dose of the composition comprises about $10^{5.0}$ plaque-forming units (PFU) of RSV particles. In some embodiments, the single dose of the composition comprises about $10^{6.0}$ plaque-forming units (PFU) of RSV particles.

In some embodiments, the single dose is administered in about 0.2 ml to about 1 ml total volume per subject. In some embodiments, the single dose is administered in about 0.5 ml total volume per subject.

In some embodiments, the RSV genome or antigenome comprises at least one characteristic listed in (i)-(vi). In some embodiments, the RSV genome or antigenome comprises all characteristics listed in (i)-(vi).

In some embodiments, the RSV genome or antigenome comprises a nucleotide sequence that is at least 90% identical to SEQ ID NO:1. In some embodiments, the RSV genome or antigenome comprises the nucleotide sequence of SEQ ID NO:1.

In some embodiments, the RSV particle is live attenuated. In some embodiments, the RSV genome or antigenome comprises one or more dimorphisms selected from the group consisting of: (i) A/G dimorphism at nucleotide position 285 in the NS1 gene resulting in a mixture of amino acid assignments S/G at amino acid position 63 (ii) C/T dimorphism at nucleotide position 900 in the NS2 gene; and (iii) T/G dimorphism at nucleotide position 4311 in the SH gene resulting in a mixture of amino acid assignments N/K at amino acid position 3.

In some embodiments, the subject is less than about 18 months of age. In some embodiments, the subject is less than about 12 months of age. In some embodiments, the subject is less than about 6 months of age. In some embodiments, the subject is less than about 4 months of age. In some embodiments, the subject is less than about 2 months of age.

In some embodiments, the route of administration is intranasal, intramuscular or subcutaneous. In some embodiments, the route of administration is intranasal. In some embodiments, the composition is administered via nasal drops. In some embodiments, the composition is administered via nasal spray. In some embodiments, the composition is administered via nasal powder.

In some embodiments, the RSV particle exhibits restricted replication in the subject, In some embodiments, the RSV particle exhibits enhanced immunogenicity in the subject, In some embodiments, the subject exhibits anamnestic response to wild type RSV infection.

In some embodiments, the invention includes a method for vaccinating a human subject against respiratory syncytial virus (RSV) infection, comprising administering to the subject a composition comprising an RSV particle that comprises an RSV genome or antigenome, wherein the subject less than about 24 months of age, wherein the composition is administered intranasally in a single dose, and wherein the RSV genome or antigenome comprises: (i) a functional deletion in the M2-2 ORF corresponding to a deletion of nucleotides 8201-8434 in Genbank Accession No. M74568; (ii) presence of, corresponding to the nucleotides in Genbank Accession No. M74568, C4488 in the SH gene, C4491 in the SH gene, A4494 in the SH gene, A4496 in the SH gene, G4497 in the SH gene, and a nucleotide sequence corresponding to nucleotides 4498-4609 in the non-translated region of the SH gene; (iii) presence of G at a nucleotide position corresponding to position 1209 in Genbank Accession No. M74568 encoding an Alanine at position 24 in the N protein; (iv) presence of G at a nucleotide position corresponding to position 779 in Genbank Accession No. M74568 encoding an Arginine at position 51 in the NS2 protein; (v) presence of nucleotides corresponding to the nucleotides in Genbank Accession No. M74568 selected from the group consisting of: A1138, G1139, A5611, A5615, G5639, T7481 and A7559; (vi) presence of nucleotides corresponding to the nucleotides in Genbank Accession No. M74568 selected from the group consisting of: C404 in the NS1 gene, G1181 in the N gene, A1939 A1937 in the N gene, C6215 in the F gene, C6221 in the F gene, T6386 in the F gene, C7214 in the F gene, G7701 in the M2 gene; T8160 in the M2-2 gene, T8166 in the M2-2 gene, T8178 in the M2-2 gene, A8197 in the M2-2 gene, G8198 in the M2-2 gene; T 10514 in the L gene, A 13633 in the L gene, and T 13900 in the L gene and (vii) presence of T at a nucleotide position corresponding to position 1099 in Genbank Accession No. M74568. In some embodiments, the RSV genome or antigenome comprises the nucleotide sequence of SEQ ID NO:1.

In some embodiments, the single dose of the composition comprises about $10^5$ plaque-forming units (PFU) or less of the RSV particle. In some embodiments, the single dose of the composition comprises about $10^6$ plaque-forming units (PFU) or less of the RSV particle. In some embodiments, the single dose of the composition comprises about $10^4$ plaque-forming units (PFU) or less of the RSV particle.

BRIEF DESCRIPTION OF THE DRAWINGS

FIG. 1 is a schematic depiction of the screening, enrollment, and follow-up of RSV-seropositive children (A) and RSV-seronegative children (B) in the phase 1 clinical trial of the RSV MEDI ΔM2-2 vaccine. As described in the text, the study was initiated with administration of the RSV MEDI Δ M2-2 vaccine to 15 adults in an open label evaluation. For this portion of the study, 31 adults were screened, 19 were eligible, 15 were enrolled, and none were lost to follow-up.

FIG. 2 shows the proportions of RSV-seronegative vaccinees and placebo recipients with indicated illnesses. The placebo recipient (twin B) infected with vaccine virus is not included. Fever occurred in 4 of 20 vaccinees (1 of grade 0 severity, 1 of grade 2 severity, and 2 of grade 3 severity) and in 2 of 9 placebo recipients (both of grade 2 severity): grade 0, <38° C.; grade 1, ≥38° C. but ≤38.6° C.; grade 2, ≥38.7° C. but ≤39.1° C.; grade 3, ≥39.2° C. but ≤40.5° C. The two episodes of grade 3 fever in vaccinees occurred on days 24 to 26 after vaccination, when shedding of vaccine virus was not detected. URI (rhinorrhea) occurred in 17 of 20 vaccinees and 4 of 9 placebo recipients; cough occurred in 7 of 20 vaccinees and 3 of 9 placebo recipients; all of these illnesses were of grade 1 severity (that is, not requiring medical attention). An episode of otitis media (OM, grade 2 severity) occurred in a single vaccinee.

FIG. 3 shows vaccine virus shedding and serum RSV neutralizing antibody responses in seronegative recipients of RSV MEDI ΔM2-2 or rA2 cp248/404/1030/ASH. NW and serum specimens from the present study were evaluated for vaccine virus titer and serum neutralizing antibodies, respectively. Antibody testing was performed in parallel with specimens from the previous clinical evaluation of rA2 cp248/404/1030/ASH. (A) Peak viral titer (expressed as $\log_{10}$ PFU/ml). (B) RSV Plaque Reduction Neutralization Titers (PRNTs), expressed as 1/log 2. * P=0.005; +P=0.002 (Student's t test).

FIG. 4 shows the reverse cumulative distribution of RSV PRNT in seronegative vaccinees. The solid line represents vaccinees, and the dashed line represents placebo recipients. Antibody titers are expressed as 1/log 2, but for ease of interpretation, the titer corresponding to the arithmetic value of 1:64, achieved by 85% of vaccinees, is also shown.

FIG. 5. Rises in RSV PRNT during the surveillance period. RSV PRNT in sera from six vaccinees (filled circles) and three placebo recipients (open triangles) in whom ≥4-fold rises in titer between the pre- and post-surveillance specimens were detected (see text for additional details). Solid black lines, vaccinees with rises in RSV PRNT in whom no RSV-associated Medically Attended Acute Respiratory Illness (RSV MAARI) was detected (n=5; corresponding to subjects 33, 35, 44, 46, and 56 in the supplementary tables); dashed black line, vaccinee with rise in RSV PRNT in whom RSV MAARI was detected (n=1; subject 38 in the supplementary tables); solid grey line, placebo recipient with rise in RSV PRNT in whom no RSV MAARI was detected (n=1; subject 36 in the supplementary tables); dashed grey lines, placebo recipients with rise in RSV PRNT in whom RSV MAARI was detected (n=2; subjects 43 and 57 in the supplementary tables). Antibody titers are expressed as 1/log 2, but for ease of interpretation, titers corresponding to the arithmetic values of 1:16, 1:64, 1:256, 1:1024, and 1:4096 are also shown.

FIG. 6 shows the nucleotide sequence of the RSV MEDI ΔM2-2 recombinant virus (SEQ ID NO:1).

FIG. 7 shows the nucleotide sequence of the RSV rA2 cp248/404/1030ΔSH recombinant virus (SEQ ID NO:2).

DETAILED DESCRIPTION

Figure 1:
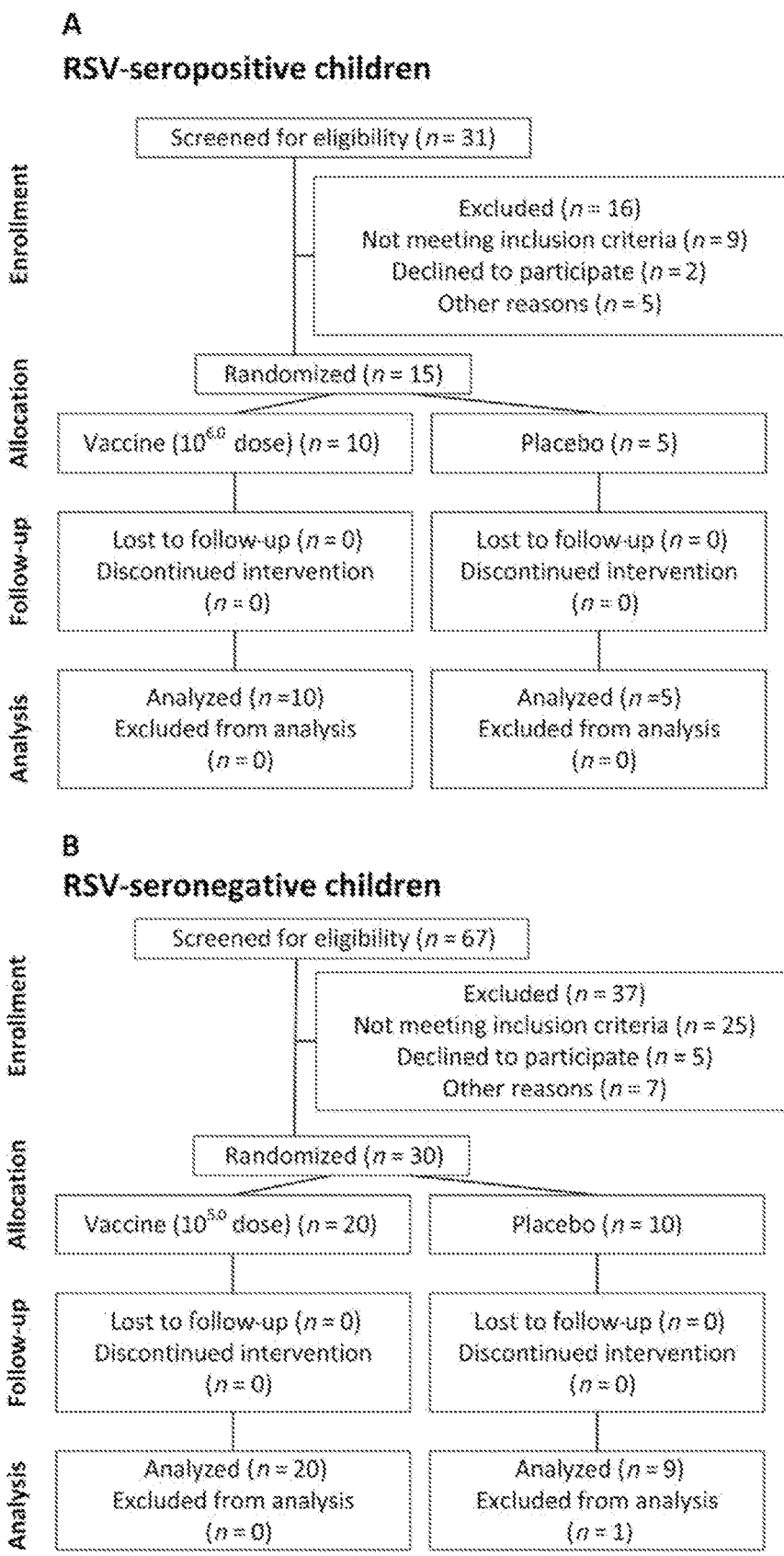

Reported herein is a method of vaccinating a human subject against Respiratory Syncytial Virus (RSV) by administering a composition comprising an immunogenic amount of a recombinant RSV particle described below to the subject. An embodiment of the composition comprising the recombinant RSV particle was evaluated as a live intranasal vaccine in adults, RSV-seropositive children and RSV-seronegative children. When results in RSV-seronegative children were compared to those achieved with the previous leading live attenuated RSV candidate vaccine, vaccine virus shedding was significantly more restricted, yet the post-vaccination RSV-neutralizing serum antibody achieved was significantly greater. Surveillance during the subsequent RSV season showed that several RSV-seronegative recipients had substantial rises of RSV-neutralizing serum antibodies indicative of exposure to RSV, and yet without reported RSV-associated illness, suggesting that the vaccine was protective yet primed for anamnestic responses to RSV. Thus, the composition comprising the recombinant RSV particle was intrinsically superior at eliciting protective antibody in the subjects. Surprisingly, a single dose of the composition was sufficient to provide the greater antibody response and protective effect in seronegative and/or RSV-naïve infants and children of less than about 24 months of age. This was an unexpected result, as it is currently anticipated that vaccination against RSV using a live, attenuated RSV vaccine will require administration of multiple doses, at least two or three at a minimum, in a single vaccination season to provide protective result.

Thus, in one embodiment, the invention includes a method of vaccinating a human subject to protect against RSV infection, or inducing a protective immune response in a human subject against RSV or stimulating the immune system of a human subject to elicit an immune response against RSV. The method comprises administering to the subject an immunogenic composition comprising an immunologically sufficient amount of an RSV particle.

In some embodiments of the invention, the RSV particle comprises an RSV genome or antigenome in which the RSV genome or antigenome contains a functional deletion in the M2-2 Open Reading Frame (ORF) which results in the ablation of the M2-2 protein, optionally further coupled with one or more characteristics as described in the table below. Without wishing to be bound by theory, the superior performance of the RSV particle is believed to be, at least in part, due to one or more of these characteristics.

| Gene Region | RSV Nucleotide | | Amino Acid | |
|---|---|---|---|---|
| | Genomic nt position[1] | cDNA | Amino Acid Position | CDNA |
| NS1 | 404 | C | 102 | N |
| NS2 | 779 | G | 51 | R |
| NS2/N ig[2] | 1099 | T | ncr[3] | — |
| N | 1138 | A | ncr[3] | — |
| N | 1139 | G | ncr[3] | — |
| N | 1181 | G | 14 | K |
| N | 1209 | G | 24 | A |
| N | 1937 | A | 266 | S |
| SH | 4488 | C | 62 | V |
| SH | 4491 | C | 63 | N |
| SH | 4494 | A | 64 | T |
| SH | 4496 | A | 65 | stop |
| SH | 4497 | G | 65 | stop |
| SH | 4498-4609 | No deletion | ncr[3] | — |
| G/F ig[2] | 5611 | A | ncr[3] | — |
| G/F ig[2] | 5615 | A | ncr[3] | — |
| G/F ig[2] | 5639 | G | ncr[3] | — |
| F | 6215 | C | 185 | V |
| F | 6221 | C | 187 | V |
| F | 6386 | T | 242 | G |
| F | 7214 | C | 518 | A |
| F | 7481 | T | ncr[3] | — |
| F/M2 ig[2] | 7559 | A | ncr[3] | — |
| M2 | 7701 | G | 32 | P |
| M2-2 | 8160 | T | 1 | M |
| M2-2 | 8166 | T | 3 | M |
| M2-2 | 8178 | T | 7 | M |
| M2-2 | 8197 | A | 13 | stop |
| M2-2 | 8198 | G | ncr[3] | — |
| M2-2 | 8201-8434 | 234 nt | | M2-2 del |

-continued

| Gene Region | RSV Nucleotide | | Amino Acid | |
|---|---|---|---|---|
| | Genomic nt position[1] | cDNA | Amino Acid Position | CDNA |
| | | deletion | | |
| L | 10514 | T | 673 | L |
| L | 13633 | A | 1712 | T |
| L | 13900 | T | 1801 | S |

[1]Genomic position numbered relative to WT RSV strain A2 (Genbank accession number M74568). All sequences are positive-sense.
[2]ig, intergenic region
[3]ncr, non-coding region The numbering used in this disclosure is based on the sequence of the wild-type RSV A2 strain (Genbank accession number M74568) and all sequences described are in positive-sense. Given that a variety of RSV strains exist (e.g., RSV A2, RSV B1, RSV Long), those skilled in the art will appreciate that certain strains of RSV may have nucleotide or amino acid insertions or deletions that alter the position of a given residue. For example, if a protein of another RSV strain had, in comparison with strain A2, two additional amino acids in the upstream end of the protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

The wild type RSV virus genome or antigenome encodes the following 11 proteins: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N—P-M-SH-G-F-M2-L. The complete amino acid sequences of these proteins, and nucleotides encoding them are known in the art.

In some embodiments of the present invention, the RSV genome or antigenome comprises a functional deletion in the M2-2 ORF which comprises a deletion of 234 nt corresponding to positions 8201-8434 encoding the C-terminal 78 amino acids of the M2-2 protein. The N-terminal 12 amino acid residues encoded by the M2-2 open reading frame are maintained at the region of overlap with the M2-1 open reading frame. See Example 1. The deletion in the M2-2 ORF results in the ablation of the M2-2 protein which down-regulates viral RNA replication and up regulates gene transcription and antigen synthesis. This is believed to be the first time that a viral vaccine candidate designed for increased gene transcription has been evaluated in humans.

In some embodiments, the RSV genome or antigenome further comprises one or more of the following characteristics. In some embodiments, the RSV genome or antigenome comprises presence of G at a nucleotide position corresponding to position 779 encoding an Arginine at position 51 in the NS2 protein. In some embodiments, the RSV genome or antigenome comprises the presence of G at a nucleotide position corresponding to position 1209 encoding an Alanine at position 24 in the N protein.

In some embodiments, the RSV genome or antigenome comprises the presence of C at a nucleotide position corresponding to position 404 in the NS1 gene. In some embodiments, the RSV genome or antigenome comprises the presence of T at a nucleotide position corresponding to position 1099 in the NS2/N intergenic region.

In some embodiments, the RSV genome or antigenome comprises the presence of A at a nucleotide position corresponding to position 1138 in the non-coding region of the N gene. In some embodiments, the RSV genome or antigenome comprises the presence of G at a nucleotide position corresponding to position 1139 in the non-coding region of the N gene. In some embodiments, the RSV genome or antigenome comprises the presence of G at a nucleotide position corresponding to position 1181 in the N gene. In some embodiments, the RSV genome or antigenome comprises the presence of A at a nucleotide position corresponding to position 1937 in the N gene.

Bukreyev et al. previously described the 6120 mutation in the SH gene which involves introduction of five translationally-silent point mutations at nucleotide position 4488, 4491, 4494, 4496 and 4497, and deletion of nucleotides 4498-4609 in the downstream non-translated region of the SH gene (Bukreyev et al., 2001. J Virol. 75:12128-12140). In some embodiments, the RSV genome or antigenome does not contain the 6120 mutation. In some embodiments, the RSV genome or antigenome comprises the presence of C at a nucleotide position corresponding to position 4488 in the SH gene. In some embodiments, the RSV genome or antigenome comprises the presence of C at a nucleotide position corresponding to position 4491 in the SH gene. In some embodiments, the RSV genome or antigenome comprises the presence of A at a nucleotide position corresponding to position 4494 in the SH gene. In some embodiments, the RSV genome or antigenome comprises the presence of A at a nucleotide position corresponding to position 4496 in the SH gene. In some embodiments, the RSV genome or antigenome comprises the presence of G at a nucleotide position corresponding to position 4497 in the SH gene. In some embodiments, the RSV genome or antigenome comprises the presence in the non-coding region of the SH gene of a nucleotide sequence corresponding to nucleotides 4498-4609.

In some embodiments, the RSV genome or antigenome comprises the presence of A at a nucleotide position corresponding to position 5611 in the G/F intergenic region. In some embodiments, the RSV genome or antigenome comprises the presence of A at a nucleotide position corresponding to position 5615 in the G/F intergenic region. In some embodiments, the RSV genome or antigenome comprises the presence of G at a nucleotide position corresponding to position 5639 in the G/F intergenic region.

In some embodiments, the RSV genome or antigenome comprises the presence of C at a nucleotide position corresponding to position 6215 in the F gene. In some embodiments, the RSV genome or antigenome comprises the presence of C at a nucleotide position corresponding to position 6221 in the F gene. In some embodiments, the RSV genome or antigenome comprises the presence of T at a nucleotide position corresponding to position 6386 in the F gene. In some embodiments, the RSV genome or antigenome comprises the presence of C at a nucleotide position corresponding to position 7214 in the F gene. In some embodiments, the RSV genome or antigenome comprises the presence of T at a nucleotide position corresponding to position 7481 in the non-coding region of the F gene.

In some embodiments, the RSV genome or antigenome comprises the presence of, A at a nucleotide position corresponding to position 7559 in the F/M2 intergenic region.

In some embodiments, the RSV genome or antigenome comprises the presence of G at a nucleotide position corresponding to position 7701 in the M2 gene. In some embodiments, the RSV genome or antigenome comprises the presence of T at a nucleotide position corresponding to position 8160 in the M2 gene. In some embodiments, the RSV genome or antigenome comprises the presence of T at a nucleotide position corresponding to position 8166 in the M2 gene. In some embodiments, the RSV genome or antigenome comprises the presence of T at a nucleotide position corresponding to position 8178 in the M2 gene. In some embodiments, the RSV genome or antigenome comprises the presence of A at a nucleotide position corresponding to position 8197 in the M2 gene. In some embodiments, the RSV genome or antigenome comprises the presence of G at a nucleotide position corresponding to position 8198 in the M2 gene.

In some embodiments, the RSV genome or antigenome comprises the presence of T at a nucleotide position corresponding to position 10514 in the L gene. In some embodiments, the RSV genome or antigenome comprises the presence of A at a nucleotide position corresponding to position 13633 in the L gene. In some embodiments, the RSV genome or antigenome comprises the presence of T at a nucleotide position corresponding to position 13900 in the L gene.

In some embodiments, the RSV genome or antigenome comprises the M2-2 deletion and further comprises at least one of the other characteristics described above. In some embodiments, the RSV genome or antigenome comprises the M2-2 deletion and at least two, or three, or four, or five, or six, or seven, or eight, or nine, or ten, or eleven, or twelve, or thirteen, or fourteen, or fifteen, or sixteen, or seventeen, or eighteen, or nineteen, or twenty, or twenty one, or twenty two, or twenty three, or twenty four, or twenty five, twenty six, or twenty seven, or twenty eight, or twenty nine, or thirty, or thirty one of the additional characteristics described above. In some embodiments, the RSV genome or antigenome comprises the M2-2 deletion and all of the additional characteristics described above.

In some embodiments, the RSV genome or antigenome comprises a functional deletion in the M2-2 ORF corresponding to a deletion of nucleotides 8201-8434 in Genbank Accession No. M74568 and optionally comprises a characteristic selected from the following: i) presence of one or more of, corresponding to the nucleotides in Genbank Accession No. M74568, C4488 in the SH gene, C4491 in the SH gene, A4494 in the SH gene, A4496 in the SH gene, G4497 in the SH gene, and a nucleotide sequence corresponding to nucleotides 4498-4609 in the non-translated region of the SH gene, ii) presence of G at a nucleotide position corresponding to position 1209 in Genbank Accession No. M74568 encoding an Alanine at position 24 in the N protein, iii) presence of G at a nucleotide position corresponding to position 779 in Genbank Accession No. M74568 encoding an Arginine at position 51 in the NS2 protein, iv) presence of one or more nucleotides corresponding to the following nucleotides in Genbank Accession No. M74568 selected from the group consisting of: A1138, G1139, A5611, A5615, G5639, T7481 and A7559, v) presence of one or more nucleotides corresponding to the following nucleotides in Genbank Accession No. M74568 selected from the group consisting of: C404 in the NS1 gene, G1181 in the N gene, A1937 in the N gene, C6215 in the F gene, C6221 in the F gene, T6386 in the F gene, C7214 in the F gene, G7701 in the M2 gene; T8160 in the M2-2 gene, T8166 in the M2-2 gene, T8178 in the M2-2 gene, A8197 in the M2-2 gene, and G8198 in the M2-2 gene, vi) presence of T at a nucleotide position corresponding to position 1099 in Genbank Accession No. M74568, and vii) a combination of the above.

In some embodiments, the RSV A2 genome or antigenome comprises the M2-2 deletion and all of the characteristics described in (i)-(vi). In some embodiments, the RSV particle comprises an RSV genome or antigenome comprising the sequence shown in SEQ ID NO: 1. This RSV construct is also referred herein as RSV MEDI ΔM2-2.

Reference to a polypeptide or polynucleotide sequence includes a polypeptide or polynucleotide sequence that is at least about 50%, or at least about 55%, or at least about 60%, or at least about 65%, or at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical (or any percent identity between 45% and 100%, in whole integer increments), to the polypeptide or polynucleotide sequence.

Compared to wild-type RSV, the RSV MEDI ΔM2-2 mutant exhibited a shift in the viral RNA synthesis program such that genome replication was decreased and gene transcription was increased. This resulted in a substantial increase in synthesis of the viral proteins, including the major neutralization and protective antigens, suggesting the possibility of an inherent increase in immunogenicity per infectious unit. In addition, because it is based on a large deletion that ablates expression of a viral protein, the attenuation phenotype of RSV MEDI ΔM2-2 is very stable, obviating a complication of vaccines based on point mutations. In nonhuman primates, RSV MEDI ΔM2-2 was highly restricted in replication but induced substantial neutralizing serum antibody responses and protected against challenge, although it could not be determined whether RSV MEDI ΔM2-2 was inherently more immunogenic than wild-type RSV. On the basis of this preclinical profile of substantial attenuation and immunogenicity, a stepwise phase 1 evaluation of the RSV MEDI ΔM2-2 vaccine candidate was conducted in adults and in RSV-seropositive and RSV-seronegative children, as described in detail in Example 2.

A lot of RSV MEDI ΔM2-2 clinical trial material (CTM) suitable for human evaluation as a live attenuated intranasal vaccine was manufactured. The nucleotide sequence of the RSV MEDI ΔM2-2 CTM was determined and was found to be identical to that of its cDNA clone of origin (SEQ ID NO:1) except for dimorphisms (mixtures of two different nucleotide assignments) at three sequence positions: (i) nucleotide 285, in the NS1 gene, was a mixture of A/G in the CTM compared to A in the cDNA, resulting in a mixture of amino acid assignments S/G at position 63 in the CTM compared to S in the cDNA; (ii) nucleotide 900, in the NS2 gene, was a mixture of C/T, compared to C in the cDNA, with no effect on amino acid coding; and (iii) nucleotide 4311, in the SH gene, was a mixture of T/G in the CTM compared to T in the cDNA, resulting in a mixture of amino acid assignments N/K at amino acid position 3 in the CTM, compared to N in the cDNA.

As described on Example 2, a single dose of a composition comprising the RSV MEDI ΔM2-2 particles was administered to RSV-seronegative infants and children of ages 6-24 months, as well as seropositive children and adults. The term "seronegative" as used herein means an individual (typically but not exclusively ≥6 months of age) who has a serum RSV-neutralizing antibody titer of <1:40 (determined by a complement-enhanced 60% plaque reduction neutralization assay), which typically indicates that the individual had not been previously infected with RSV. The term "RSV-naïve" as used herein means an individual (typically but not exclusively a young infant of <6 months old) who has not been previously exposed to RSV, but potentially might have maternally derived serum RSV-neutralizing antibodies that might have a titer ≥1:40.

In previous vaccine candidates, restriction of viral replication was associated with clinical attenuation, but vaccine candidates that were highly restricted in replication did not induce substantial plaque reduction neutralization titer (PRNT) in RSV-naïve children. Thus, it was difficult to achieve an appropriate balance between attenuation and antibody response in the pediatric target population.

When results in RSV-seronegative children were compared to those achieved with the previous leading live attenuated RSV candidate vaccine, the MEDI ΔM2-2 vaccine virus was significantly more restricted in replication and virus shedding was significantly less, yet the post-vaccination RSV-neutralizing serum antibody achieved (geometric mean titer (GMT)=1:97) was significantly greater. Without wishing to be bound by theory, it is believed that the ΔM2-2 attenuating mutation has produced a vaccine virus that induces a greater antibody response per infectious unit than previous attenuated strains via up-regulation of viral gene transcription and antigen synthesis. It is further believed that that the M2-2 deletion increases RSV-specific T cell responses as a result of increased expression of all viral genes and antigens. MEDI ΔM2-2 also is the first live attenuated RSV vaccine candidate to be evaluated intranasally in young children for which the attenuation does not involve cold-passage (cp) or temperature-sensitivity (ts) mutations, and indeed MEDI ΔM2-2 is not cold-adapted or temperature sensitive compared to wild type RSV. Temperature sensitivity mutations are thought to preferentially restrict viral replication in the lower (warmer) respiratory tract, and cp mutations similarly may restrict replication at increased temperature or favor it at reduced temperature (such as in the upper respiratory tract). These restrictions would not apply to MEDI ΔM2-2 given its lack of ts and cp properties, and it may be that this highly attenuated virus was nonetheless able to replicate in the respiratory tract beyond the upper respiratory tract, which would be thought to be more immunogenic. Therefore, this unusual property also may contribute to the unusual immunogenicity of MEDI ΔM2-2.

Lower respiratory illness (LRI) after administration of this vaccine was not observed, and the rates of fever, cough, and OM were comparable in seronegative vaccinees and placebo recipients. Rhinorrhea occurred in 73% of seronegative children, and more often in seronegative vaccinees (85%) than placebo recipients (44%), although this difference was not statistically significant. Furthermore, the observation (see below) that shedding of infectious vaccine virus was detected in only 60% of vaccinees, and that the mean peak group titer of shed virus irrespective of day was 1.5 $\log_{10}$ PFU/ml of nasal wash (compared to 6.0-7.0 $\log_{10}$ PFU/ml that is often observed with wild type RSV) suggests that this virus is very highly attenuated and unlikely to exhibit reactogenicity. Surveillance during the subsequent RSV season showed that several formerly seronegative RSV MEDI ΔM2-2 recipients had substantial antibody rises without reported illness. Post-vaccination surveillance also provided evidence that some vaccinees had been exposed to wild-type RSV, but had been protected from significant disease due to administration of the RSV MEDI ΔM2-2.

Thus, in the seronegative infants and children, RSV MEDI ΔM2-2 was highly restricted in replication yet more immunogenic than the previous lead live attenuated RSV vaccine candidate rA2 cp248/404/1030ΔSH (nucleotide sequence provided as SEQ ID NO:2 and shown in FIG. 7), and the RSV MEDI ΔM2-2 vaccine was protective yet primed for substantial anamnestic response to RSV.

Accordingly, in some embodiments, the RSV particle exhibits restricted replication (i.e. low replication as illustrated in Example 2) in the subjects. The term restricted replication refers to a lower degree of replication of the virus particle which leads to an attenuated phenotype of the virus. The restriction of replication may be measured or determined using known methods. For example, in some embodiments, the mean peak group post-vaccination viral infectivity titer in nasal wash specimens (irrespective of day, collected and assayed by the methods of this invention) from an exemplary group of vaccinated children is less than 2.5 $\log_{10}$ PFU/ml of nasal wash, and preferably less than or equal to 1.5-2.0 $\log_{10}$ PFU/ml nasal wash, whereas in comparison vaccination of a comparable group with the test particle rA2 cp248/404/1030ΔSH would yield a mean peak group viral infectivity titer that is approximately equal to or greater than 2.0-3.0 $\log_{10}$ PFU/ml nasal wash. In some embodiments, the frequency or rate of shedding of infectious vaccine virus (i.e., the percentage of the test group from whom infectious vaccine virus is detected) detected by culture following vaccination of an exemplary group of young children, using a dose of approximately 5.0 $\log_{10}$ PFU and following the methods of this invention, is less than approximately 80%, or less than approximately 70%, or about 60%.

In some embodiments, the RSV particle exhibits enhanced immunogenicity in the subjects (as compared, for example, to other known RSV vaccine candidates), in that it exhibits greater vaccine take in the subjects (more subjects show immune response to the vaccine) and/or it elicits higher antibody titers in the subjects. i), The immunogenicity may be measured or determined using known methods. For example, in some embodiments, if an exemplary group of vaccinees is given a dose (such as 5.0 $\log_{10}$ PFU) of the attenuated RSV particle of this invention versus a second, comparable group that received the same dose of a second test attenuated RSV particle with a similar level of attenuation, the mean group titer of serum RSV-neutralizing antibodies, detected by an assay such as the complement-enhanced 60% plaque reduction neutralization assay of this invention, that develops in response to the vaccinations is significantly greater (as determined by standard statistical tests) in the case of the particle of this invention than the test particle. In some embodiments, the immune response (e.g., serum RSV-neutralizing antibody tier) induced by the RSV particle may be higher than that induced by a second test attenuated RSV particle in a comparable test group even if the later particle is less attenuated. In some embodiments, the titer of serum RSV-neutralizing antibodies (sampled and assayed by the methods of this invention) induced by vaccination of an exemplary group of young children with the RSV particle of this invention is not statistically different than that obtained by natural infection (i.e., with a natural, unattenuated RSV) in a comparable group. In some embodiments, the subjects exhibit anamnestic response to a subsequent wild type RSV infection.

That a single dose regimen was sufficient to provide protective effect was a surprising result, as the standard practice in the art has been to administer multiple doses, or at a minimum at least two or three doses, of RSV vaccines in a single vaccination season to provide protective effect. For instance, Karron et al., J. of Infectious Diseases 191: 1093-1103 described clinical evaluation of two recombinant RSV candidate viruses rA2cp248/404ΔSH and rA2cp248/404/1030ΔSH in children and infants. Karron et al. concluded that rA2cp248/404ΔSH was not suitable for infants, given its level of replication in RSV-seronegative children. Further, while rA2cp248/404/1030ΔSH exhibited appropriate levels of attenuation, the virus shows limited antibody response in young infants and multiple doses of it, in excess of two, would be required to show any protective effect. Similarly, Wright et al., 2000, J. of Infectious Diseases 182:1331-42 tested the recombinant RSV candidate vaccine cpts-248/404 in a phase 1 trial, and concluded that because the second dose of vaccine did infect two out of three children not infected by the first dose, a schedule of two doses at a minimum of RSV vaccine would be required for immunization. Consistent with this, Malkin et al. 2013, PLOS ONE 8 (10): e77104 and Bernstein et al. 2012, Pediatr. Infect. Dis. J. 31:109-114 evaluated recombinant RSV virus vaccines in healthy, RSV-seronegative children 5 or 6 months to <24 months of age by administration of three doses of the vaccine. See also, Murphy and Collins 2002, J. Clin. Invest. 110:21-27, describing that a desirable immunization sequence employing live-attenuated RSV and PIV vaccines would be administration of RSV and PIV3 vaccines together as a combined vaccine given two or more times; Collins and Murphy 2002, Virology 296:204-211; stating that a live RSV vaccine would be administered two or three times during the first year of life to boost immunity, and Murphy et al. 1994, Virus Research 32:13-36, stating that immunization against RSV will require multiple doses of vaccine to achieve the level of immunity needed to prevent serious disease of the lower respiratory tract.

This expectation of the need for multiple doses is further exemplified by the rotavirus vaccines in current use. Rotavirus resembles RSV in being an RNA virus that infects and causes disease on mucosal surfaces, in this case the enteric tract. RSV and rotavirus are widely considered to share similar challenges in immunizing a mucosal surface in a young child with a live attenuated virus. The RotaTeg rotavirus vaccine in current use is given in three doses at 2, 4, and 6 months of age, and the Rotarix rotavirus vaccine in current use is given in two doses at 2 and 4 months of age. As another aspect, some studies with RSV suggest that the multiple-dose strategy needed to induce adequate protection may face another obstacle. For example, Malkin et al. 2013, PLOS ONE 8 (10): e77104, Karron et al., J. of Infectious Diseases 191:1093-1103, and Wright et al., 2000, J. of Infectious Diseases 182:1331-42 found that, although the seroresponse to the first dose of attenuated RSV was not high, it was highly restrictive to subsequent dose(s) of the attenuated strain (since a vaccine strain is already highly attenuated, even a small amount of immunity can be highly restrictive). As a result of the high level of restriction, the subsequent dose(s) of the live vaccines were poorly immunogenic. Thus, there can be an inherent limitation to the strategy of multiple doses for a live vaccine-namely, that the subsequent doses of a live vaccine may be too restricted to be immunogenic. This exemplified that the ability to induce a substantial immune response with a single dose of a live vaccine is highly advantageous.

Accordingly in one embodiment, the present invention comprises a method of vaccinating against RSV by administration of a single dose in a single vaccination season of the RSV particles described above. Reference herein to a method of vaccinating comprising administration of a single dose means a single dose in a single vaccination season which excludes a second dose in that vaccination season. In some embodiments of the invention, a single dose means a single dose during the lifetime of the subject. The single dose administration is sufficient to provide protective effect in infants and children, and a second dose is neither required nor administered.

The single dose of the composition comprises an "immunogenically effective dose" which is sufficient to induce or enhance the subject's immune response capabilities against RSV. In all subjects, the precise amount of RSV vaccine administered and the timing of administration will be determined by various factors, including the subject's state of health and weight, the mode of administration, the nature of the formulation, etc. Dosages generally range from about $10^{3.0}$ (3.0 $\log_{10}$) to about $10^{7.0}$ (7.0 $\log_{10}$) plaque forming units ("PFU") of virus per subject.

Thus, in some embodiments, the dosage ranges from $10^{3.0}$ (3.0 log 10) to about $10^{7.0}$ (7.0 log 10) PFU of virus per subject. In some embodiments, the dosage ranges from $10^{4.0}$ (4.0 log 10) to about $10^{6.0}$ (6.0 $\log_{10}$) PFU of virus per subject. In some embodiments, the dosage ranges from $10^{5.0}$ (5.0 log 10) to about $10^{6.0}$ (6.0 log 10) PFU of virus per subject.

In some embodiments, the single dose of the composition comprises about $10^{7.0}$ PFU of the RSV particles. In some embodiments, the single dose of the composition comprises about $10^{6.0}$ PFU of the RSV particles. In some embodiments, the single dose of the composition comprises about $10^{5.0}$ PFU of the RSV particles. In some embodiments, the single dose of the composition comprises about $10^{4.0}$ PFU of the RSV particles. In some embodiments, the single dose of the composition comprises about $10^{3.0}$ PFU of the RSV particles.

In some embodiments of the invention, the human subject is an infant or child. In some embodiments, the subject is less than about 36 months of age. In some embodiments, the subject is less than about 30 months of age. In some embodiments, the subject is less than about 24 months of age. In some embodiments, the subject is less than about 18 months of age. In some embodiments, the subject is less than about 12 months of age. In some embodiments, the subject is less than about 9 months of age. In some embodiments, the subject is less than about 8 months of age. In some embodiments, the subject is less than about 7 months of age. In some embodiments, the subject is less than about 6 months of age. In some embodiments, the subject is less than about 5 months of age. In some embodiments, the subject is less than about 4 months of age. In some embodiments, the subject is less than about 3 months of age. In some embodiments, the subject is less than about 2 months of age. In some embodiments, the subject is less than about 1 month of age. In some embodiments, the subject is less than about 30 days of age. In some embodiments, the subject is less than about 20 days of age. In some embodiments, the subject is less than about 15 days of age. In some embodiments, the subject is less than about 10 days of age. In some embodiments, the subject is a new born.

The composition may be administered by any suitable route, including but not limited to, intranasal, intratracheal, subcutaneous, intramuscular, transdermal, topical, oral or the like. In some embodiments, it may be administered intranasally, subcutaneously or, intramuscularly. In some embodiments, it may be administered intranasally. In some embodiments, it may be administered to the upper respiratory tract.

The administration may be performed via any suitable delivery mechanisms. For example, the composition may be delivered via drops, spray, aerosol delivery, powder, injection, topical formulation, oral inoculation, or the like.

In some embodiments, the composition may be administered intranasally via nasal drops, nasal spray (for example, using a device similar to Flumist), aerosol delivery, nasal powder or the like. Examples of possible nasal delivery modalities are provided in Djupesland. 2013, Drug Deliv. And Transl. Res. 3:42-62) and are expressly incorporated herein. In some embodiments, the composition may be administered intranasally via nasal drops. In some embodiments, the composition may be administered intranasally via nasal spray.

In some embodiments, the subject may be administered the composition intranasally in a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus. The nasal drops may be administered into one nostril or both nostrils. Thus, a part of the single dose of the composition may be administered in each nostril. In some embodiments, the single dose is administered in about 0.2 ml to about 1 ml total volume per subject. In some embodiments, the single dose is administered in about 0.5 ml total volume per subject.

In some embodiments, the composition may comprise the RSV particles and a physiologically acceptable carrier and/or adjuvant. Useful carriers are well known in the art, and include buffered solutions at neutral or physiological pH. Examples of suitable carriers include without limitation, buffered saline or Leibowitz L15 medium.

The resulting aqueous solutions may be packaged for use as is, or in frozen form that is thawed prior to use, or lyophilized, the lyophilized preparation being combined with a sterile solution prior to administration, as mentioned above. Alternatively, lyophilized preparations may be delivered to one or both nostrils as a powder (Djupesland. 2013, Drug Deliv. And Transl. Res. 3:42-62). The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-O-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition, the host responds to the vaccine by producing antibodies specific for RSV virus proteins, e.g., F and G glycoproteins. In addition, innate and cell-mediated immune responses are induced, which can provide antiviral effectors as well as regulating the immune response. As a result of the vaccination the host becomes at least partially or completely immune to RSV infection, or resistant to developing moderate or severe RSV disease, particularly of the lower respiratory tract.

In some embodiments, the present invention comprises a composition comprising the RSV particles described above and a pharmaceutically acceptable carrier. In some embodiments, the present invention comprises a composition comprising the RSV particles described above suspended in Leibowitz medium. In further embodiments, the present invention comprises a kit that includes the composition comprising the RSV particles described above and a pharmaceutically acceptable carrier.

To propagate a RSV virus for vaccine use and other purposes, a number of cell lines which allow for RSV growth may be used. RSV grows in a variety of human and animal cells. Preferred cell lines for propagating attenuated RS virus for vaccine use include DBSFRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

While some embodiments of the present invention have been described, it is apparent that modifications and adaptations of those embodiments will occur to those skilled in the art. It is to be expressly understood, however, that such modifications and adaptations are within the scope of the present invention, as set forth in the following exemplary claims. The examples and figures are provided for the purpose of illustration and are not intended to limit the scope of the present invention. Each publication or other reference disclosed herein is incorporated herein by reference in its entirety, to the extent that there is no inconsistency with the present disclosure.

Examples

Example 1. This Example Describes the Generation of the Recombinant RSV MEDI ΔM2-2 Vaccine As previously described, in the recombinant RSV vaccine with an M2-2 deletion, a complementary DNA (cDNA) fragment of 234 nucleotides containing the 78 C-terminal codons of the M2-2 ORF was removed from the antigenomic cDNA encoding the wild-type RSV A2 strain. The sequence encoding the first 12 codons of the M2-2ORF, that is, the region that mostly overlaps the M2-1 ORF, was maintained. The resulting plasmid was used for the recovery of the drug substance at MedImmune. Clinical trial material (CTM) was manufactured in qualified Vero cells at Meridian Life Science Inc. Sequence analysis confirmed that the seed virus and Final Drug Product, RSV Lot no. 002A, were of identical sequence, including the three polymorphisms. The RSV MEDI ΔM2-2 CTM was supplied to the clinical site as a frozen concentrate with a mean infectivity titer of $10^{7.0}$ PFU/ml. CTM was stored at −70° C. and diluted to dose on-site using Leibovitz L15 medium. L15 medium was also used as the placebo.

Example 2. This Example Describes the Clinical Evaluation of the RSV MEDI ΔM2-2

Isolation, Quantitation, and Characterization of Virus

NWs were performed using a nasal bulb syringe and 15 to 20 ml of Lactated Ringer's solution. NWs were snap-frozen on site and stored at −80° C. An aliquot of each NW was rapidly thawed and tested for infectivity by plaque assay in HEp-2 cells as previously described. Titers of vaccine virus are expressed as the number of PFU per milliliter of NW fluid. Specimens that were culture-negative were assigned a titer of 0.6 $\log_{10}$ PFU/ml.

Shedding of vaccine virus was also quantified by RT-qPCR amplification of the RSV matrix (M) protein. The following primers and probes were used: forward primer, 5'-gcaaatatggaaacatacgtgaacaa-3', reverse primer, 5'-GGCACCCATATTGTAAGTGATGCA-3', and probe, 5'-cttcacgaaggctccacata-3'. The assay was performed using the AgPath-ID One-Step RT-PCR kit and the 7300 Fast real-time PCR system (Applied Biosystems). Copy numbers of the gene of interest were calculated using a plasmid DNA standard curve for the RSV M gene. Analyses were performed using 7500 Fast System SDS software (Applied Biosystems). The limit of detection by RT-qPCR was 1.7 $\log_{10}$ copy numbers/ml; therefore, PCR-negative samples were assigned a titer of 1.7 $\log_{10}$ copy numbers/ml.

To determine whether the vaccine virus was genetically stable, the presence of the M2-2 deletion was verified by sequence analysis of NW isolates obtained from seronegative vaccinees at the time of peak viral shedding. Vaccine virus was isolated by one passage of NW fluid on Vero cells. RT-PCR was performed on total extracted RNA using RSV-specific primers, and consensus sequences of a region corresponding to nucleotides 7997 to 8817 of an RSV A2 reference sequence were generated (Genbank accession no. M74568, spanning the M2-2 deletion). In one case, only a shorter RT-PCR fragment could be obtained for sequence analysis of a region corresponding to nucleotides 8004 to 8695 of the reference sequence.

Immunologic Assays

Serologic specimens: RSV MEDI ΔM2-2 study. Sera were obtained to measure antibodies to RSV before inoculation, about 1 month after inoculation in adults and seropositive children and about 2 months after inoculation in seronegative children. To measure serum antibody responses during the surveillance period, sera were also obtained from seronegative children between 1 October and 31 October of the calendar year in which the child was enrolled and between 1 April and 30 April of the following calendar year. Thus, adults and seropositive children each had two serum specimens obtained, and seronegative children each had three or four serum specimens obtained, depending on the time of enrollment.

Serologic specimens: Previous study of RSVcp248/404/1030/ΔSH. To compare antibody responses to RSV MEDI ΔM2-2 and the previously evaluated RSVcp248/404/1030/ΔSH in RSV-naïve children, paired pre- and post-vaccination specimens from eight RSV-seronegative children who had received 105.3 PFU of RSVcp248/404/1030/ΔSH in an earlier study (8) were retested for neutralizing antibodies to RSV as described below.

Antibody assays. Sera from all subjects were tested for antibodies to RSV by 60% complement-enhanced plaque reduction neutralization assay and for IgG antibodies to the RSV F glycoprotein by ELISA. The ELISA was performed as previously described, except that the RSV F, provided by Novavax Inc., was a purified baculovirus-expressed protein; 20 ng per well was used in the assay. For the neutralizing antibody assay, the starting dilution was 1:10, and for the ELISA, the starting dilution was 1:200 for adult sera and 1:50 for pediatric sera. The PRNT and RSV F IgG titer are expressed as reciprocal log 2. Antibody responses were defined as ≥4-fold increase in titer in paired specimens.

Data Analysis

Infection was defined as either the detection of vaccine virus by culture or rRT-qPCR or a ≥4-fold rise in RSV serum neutralizing antibody or in RSV F serum antibody. The mean peak titer of vaccine virus shed ($\log_{10}$ PFU/ml) was calculated for infected vaccinees only. The neutralizing antibody and RSV F IgG reciprocal titers were transformed to log 2 values for calculation of mean log 2 titers, and Student's t test was used to compare mean peak viral titers and antibody titers between groups. Rates of illness among vaccinees and placebo recipients were compared by the two-tailed Fisher's exact test.

Study Population, Study Design, and Clinical Trial Oversight

This phase 1 trial was conducted at the Center for Immunization Research (CIR), Johns Hopkins Bloomberg School of Public Health, and Seattle Children's Research Institute between September 2011 and March 2014. The RSV MEDI ΔM2-2 vaccine was evaluated sequentially in (i) adults who were not screened for RSV serostatus (but who all proved to be RSV seropositive), (ii) RSV-seropositive children ages 15 to 59 months, and (iii) RSV seronegative children ages 6 to 24 months. Studies in adults were conducted as open-label trials, with all subjects receiving vaccine. Studies in children were conducted as randomized, double-blind, and placebo controlled trials, with subjects randomized 2:1 to receive vaccine or placebo (FIG. 1). Randomization was performed in blocks of three (two vaccinees and one placebo recipient) to permit unblinding and analysis of adverse events throughout the study, which was done when each group of three subjects completed the initial follow-up period (about 28 days for RSV-seropositive children and about 56 days for RSV-seronegative children). To maintain the study blind, randomization and preparation of the study agent (vaccine or placebo) were performed by study personnel who were not involved in the clinical assessment of study subjects. Vaccine and placebo were each administered in a volume of 0.5 ml as nose drops (about 0.25 ml per nostril). Adults and RSV-seropositive vaccinees received $10^{6.0}$ PFU of vaccine; RSV-seronegative vaccinees received $10^{5.0}$ PFU of vaccine. Written informed consent was obtained from study participants (adults) or from the parents or guardians of study participants (children) before enrollment. These studies were conducted in accordance with the principles of the Declaration of Helsinki and the Standards of Good Clinical Practice (as defined by the International Conference on Harmonization). The study was performed under NIAID-held Investigational New Drug applications (BB-IND no. 14763) and was reviewed by the U.S. Food and Drug Administration. The clinical protocol, consent forms, and Investigators' Brochure were developed by CIR and NIAID investigators and were reviewed and approved by the Western Institutional Review Board, and the NIAID Office of Clinical Research Policy and Regulatory Operations (OCR-PRO). Clinical data were reviewed by CIR and NIAID investigators and by the Data Safety Monitoring Board of the NIAID Division of Clinical Research.

Clinical assessment: Acute phase. For adults and RSV-seropositive children enrolled in this trial, clinical assessments and NWs were performed on study day 0 (the day of vaccination, with the NW performed before inoculation) and on days 3 to 7 and 10 after inoculation. After day 10, illness data (adverse events and reactogenicity events) were collected through day 28, with additional physical examinations performed and NWs obtained in the event of LRI. All LRIs were defined as SAEs, regardless of severity. For seronegative children, clinical assessments and NWs were performed on study days 0, 3, 5, and 7 and on days 10, 12, 14, 17, 19, 21, and 28±1 day. After the last scheduled NW, illness data were obtained for seronegative children through day 56, with physical examinations performed and additional NWs obtained in the event of LRI. Titers of vaccine virus in NW specimens were determined as described below. Fever, URI (rhinorrhea or pharyngitis), cough, LRI, and OM were defined as previously described (8). When illnesses occurred, NWs were tested for adventitious agents by rRT-PCR (Fast-track Diagnostics).

Clinical assessment: Surveillance. RSV-seronegative children were monitored for symptomatic medically attended RSV-associated illness in this study as previously described (8). In brief, families were contacted weekly between 1 November and 31 March to determine whether MAARIs had occurred, which were defined as fever, URI, LRI, or OM. For each illness episode, a clinical assessment was performed, and a NW obtained for quantitative viral testing by rRT-qPCR and culture as described below.

Study Participants

RSV MEDI ΔM2-2 was sequentially evaluated in 15 adults, 15 RSV seropositive children, and 30 RSV-seronegative infants and children. This vaccine was evaluated in an open label trial in adults and in randomized, placebo-controlled, double-blind trials in the pediatric populations (FIG. 1). All adults received $10^{6.0}$ plaque-forming units (PFU) of vaccine; 10 RSV-seropositive children received $10^{6.0}$ PFU of vaccine and 5 received placebo; and 20 RSV-seronegative vaccinees received $10^{5.0}$ PFU of vaccine and 10 received placebo. The mean age of adult participants was 36 years (range, 20 to 49 years); of RSV-seropositive participants, 37 months (range, 18 to 59 months); and of RSV-seronegative participants, 13 months (range, 6 to 24 months). Of the 60 participants, 48% were female, 53% white, 33% black, and 14% described as of mixed race.

Infectivity and Adverse Events

During the 28-day postimmunization reporting period, 3 of 15 vaccinated adults developed respiratory illnesses [hoarseness (1), pharyngitis (1), and rhinorrhea and cough (1)], but none shed vaccine virus or had rises in serum RSV antibody titers. Upper respiratory illness [(URI); rhinorrhea] was observed in 4 of 10 vaccinated RSV-seropositive children during this 28-day period (Table 1); each symptomatic child had rhinovirus or enterovirus detected in nasal wash (NW) at the time of illness. As in the adults, none of the seropositive children shed vaccine virus, which is consistent with attenuation.

Figure 2:
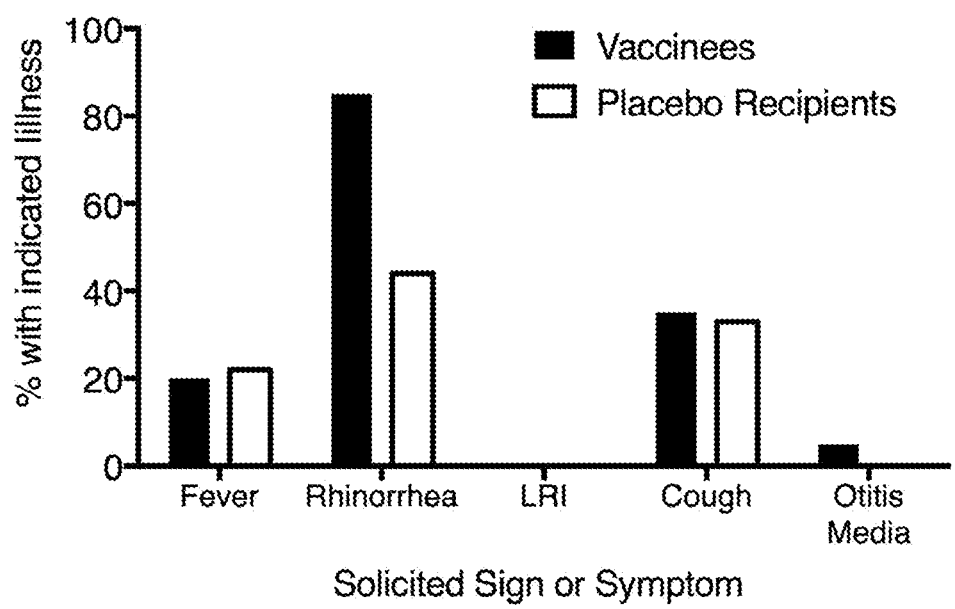

URI (rhinorrhea), cough, and febrile illnesses occurred frequently in RSV-seronegative vaccinees and placebo recipients during the 28 days after immunization (Supplemental Table 1 and FIG. 2). The rates of fever (20% versus 22%) and cough (35% versus 33%) were comparable in vaccinees and placebo recipients (Supplemental Table 1 and FIG. 2). URI occurred more often in seronegative vaccinees than in placebo recipients (85% versus 44%), but this difference was not significant and all episodes were of grade 1 (mild) severity (Supplemental Table 1 and FIG. 2). None of the children experienced LRI, and one vaccinee had otitis media (OM). Other viruses were detected frequently in symptomatic children, including rhinovirus, enterovirus, parechovirus, adenovirus, coronavirus, bocavirus, and parainfluenza viruses types 1 and 4.

Kawasaki disease was reported as a serious adverse event (SAE) in a seronegative vaccinee. Vaccine virus was detected in this child's NW by culture on study days 5,7, and 10 and by real-time reverse transcription quantitative polymerase chain reaction (rRT-qPCR) on study days 3 to 12, and the child had rhinorrhea on study days 8 to 11. The child was otherwise without symptoms until study day 32 when she became febrile. She subsequently developed a rash and oral lesions that were consistent with Kawasaki disease and was hospitalized on study day 35. The child was treated with aspirin and intravenous immuno-globulin (IGIV) and recovered without sequelae. The SAE was judged to be unrelated to the study product on the basis of the interval between infection with vaccine virus and onset of symptoms, as well as the absence of any known association between RSV and Kawasaki disease.

Transmission of vaccine virus occurred between a seronegative vaccinee and a placebo recipient who were 13-month-old twin siblings. Twin A (the vaccinee) had vaccine virus detected in NW on study days 5, 7, and 10 and rhinorrhea on study days 8 to 11. Twin B (the placebo recipient) had vaccine virus detected in NW on study days 14 and 17, accompanied by a temperature of 38.1° C. on day 17 (infected placebo recipient, Supplemental Table 1). The peak titer of vaccine virus shed by each child was 2.0 $\log_{10}$ PFU/ml. Sequence analysis revealed that the vaccine virus shed by both children retained the deletion of the M2-2 ORF. Illness, replication, and immunogenicity data from this infected placebo recipient are reported as a separate line item in Tables 1 and 2, and surveillance data from this placebo recipient were excluded from the analysis. These data indicate a major advantage of the MEDI ΔM2-2 vaccine. Specifically, RNA viruses are well known to have a high mutation rate with regard to single nucleotide changes, such that attenuating point mutations are readily subject to de-attenuation. In contrast, gene deletions such as the ΔM2-2 mutation are not known to be subject to de-attenuation. Thus, in this example, the MEDI ΔM2-2 virus was able to transmit to a second individual in a situation where there is very extensive personal contact, such as between young twins, but the virus remained genetically stable and attenuated, and the transmitted virus replicated to only low titer without disease and induced immunity in the twin.

Replication and Genetic Stability of RSV MEDI ΔM2-2

As noted above, vaccine virus was not detected by viral culture in NW obtained from adults and RSV-seropositive children, consistent with the restriction in replication expected for live attenuated RSV vaccines in RSV-experienced populations.

Figure 3:
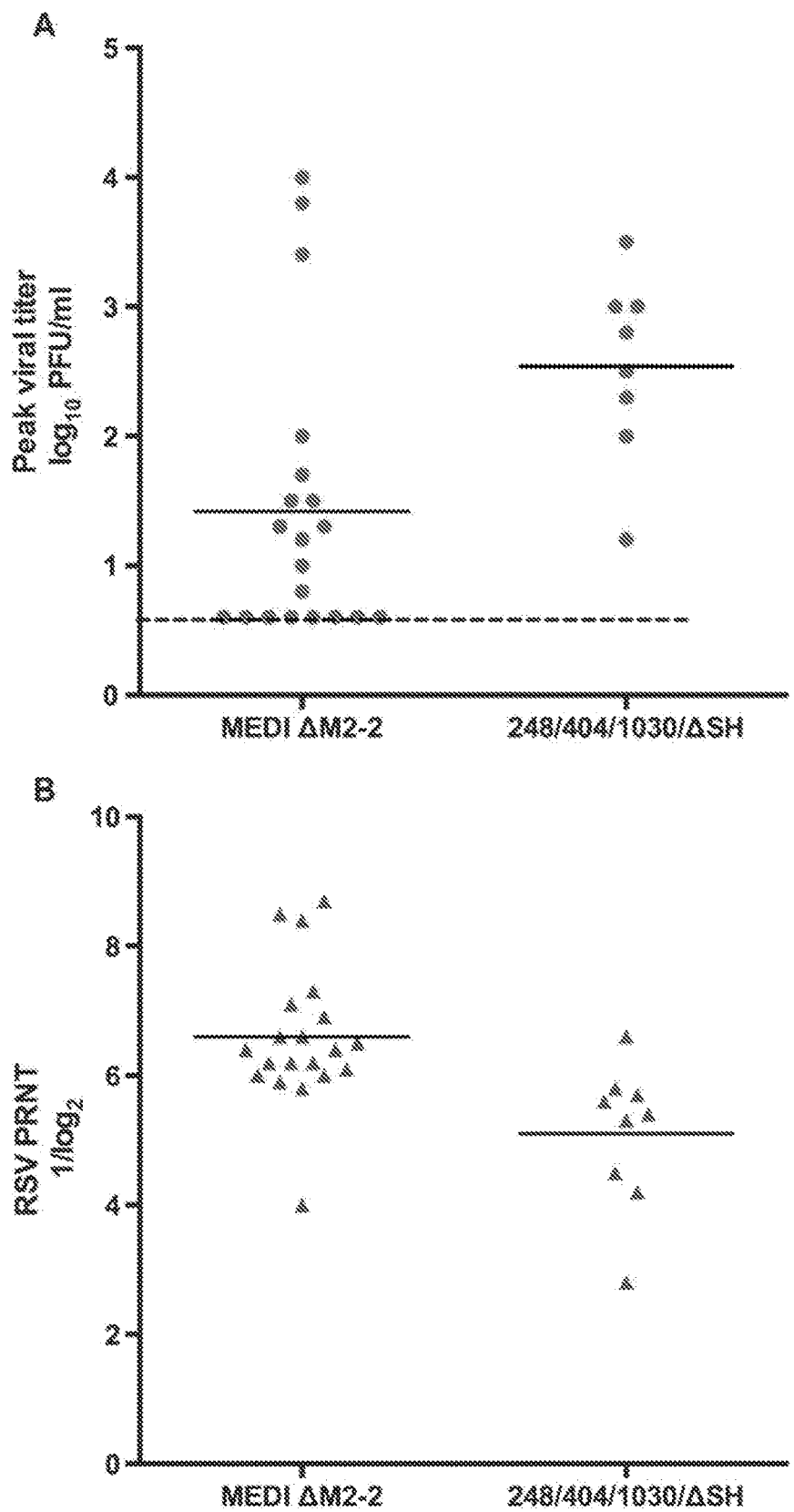

In contrast, vaccine virus was detected in NW by culture in 12 of 20 RSV-seronegative vaccinees and by RTqPCR in 17 of 20 RSV-seronegative vaccinees (Supplemental Table 2 and FIG. 3A; the 3 vaccinees who were negative by RT-qPCR also were negative by culture). The mean peak titer of virus detected by culture in these children was 1.5 $\log_{10}$ PFU/ml. This was significantly lower than that detected in NW from seronegative recipients of rA2 cp248/404/1030/ ΔSH (2.5 log$_{10}$ PFU/ml, P=0.005; FIG. 3A), a previously studied vaccine candidate that was well tolerated and immunogenic in seronegative infants and children (8). Partial sequence analysis of NW isolates obtained at the peak of vaccine shedding from 15 RSV-seronegative vaccinees verified the presence of the M2-2 deletion. PCR products for sequence analysis could not be obtained from four seronegative vaccinees from whom infectious vaccine virus was not recovered and from one vaccine with low peak titer (1.3 log$_{10}$ PFU/ml).

Antibody Responses to RSV MEDI ΔM2-2.

A single RSV-seropositive vaccinee had a rise in RSV F serum immunoglobulin G (IgG) titer (Table 2). Thus, none of the adults and one RSV-seropositive vaccinee had evidence of infection with vaccine virus, which is consistent with attenuation. In addition, a seropositive placebo recipient had a rise in both RSV F serum IgG and RSV-neutralizing serum antibody titers [measured as plaque reduction neutralization titer (PRNT)], which likely indicated an infection with a circulating wildtype RSV that was not detected during the post-inoculation follow-up period.

Figure 4:
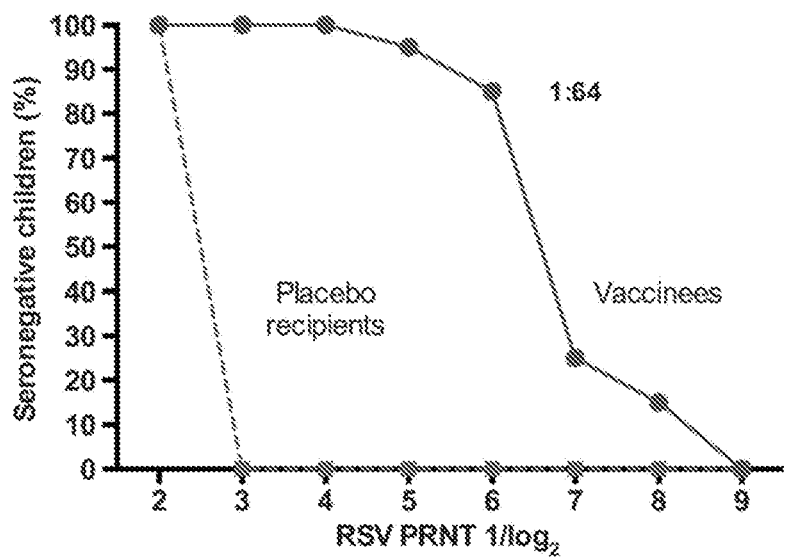

Nineteen of 20 RSV-seronegative children developed neutralizing serum antibody responses, and 18 of 20 developed RSV F serum IgG antibody responses after vaccination (Table 2 and FIG. 4). In seronegative children, the mean post-vaccination PRNT was 6.6 log 2, or 1:97 (Table 2); 85% achieved PRNT ≥6.0 log 2, or 1:64 (FIG. 4). There was no apparent relationship between the magnitude of vaccine virus shedding and the magnitude of the antibody response. Mean PRNTs were significantly higher in seronegative recipients of MEDI ΔM2-2 than in recipients of rA2 cp248/404/1030/ΔSH (6.6 log 2 versus 5.1 log 2, or 1:97 versus 1:34; P=0.002; FIG. 3B). With the exception of the twin to whom vaccine virus was transmitted, none of the RSV-seronegative placebo recipients developed a rise in RSV PRNT.

RSV Surveillance in Seronegative Children with Respect to RSV Related Illness and Antibody Response Surveillance for medically attended acute respiratory illness (MAARI) was conducted for the seronegative cohort during the RSV season (1 November to 31 March) after vaccine administration, and pre- and post-surveillance sera were collected and tested for PRNT as described above. MAARI was frequent, with 15 episodes occurring in seven vaccinees and 10 episodes occurring in six placebo recipients. However, only three instances of RSV-associated MAARI were detected: RSV subgroup A-associated illness occurred in one placebo recipient (rhinorrhea, cough, and wheezing), and RSV subgroup B-associated illness occurred in one vaccinee (rhinorrhea and cough) and one placebo recipient (rhinorrhea and fever).

Figure 5:
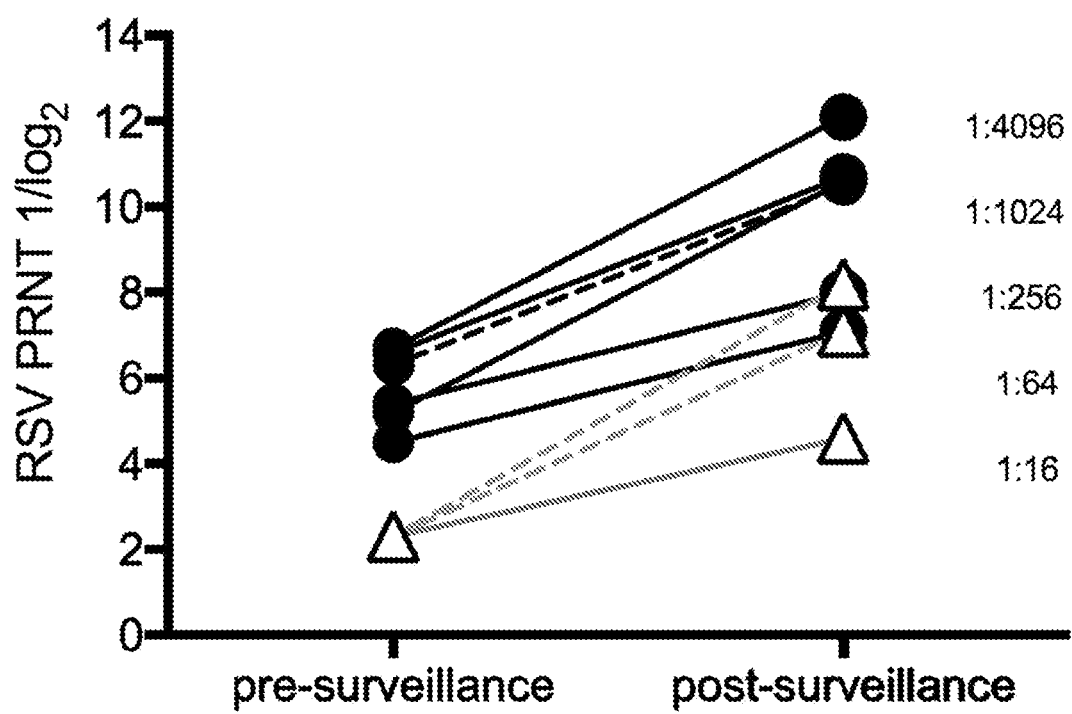

Despite infrequent RSV MAARI, ≥4-fold increases in RSV PRNT were detected in post-surveillance sera from three placebo recipients and six vaccinees, including the three subjects in whom wild-type RSV was detected. The mean post-surveillance log 2 PRNT in the three placebo recipients in whom rises were observed (6.6 log 2) was identical to the mean log 2 PRNT observed in the vaccine recipients after vaccination (Table 2). Thus, the mean RSV PRNT achieved after a single dose of RSV MEDI ΔM2-2 in RSV-seronegative children was the same as that achieved after a primary wild-type RSV infection. Notably, the post-surveillance geometric mean PRNT in the six vaccinated children in whom rises were observed were significantly greater than those achieved in the placebo recipients after natural infection (9.8 log 2 versus 6.6 log 2, or 1:891 versus 1:97, P=0.046; FIG. 5). One of the six vaccinees (subject F5 35, supplementary tables) did not shed vaccine virus and did not have a rise in antibody titer after vaccination, suggesting that he did not have a vaccine "take" and experienced a primary immune response to infection with wild-type RSV. The post-surveillance geometric mean PRNT among the remaining five vaccinees with an initial vaccine take was 10.3 log 2 or 1:1261. Three of these five children achieved post-surveillance serum neutralizing antibody titers of >1:1000, indicating that potent anamnestic responses occurred after wild-type RSV infection in vaccine-primed individuals (FIG. 5).

These data suggest that a number of vaccine recipients had clinically inapparent wild-type RSV infections during the surveillance period that boosted the RSV PRNT greater than nine fold (on average) over the titers achieved after immunization. For vaccine recipients without a significant rise in PRNT, the mean reciprocal log 2 titer was 6.5 (1:91) after immunization and 6.3 (1:79) after the surveillance period, indicating that a neutralizing antibody response was sustained for at least 5 to 12 months after immunization.

TABLE 1

Replication of vaccine virus and clinical assessments in adults, RSV-seropositive children, and RSV-seronegative children. NT, not tested.

| Subjects | Dose (log$_{10}$ PFU/ml) | No. of subjects | % infected | % shedding virus† | Peak titer mean (SD) log$_{10}$ PFU/ml | Peak copy number log$_{10}$ (SD) | Fever | URI | LRI | Cough | OM | Respiratory or febrile illness | Other |
|---|---|---|---|---|---|---|---|---|---|---|---|---|---|
| Adults | | | | | | | | | | | | | |
| Vaccinees | 6.0 | 15 | 0 | 0 | 0.6 (0.0) | NT | 0 | 20 | 0 | 7 | 0 | 20 | 27 |
| Seropositive children | | | | | | | | | | | | | |
| Vaccinees | 6.0 | 10 | 10 | 0 | 0.6 (0.0) | NT | 0 | 40 | 0 | 0 | 0 | 40 | 20 |
| Placebo recipients | Placebo | 5 | 20 | 0 | 0.6 (0.0) | NT | 0 | 0 | 0 | 0 | 0 | 0 | 60 |

TABLE 1-continued

Replication of vaccine virus and clinical assessments in adults, RSV-seropositive children, and RSV-seronegative children. NT, not tested.

| Subjects | Dose ($\log_{10}$ PFU/ml) | No. of subjects | % infected | % shedding virus[†] | Viral detection (culture) Peak titer mean (SD) $\log_{10}$ PFU/ml | Viral detection (qPCR) Peak copy number $\log_{10}$ (SD) | Fever | URI | LRI | Cough | OM | Respiratory or febrile illness | Other |
|---|---|---|---|---|---|---|---|---|---|---|---|---|---|
| Seronegative children | | | | | | | | | | | | | |
| Vaccinees | 5.0 | 20 | 95 | 85 | 1.5 (0.9) | 3.4 (0.9) | 20 | 85 | 0 | 35 | 5 | 85 | 45 |
| Infected placebo recipient[‡] | Placebo | 1 | 100 | 100 | 2.0 (0.0) | 3.3 (0.0) | 100 | 100 | 0 | 0 | 0 | 100 | 0 |
| Placebo recipients | Placebo | 9 | 0 | 0 | 0.6 (0.0) | 1.7 (0.0) | 22 | 44 | 0 | 33 | 0 | 67 | 78 |

*Illness abbreviations and definitions are as described in the text. URI was defined as rhinorrhea, pharyngitis, or hoarseness, and LRI was defined as wheezing, rhonchi, or rales, or having been diagnosed with pneumonia or laryngotracheobronchitis (croup).
[†]% Shedding vaccine virus as detected by culture and/or rPT-qPCR. The limit of detection of vaccine virus was 0.6 $\log_{10}$ PFU/ml by culture, and 1.7 $\log_{10}$ copy numbers/ml by rRT-qPCR.
[‡]Data from the seronegative placebo recipient, as described in the text.

TABLE 2

Replication of vaccine virus and antibody responses in adults, RSV-seropositive children, and RSV-seronegative children. ELISA, enzyme-linked immunosorbent assay.

| Subjects | Dose ($\log_{10}$ PFU/ml) | No. of subjects | % infected | % Shedding virus[†] | Serum RSV neutralizing antibody* [mean(SD)] Pre (SD) | Post (SD) | ≥4-Fold rise (%) | Serum IgG ELISA RSV F* [mean (SD)] Pre (SD) | Post (SD) | ≥4-Fold rise (%) |
|---|---|---|---|---|---|---|---|---|---|---|
| Adults | | | | | | | | | | |
| Vaccinees | 6.0 | 15 | 0 | 0 | 9.3 (1.1) | 9.6 (0.9) | 0 | 15.1 (1.2) | 15.0 (1.2) | 0 |
| Seropositive children | | | | | | | | | | |
| Vaccinees | 6.0 | 10 | 10 | 0 | 7.5 (1.9) | 7.7 (1.8) | 0 | 14.2 (2.3) | 14.0 (2.1) | 10 |
| Placebo recipients | Placebo | 5 | 20 | 0 | 8.4 (2.7) | 9.0 (2.9) | 20 | 14.8 (1.1) | 15.6 (1.4) | 20 |
| Seronegative children | | | | | | | | | | |
| Vaccinees | 5.0 | 20 | 95 | 85 | 2.7 (0.9) | 6.6 (1.1) | 95 | 7.1 (2.7) | 13.6 (1.6) | 90 |
| Infected placebo recipient[‡] | Placebo | 1 | 100 | 100 | 2.3 (0.0) | 7.6 (0.0) | 100 | 5.6 (0.0) | 13.6 (0.0) | 100 |
| Placebo recipients | Placebo | 9 | 0 | 0 | 2.3 (0.0) | 2.3 (0.0) | 0 | 5.4 (1.5) | 5.1 (1.0) | 0 |

*Antibody data are expressed as reciprocal mean $\log_2$ titers.
[†]% Shedding vaccine virus as detected by culture and/or rRT-qPCR. The limit of detection of vaccine virus was 0.6 $\log_{10}$ PFU/ml.
[‡]Data from the seronegative placebo recipient, as described in the text.

SUPPLEMENTAL TABLE 1

Clinical responses and viral shedding in seropositive children 12 months to 59 months of age to $10^{6.0}$ PFU of live recombinant respiratory syncytial virus vaccine RSV MEDI ΔM2-2 or placebo

| Date of inoculation | Subject No. | Age/months | Inf | Virus shedding (culture) peak $\log_{10}$ titer/mL | Adventitious agents (days) | Fever | URI | LRI | Cough | OM | Respiratory or febrile | illness | Other |
|---|---|---|---|---|---|---|---|---|---|---|---|---|---|
| Vaccinees | | | | | | | | | | | | | |
| Nov. 11, 2011 | 17 | 39 | 0 | 0.6 | neg(0) | 0 | 0 | 0 | 0 | 0 | | 0 | 0 |
| Dec. 2, 2011 | 18 | 41 | 0 | 0.6 | neg(0)Rhino(10) | 0 | 0 | 0 | 0 | 0 | | 0 | NC(10-13)[1] |
| Dec. 2, 2011 | 19 | 37 | 0 | 0.6 | neg(0, 10) | 0 | 0 | 0 | 0 | 0 | | 0 | 0 |
| Feb. 23, 2012 | 21 | 44 | 0 | 0.6 | neg(0)Adeno(8)Rhino(8, 11) | 0 | R(8-12)[1] | 0 | 0 | 0 | | 1 | 0 |
| Mar. 9, 2012 | 22 | 39 | 0 | 0.6 | Rhino(0)neg(5)Entero(6-7) | 0 | R(1-6)[1] | 0 | 0 | 0 | | 1 | 0 |
| Mar. 9, 2012 | 23 | 18 | 0 | 0.6 | neg(0, 4, 7)Rhino(3) | 0 | R(3-7)[1] | 0 | 0 | 0 | | 1 | Epistaxis(5)[1] |

SUPPLEMENTAL TABLE 1-continued

Clinical responses and viral shedding in seropositive children 12 months to 59 months of age to $10^{6.0}$ PFU of live recombinant respiratory syncytial virus vaccine RSV MEDI ΔM2-2 or placebo

| Date of inoculation | Subject No. | Age/ months | Inf | Virus shedding (culture) peak $\log_{10}$ titer/mL | Adventitious agents (days) | Illness (days) | | | | | | | |
|---|---|---|---|---|---|---|---|---|---|---|---|---|---|
| | | | | | | Fever | URI | LRI | Cough | OM | Respiratory or febrile | illness | Other |
| Mar. 30, 2012 | 26 | 31 | 0 | 0.6 | 0 | 0 | 0 | 0 | 0 | 0 | 0 | 0 | 0 |
| Mar. 30, 2012 | 27 | 44 | 0 | 0.6 | 0 | 0 | 0 | 0 | 0 | 0 | 0 | 0 | 0 |
| Apr. 5, 2012 | 28 | 31 | 0 | 0.6 | neg(0)Rhino (11) | 0 | R(9-16)[1] | 0 | 0 | 0 | 0 | 1 | 0 |
| Apr. 13, 2012 | 29 | 57 | 0 | 0.6 | 0 | 0 | 0 | 0 | 0 | 0 | 0 | 0 | 0 |
| | Mean | 38.1 | 0/10 | 0.6 | | 0/10 | 4/10 | 0/10 | 0/10 | 0/10 | | 4/10 | 2/10 |
| | SD | 10.2 | | 0.0 | | | | | | | | | |
| | % | | 0 | | | 0 | 40 | 0 | 0 | 0 | | 40 | 20 |
| Placebo recipients | | | | | | | | | | | | | |
| Nov. 11, 2011 | 16 | 21 | 0 | 0.6 | Rhino(0) | 0 | 0 | 0 | 0 | 0 | | 0 | Skin Excoriation(3-10)[1] |
| Dec. 16, 2011 | 20 | 59 | 0 | 0.6 | 0 | 0 | 0 | 0 | 0 | 0 | | 0 | Epistaxis(4)[1] |
| Mar. 23, 2012 | 24 | 27 | 1 | 0.6 | 0 | 0 | 0 | 0 | 0 | 0 | | 0 | 0 |
| Mar. 29, 2012 | 25 | 39 | 0 | 0.6 | 0 | 0 | 0 | 0 | 0 | 0 | | 0 | 0 |
| Apr. 20, 2012 | 30 | 27 | 0 | 0.6 | 0 | 0 | 0 | 0 | 0 | 0 | | 0 | Abd Discomfort(3)[1] |
| | Mean | 34.6 | 1/5 | 0.6 | | 0/5 | 0/5 | 0/5 | 0/5 | 0/5 | | 0/5 | 3/5 |
| | SD | 15.1 | | 0.0 | | | | | | | | | |
| | % | | 20 | | | 0 | 0 | 0 | 0 | 0 | | 0 | 60 |

URI = upper respiratory illness, LRI = lower respiratory illness, OM = otitis media, R = rhinorrhea, NC = nasal congestion, Adeno = adenovirus, Rhino = rhinovirus, Entero = enterovirus, Inf = infected with vaccine virus as determined by shedding of vaccine virus and/or ≥4-fold increase in antibody titers. Parentheses indicate study days on which the event occurred. Superscripted numbers next to the sign or symptom indicate severity grade as described in the text and figure legends. Shedding of vaccine virus was detected by culture (limit of detection = 0.7 log10/mL; culture negative expressed as 0.6 log10/mL). Adventitious agents were detected by multiplex RT-PCR.

SUPPLEMENTAL TABLE 2

Antibody responses of seropositive children 12 to 59 months of age to $10^{6.0}$ PFU of live recombinant respiratory syncytial virus vaccine RSV MEDI ΔM2-2 or placebo

| Date of inoculation | Subject No. | Age/ months | Serum Antibody Responses | | | | | |
|---|---|---|---|---|---|---|---|---|
| | | | RSV Neutralizing Antibody ($1/\log_2$) | | | IgG ELISA RSV F ($1/\log_2$) | | |
| | | | Pre | Post | ≥4 Fold Rise | Pre | Post | ≥4 Fold Rise |
| Vaccinees | | | | | | | | |
| Nov. 11, 2011 | 17 | 39 | 7.8 | 7.4 | 0 | 13.6 | 13.6 | 0 |
| Dec. 2, 2011 | 18 | 41 | 7.5 | 8.4 | 0 | 15.6 | 15.6 | 0 |
| Dec. 2, 2011 | 19 | 37 | 5.6 | 5.9 | 0 | 11.6 | 13.6 | 1 |
| Feb. 23, 2012 | 21 | 44 | 8.2 | 7.5 | 0 | 15.6 | 15.6 | 0 |
| Mar. 9, 2012 | 22 | 39 | 5.7 | 5.9 | 0 | 13.6 | 11.6 | 0 |
| Mar. 9, 2012 | 23 | 18 | 5.2 | 5.0 | 0 | 9.6 | 9.6 | 0 |
| Mar. 30, 2012 | 26 | 31 | 9.9 | 9.1 | 0 | 15.6 | 15.6 | 0 |
| Mar. 30, 2012 | 27 | 44 | 7.2 | 8.1 | 0 | 15.6 | 15.6 | 0 |
| Apr. 5, 2012 | 28 | 31 | 11.3 | 11.2 | 0 | 17.6 | 15.6 | 0 |
| Apr. 13, 2012 | 29 | 57 | 7.0 | 8.2 | 0 | 13.6 | 13.6 | 0 |
| | Mean | 38.1 | 7.5 | 7.7 | 0/0 | 14.2 | 14.0 | 1/10 |
| | SD | 10.2 | 1.9 | 1.8 | | 2.3 | 2.1 | |
| | % | | | | 0 | | | 10 |
| Placebo recipients | | | | | | | | |
| Nov. 11, 2011 | 16 | 21 | 7.8 | 6.9 | 0 | 15.6 | 15.6 | 0 |
| Dec. 16, 2011 | 20 | 59 | 6.3 | 6.2 | 0 | 13.6 | 13.6 | 0 |
| Mar. 23, 2012 | 24 | 27 | 7.2 | 12.8 | 1 | 13.6 | 17.6 | 1 |
| Mar. 29, 2012 | 25 | 39 | 7.5 | 7.8 | 0 | 15.6 | 15.6 | 0 |
| Apr. 20, 2012 | 30 | 27 | 13.0 | 11.3 | 0 | 15.6 | 15.6 | 0 |
| | Mean | 34.6 | 8.4 | 9.0 | 1/5 | 14.8 | 15.6 | 1/5 |
| | SD | 15.1 | 2.7 | 2.9 | | 1.1 | 1.4 | |
| | % | | | | 20 | | | 20 |

SUPPLEMENTAL TABLE 3

Clinical responses of seronegative children 6 months to 24 months of age to $10^{5.0}$ PFU of live recombinant respiratory syncytial virus vaccine RSV MEDI ΔM2-2 or placebo

| Date of inoculation | Subject No. | Age/ months | Inf | Fever | URI | LRI | Cough | OM | Respiratory or febrile illness | Other |
|---|---|---|---|---|---|---|---|---|---|---|
| Vaccinees | | | | | | | | | | |
| May 11, 2012 | 32 | 12 | 1 | 100.1 (9)[0a] | R(3-15)[1] | 0 | 0 | 0 | 1 | 0 |
| May 18, 2012 | 33 | 7 | 1 | 102.5 (24-25)[3] | R(7-10)[1] | 0 | 0 | 0 | 1 | 0 |
| May 18, 2012 | 34 | 13 | 1 | 104.6 (23-26)[3] | R(7-12)[1] | 0 | 0 | 0 | 1 | NC(7-10)[1], diaperrash(21-24)[2] |
| May 25, 2012 | 35 | 13 | 0 | 0 | 0 | 0 | 0 | 0 | 0 | 0 |
| Jul. 6, 2012 | 37 | 13 | 1 | 0 | R(24-36)[1] | 0 | 0 | 0 | 1 | 0 |
| Jul. 13, 2012 | 38 | 22 | 1 | 0 | R(4-15)[1] | 0 | (3-10)[1] | (4-15)[2] | 1 | NC(1-2)[1], ear bruise(22-26)[1] |
| Aug. 10, 2012 | 41 | 14 | 1 | 0 | R(4-13)[1] | 0 | 0 | 0 | 1 | emesis(5)[1], NC(8-14)[1] |
| Aug. 31, 2012 | 42 | 11 | 1 | 0 | R(7-13)[1] | 0 | (7-9)[1] | 0 | 1 | diarrhea(0-1)[1], diaper rash(2)[2] |
| Sep. 14, 2012 | 44 | 13 | 1 | 0 | R(4-10)[1] | 0 | 0 | 0 | 1 | NC(11-12)[1], emesis(20)[1], diarrhea(22-23)[1] |
| Jun. 28, 2013 | 45 | 15 | 1 | 0 | 0 | 0 | 0 | 0 | 0 | 0 |
| May 30, 2013 | 46 | 18 | 1 | 0 | R(5-11)[1] | 0 | (9-10)[1] | 0 | 1 | 0 |
| Aug. 2, 2013 | 48 | 13 | 1 | 0 | R(8-11)[1] | 0 | 0 | 0 | 1 | Kawasaki Syndrome (32-47)[3]; hospitalization (35-38) |
| Aug. 23, 2013 | 50 | 12 | 1 | 0 | 0 | 0 | 0 | 0 | 0 | 0 |
| Sep. 13, 2013 | 51 | 8 | 1 | 100.8(10)[1] | R(8-11)[1] | 0 | (26-32)[1] | 0 | 1 | insomnia(15)[1] |
| Sep. 20, 2013 | 52 | 10 | 1 | 0 | R(6-10)[1] | 0 | 0 | 0 | 1 | 0 |
| Sep. 20, 2013 | 54 | 13 | 1 | 0 | R(8 -12)[1] | 0 | 0 | 0 | 1 | 0 |
| Oct. 24, 2013 | 55 | 20 | 1 | 0 | R(6-7, 9-21)[1] | 0 | (9-10, 16-17)[1] | 0 | 1 | 0 |
| Oct. 25, 2013 | 56 | 24 | 1 | 0 | R(4-11, 20-28)[1] | 0 | 0 | 0 | 1 | malaise(22)[1] |
| Oct. 12, 2012 | 59 | 14 | 1 | 0 | R(6-10)[1] | 0 | 0 | 0 | 1 | 0 |
| Aug. 31, 2012 | 60 | 9 | 1 | 0 | R(4-14, 22-29)[1] | 0 | (4-5)[1] | 0 | 1 | NC(6-14)[1] |
| Mean | | 13.7 | 19/20 | 4/20 | 17/20 | 0/20 | 7/20 | 1/20 | 17/20 | 9/20 |
| SD | | 4.4 | | | | | | | | |
| % | | | 95 | 20 | 85 | 0 | 35 | 5 | 85 | 45 |
| Placebo recipients | | | | | | | | | | |
| May 11, 2012 | 31 | 6 | 0 | 0 | R(1-17)[1] | 0 | 0 | 0 | 1 | 0 |
| Jun. 1, 2012 | 36 | 14 | 0 | 102.2 (27-28)[2] | 0 | 0 | 0 | 0 | 1 | 0 |
| Jul. 25, 2012 | 39 | 12 | 0 | 101.7(7-8)[2] | R(6-12)[1] | 0 | (5-12, 18-21)[1] | 0 | 1 | swollen eyelid(12)[1] |
| Aug. 3, 2012 | 40 | 9 | 0 | 0 | 0 | 0 | (8-9, 13-14)[1] | 0 | 1 | NC(14)[1] |
| Sep. 7, 2012 | 43 | 14 | 0 | 0 | R(4-13)[1] | 0 | 0 | 0 | 1 | finger burn(7)[1], NC(14-19)[1] |
| Aug. 16, 2013 | 49 | 7 | 0 | 0 | 0 | 0 | 0 | 0 | 0 | malaise(11)[1] |
| Sep. 20, 2013 | 53 | 14 | 0 | 0 | 0 | 0 | 0 | 0 | 0 | head bump(4)[1] |
| Oct. 31, 2013 | 57 | 19 | 0 | 0 | R(1-2, 4-6)[1] | 0 | (1-2, 22-26)[1] | 0 | 1 | chest congestion(21-25)[1], malaise(0, 2, 7, 24-25)[1] |
| Apr. 5, 2013 | 58 | 12 | 0 | 0 | 0 | 0 | 0 | 0 | 0 | insomnia(10)[1] |
| Mean | | 11.9 | 1/10 | 2/9 | 4/9 | 0/9 | 3/9 | 0/9 | 6/9 | 7/9 |
| SD | | 4.0 | | | | | | | | |
| % | | | 10 | 22 | 44 | 0 | 33 | 0 | 67 | 70 |
| Placebo recipient infected with vaccine virus | | | | | | | | | | |
| Aug. 2, 2013 | 275.47 | 13 | 1 | 100.6(17)[1] | R(8-9)[1] | 0 | 0 | 0 | 1 | 0 |

URI = upper respiratory illness, LRI = lower respiratory illness, OM = otitis media, R = rhinorrhea, NC = nasal congestion, Inf = infected with vaccine virus as determined by shedding of vaccine virus and/or ≥4-fold increase in antibody titers. Parentheses indicate study days on which the event occured. Superscripted numbers next to the sign or symptom indicate severity grade as described in the text and figure legends.

SUPPLEMENTAL TABLE 4

Viral shedding in seronegative children 6 to 24 months of age who received $10^{5.0}$ PFU of live recombinant respiratory syncytial virus vaccine RSV MEDI ΔM2-2 or placebo

| Dates of inoculation | Subject No. | Age/ months | Inf | Viral Detection (culture) Virus Detected by Culture | Peak Titer $log_{10}$ | Viral Detection (RT-qPCR) Virus Detected by PCR | Peak Copy Number $log_{10}$ | Adventitious agents(days) |
|---|---|---|---|---|---|---|---|---|
| Vaccinees | | | | | | | | |
| May 11, 2012 | 32 | 12 | 1 | 1 | 3.8 | 1 | 4.5 | neg(0), RSV(3, 5, 6, 10), parecho(5), Cor43(6, 10, 11) |
| May 18, 2012 | 33 | 7 | 1 | 1 | 1 | 1 | 1.8 | neg(0, 24, 25, 27), RSV(11), rhino(6) |
| May 18, 2012 | 34 | 13 | 1 | 1 | 1.3 | 1 | 3 | neg(0, 11, 24, 25, 27) |
| May 25, 2012 | 35 | 13 | 0 | 0 | 0.6 | 0 | 1.7 | 0 |
| Jul. 6, 2012 | 37 | 13 | 1 | 0 | 0.6 | 0 | 1.7 | neg(0, 26), rhino(28) |
| Jul. 13, 2012 | 38 | 22 | 1 | 1 | 0.8 | 1 | 3.2 | neg(0), RSV(3, 5, 7, 10), boca(5) |
| Aug. 10, 2012 | 41 | 14 | 1 | 0 | 0.6 | 1 | 3.3 | neg(0), RSV(5, 7, 10, 14) |
| Aug. 31, 2012 | 42 | 11 | 1 | 0 | 0.6 | 1 | 3.1 | neg(0), RSV(10, 12) |
| Sep. 14, 2012 | 44 | 13 | 1 | 1 | 1.5 | 1 | 2.8 | neg(0), RSV(5, 7, 10), rhino(10) |
| Jun. 28, 2013 | 45 | 15 | 1 | 1 | 1.2 | 1 | 4.1 | 0 |
| May 30, 2013 | 46 | 18 | 1 | 1 | 1.5 | 1 | 3.9 | adeno(0, 11), RSV(6, 8) |
| Aug. 2, 2013 | 48 | 13 | 1 | 1 | 2 | 1 | 4.5 | neg(0), RSV(7, 10) |
| Aug. 23, 2013 | 50 | 12 | 1 | 0 | 0.6 | 0 | 1.7 | 0 |
| Sep. 13, 2013 | 51 | 8 | 1 | 1 | 1.3 | 1 | 3.2 | neg(0), RSV(10), rhino(10, 12, 14, 19, 27), parecho(19, 27) |
| Sep. 20, 2013 | 52 | 10 | 1 | 0 | 0.6 | 1 | 3.1 | Cor43, parecho(0), RSV(7, 10) |
| Sep. 20, 2013 | 54 | 13 | 1 | 1 | 1.7 | 1 | 3.9 | neg(0), RSV(10, 12) |
| Oct. 24, 2013 | 55 | 20 | 1 | 0 | 0.6 | 1 | 4 | neg(0, 11, 12, 14, 20, 21), RSV(7), boca(18), adeno(18) |
| Oct. 25, 2013 | 56 | 24 | 1 | 0 | 0.6 | 1 | 2.9 | neg(0, 12, 28), RSV(5, 7, 10), rhino(21) |
| Oct. 12, 2012 | 59 | 14 | 1 | 1 | 3.4 | 1 | 4 | 0 |
| Aug. 31, 2012 | 60 | 9 | 1 | 1 | 4 | 1 | 5.3 | parecho (11, 12), rhino (25, 28) |
| Mean | | 13.7 | 19/20 | 12/20 | 1.5 | 17/20 | 3.4 | |
| SD | | 4.4 | | | 0.9 | | 0.9 | |
| % | | | 95 | 60 | | 85 | | |
| Placebo recipients | | | | | | | | |
| May 11, 2012 | 31 | 6 | | 0 | 0.6 | 0 | 1.7 | rhino(0, 3, 18), neg(10) |
| Jun. 1, 2012 | 36 | 14 | | 0 | 0.6 | 0 | 1.7 | neg(0, 27-28) |
| Jul. 25, 2012 | 39 | 12 | | 0 | 0.6 | 0 | 1.7 | neg (0, 7, 8, 21), rhino (9,12) |
| Aug. 3, 2012 | 40 | 9 | | 0 | 0.6 | 0 | 1.7 | boca(0), neg(10, 12, 14, 17), rhino(27, 28) |
| Sep. 7, 2012 | 43 | 14 | | 0 | 0.6 | 0 | 1.7 | neg(0, 7), entero(5, 10, 14) |
| Aug. 16, 2013 | 49 | 7 | | 0 | 0.6 | 0 | 1.7 | 0 |
| Sep. 20, 2013 | 53 | 14 | | 0 | 0.6 | 0 | 1.7 | 0 |
| Oct. 31, 2013 | 57 | 19 | | 0 | 0.6 | 0 | 1.7 | Para-1(0, 3), neg(5, 7, 27), Para-4(21) |
| Apr. 5, 2013 | 58 | 12 | | 0 | 0.6 | 0 | 1.7 | 0 |
| Mean | | 11.9 | | 0/9 | 0.6 | 0/9 | 1.7 | |
| SD | | 4.0 | | | 0.0 | | 0.0 | |
| % | | | | | 0 | | 0 | |
| Placebo recipient infected with vaccine virus | | | | | | | | |
| Aug. 2, 2013 | 47 | 13 | 1 | 2 | 1 | 3.3 | neg(0, 7, 10), RSV(17) | |

Adeno = adenovirus, Rhino = rhinovirus, Entero = enterovirus, Inf = infected with vaccine virus as determined by shedding of vaccine virus and/or ≥4-fold increase in antibody titers. Parentheses indicate study days on which the event occurred. Shedding of vaccine virus was detected by culture (limit of detection = 0.7 log10/mL; culture negative expressed as 0.6 log10/mL) and by RT-qPCR (limit of detection = 1.7 log10 copies/mL; PCR negative expressed as 1.7 log10 copies/mL). Adventitious agents were detected by multiplex RT-PCR.

SUPPLEMENTAL TABLE 5

Antibody responses of seronegative children 6 to 24 months of age of $10^{5.0}$ PFU of live recombinant respiratory syncytial virus vaccine RSV MEDI ΔM2-2 or placebo

| Date of Inoculation | Subject No. | Age/ months | Viral Shedding Culture + or PCR+ | Serum Antibody Responses RSV Neutralizing Antibody (1/llog 2) Pre | Post | ≥4 Fold Rise | IgG ELISA RSV F (1/log2) Pre | Post | ≥4 Fold Rise |
|---|---|---|---|---|---|---|---|---|---|
| Vaccines | | | | | | | | | |
| May 11, 2012 | 32 | 12 | 1 | 2.3 | 7.3 | 1 | 4.6 | 13.6 | 1 |
| May 18, 2012 | 33 | 7 | 1 | 3.5 | 6.5 | 1 | 7.6 | 13.6 | 1 |
| May 18, 2012 | 34 | 13 | 1 | 2.3 | 6.2 | 1 | 5.6 | 15.6 | 1 |

SUPPLEMENTAL TABLE 5-continued

Antibody responses of seronegative children 6 to 24 months of age of $10^{5.0}$ PFU of live recombinant respiratory syncytial virus vaccine RSV MEDI ΔM2-2 or placebo

| Date of Inoculation | Subject No. | Age/ months | Viral Shedding Culture + or PCR+ | Serum Antibody Responses RSV Neutralizing Antibody (1/llog 2) | | | IgG ELISA RSV F (1/log2) | | |
|---|---|---|---|---|---|---|---|---|---|
| | | | | Pre | Post | ≥4 Fold Rise | Pre | Post | ≥4 Fold Rise |
| May 25, 2012 | 35 | 13 | 0 | 4.5 | 4.0 | 0 | 11.6 | 11.6 | 0 |
| Jul. 6, 2012 | 37 | 13 | 0 | 2.3 | 6.1 | 1 | 9.6 | 11.6 | 1 |
| Jul. 13, 2012 | 38 | 22 | 1 | 2.3 | 6.4 | 1 | 4.6 | 13.6 | 1 |
| Aug. 10, 2012 | 41 | 14 | 1 | 2.3 | 7.1 | 1 | 4.6 | 15.6 | 1 |
| Aug. 31, 2012 | 42 | 11 | 1 | 2.3 | 6.0 | 1 | 9.6 | 13.6 | 1 |
| Sep. 14, 2012 | 44 | 13 | 1 | 2.3 | 5.9 | 1 | 4.6 | 11.6 | 1 |
| Jun. 28, 2013 | 45 | 15 | 1 | 2.3 | 6.6 | 1 | 4.6 | 13.6 | 1 |
| May 30, 2013 | 46 | 18 | 1 | 2.3 | 6.4 | 1 | 5.6 | 13.6 | 1 |
| Aug. 2, 2013 | 48 | 13 | 1 | 2.3 | 8.5 | 1 | 4.6 | 15.6 | 1 |
| Aug. 23, 2013 | 50 | 12 | 0 | 2.3 | 6.9 | 1 | 9.6 | 13.6 | 1 |
| Sep. 13, 2013 | 51 | 8 | 1 | 2.3 | 5.8 | 1 | 7.6 | 13.6 | 1 |
| Sep. 20, 2013 | 52 | 10 | 1 | 2.3 | 6.6 | 1 | 5.6 | 13.6 | 1 |
| Sep. 20, 2013 | 54 | 13 | 1 | 2.3 | 6.0 | 1 | 4.6 | 13.6 | 1 |
| Oct. 24, 2013 | 55 | 20 | 1 | 5.0 | 8.7 | 1 | 11.6 | 15.6 | 1 |
| Oct. 25, 2013 | 56 | 24 | 1 | 2.3 | 6.2 | 1 | 4.6 | 15.6 | 1 |
| Oct. 12, 2012 | 59 | 14 | 1 | 4.2 | 8.4 | 1 | 11.6 | 13.6 | 1 |
| Aug. 3, 2012 | 60 | 9 | 1 | 2.3 | 6.2 | 1 | 9.6 | 9.6 | 0 |
| | Mean | 13.7 | 17/20 | 2.7 | 6.6 | 19/20 | 7.1 | 13.6 | 18/20 |
| | SD | 4.4 | | 0.9 | 1.1 | | 2.7 | 1.6 | |
| | % | | 85 | | | 95 | | | 90 |
| Placebo recipients | | | | | | | | | |
| May 11, 2012 | 31 | 6 | 0 | 2.3 | 2.3 | 0 | 9.6 | 7.6 | 0 |
| Jun. 1, 2012 | 36 | 14 | 0 | 2.3 | 2.3 | 0 | 4.6 | 4.6 | 0 |
| Jul. 25, 2012 | 39 | 12 | 0 | 2.3 | 2.3 | 0 | 4.6 | 4.6 | 0 |
| Aug. 3, 2012 | 40 | 9 | 0 | 2.3 | 2.3 | 0 | 4.6 | 4.6 | 0 |
| Sep. 7, 2012 | 43 | 14 | 0 | 2.3 | 2.3 | 0 | 4.6 | 4.6 | 0 |
| Aug. 16, 2013 | 49 | 7 | 0 | 2.3 | 2.3 | 0 | 5.6 | 5.6 | 0 |
| Sep. 20, 2013 | 53 | 14 | 0 | 2.3 | 2.3 | 0 | 4.6 | 4.6 | 0 |
| Oct. 31, 2013 | 57 | 19 | 0 | 2.3 | 2.3 | 0 | 4.6 | 4.6 | 0 |
| Apr. 5, 2013 | 58 | 12 | 0 | 2.3 | 2.3 | 0 | 5.6 | 4.6 | 0 |
| | Mean | 11.9 | 0/9 | 2.3 | 2.3 | 0/9 | 5.4 | 5.1 | 0/9 |
| | SD | 4.0 | | 0.0 | 0.0 | | 1.6 | 1.0 | |
| | % | | 0 | | | 0 | | | 0 |
| Placebo recipient infected with vaccine virus | | | | | | | | | |
| Aug. 2, 2013 | 47 | 13 | 1 | 2.3 | 7.6 | 1 | 5.6 | 13.6 | 1 |

SUPPLEMENTAL TABLE 6

RSV neutralizing antibody titers in sera obtained before and after the RSV surveillance period in RSV seronegative children 6 to 24 months of age who had received RSV MEDI ΔM2-2 vaccine or placebo

| Vaccinee Subject# | PRE-VAC | POST-VAC | PRE-SURV | POST-SURV | PRE-VAC | POST-VAC | PRE-SURV | POST-SURV |
|---|---|---|---|---|---|---|---|---|
| | RSV Neut Ab Reciprocal Titer | | | | RSV Neut Ab Titer expressed as 1/log₂ | | | |
| 32 | 5 | 109 | 59 | 158 | 2.3 | 6.8 | 5.9 | 7.3 |
| 33 | 5 | 47 | 36 | 1550 | 2.3 | 5.6 | 5.2 | 10.6 |
| 34 | 11 | 59 | 24 | 29 | 3.5 | 5.9 | 4.6 | 4.9 |
| 35 | 27 | 24 | 22 | 135 | 4.8 | 4.6 | 4.5 | 7.1 |
| 37 | 5 | 65 | 45 | 17 | 2.3 | 6.0 | 5.5 | 4.1 |
| 38 | 5 | 77 | 79 | 1443 | 2.3 | 6.3 | 6.3 | 10.5 |
| 41 | 5 | 109 | 114 | 200 | 2.3 | 6.8 | 6.8 | 7.6 |
| 42 | 5 | 82 | 71 | 70 | 2.3 | 6.4 | 6.1 | 6.1 |
| 44 | 5 | 41 | 41 | 250 | 2.3 | 5.4 | 5.4 | 8.0 |
| 45 | 5 | 177 | 123 | 110 | 2.3 | 7.5 | 6.9 | 6.8 |
| 46 | 5 | 120 | 95 | 1702 | 2.3 | 6.9 | 6.6 | 10.7 |
| 48 | 5 | 350 | 350 | 889 | 2.3 | 8.5 | 8.5 | 9.8 |
| 50 | 5 | 141 | 141 | 35 | 2.3 | 7.1 | 7.1 | 5.1 |
| 51 | 5 | 42 | 42 | 25 | 2.3 | 5.4 | 5.4 | 4.6 |
| 52 | 5 | 78 | 78 | 93 | 2.3 | 6.3 | 6.3 | 6.5 |
| 54 | 5 | 40 | 40 | 28 | 2.3 | 5.3 | 5.3 | 4.8 |
| 55 | 29 | 418 | 418 | 373 | 4.9 | 8.7 | 8.7 | 8.5 |
| 55 | 5 | 106 | 106 | 4485 | 2.3 | 6.7 | 6.7 | 12.1 |

SUPPLEMENTAL TABLE 6-continued

RSV neutralizing antibody titers in sera obtained before and after the RSV surveillance period in RSV seronegative children 6 to 24 months of age who had received RSV MEDI AM2-2 vaccine or placebo

| | | | | | | | | |
|---|---|---|---|---|---|---|---|---|
| 59 | 21 | 224 | 224 | 100 | 4.4 | 7.8 | 7.8 | 6.6 |
| 60 | 5 | 46 | 46 | 27 | 2.3 | 5.5 | 5.5 | 4.8 |

| Placebo Subject# | PRE-VAC | POST-VAC | PRE-SURV | POST-SURV | PRE-VAC | POST-VAC | PRE-SURV | POST-SURV |
|---|---|---|---|---|---|---|---|---|
| | RSV Neut Ab Reciprocal Titer | | | | RSV Neut Ab Titer expressed as 1/log$_2$ | | | |
| 31 | 10 | 5 | 5 | 5 | 3.3 | 2.3 | 2.3 | 2.3 |
| 36 | 5 | 5 | 5 | 24 | 2.3 | 2.3 | 2.3 | 4.6 |
| 39 | 5 | 5 | 5 | 5 | 2.3 | 2.3 | 2.3 | 2.3 |
| 40 | 5 | 5 | 5 | 5 | 2.3 | 2.3 | 2.3 | 2.3 |
| 43 | 5 | 5 | 5 | 289 | 2.3 | 2.3 | 2.3 | 8.2 |
| 49 | 5 | 5 | 5 | 5 | 2.3 | 2.3 | 2.3 | 2.3 |
| 53 | 5 | 5 | 5 | 5 | 2.3 | 2.3 | 2.3 | 2.3 |
| 57 | 5 | 5 | 5 | 135 | 2.3 | 2.3 | 2.3 | 7.1 |
| 58 | 5 | 5 | 5 | 5 | 2.3 | 2.3 | 2.3 | 2.3 |
| Placebo recipient infected with vaccine virus | | | | | | | | |
| \| 275.47 | 5 | 291 | N/A | 294 \| | 2.3 | 8.2 | N/A | 8.2 \| |

RSV neutralizing antibody titers were measured in serum specimens obtained prevaccination (PRE-VAC), at day 56 following vaccination (POST-VAC), within 1 month prior to the beginning of the surveillance period (PRE-SURV), and within one month following the end of the surveillance period (POST-SURV). In instances where the day 56 POST-VAC specimen was obtained within 1 month prior to the beginning of the surveillance period, an additional PRE-SURV specimen was not obtained and results from the single specimen were entered as both POST-VAC and PRE-SURV (indicated in blue).

---

What is claimed is:

1. A method of vaccinating a human subject against respiratory syncytial virus (RSV), comprising administering to the subject a composition comprising an RSV particle that comprises an RSV genome or antigenome,
   wherein the subject is less than about 24 months of age,
   wherein the composition is administered in a single dose,
   wherein the RSV genome or antigenome is the RSV genome of Genbank Accession No. M74568 except for the following modifications:
   i) a functional deletion in the M2-2 ORF corresponding to a deletion of nucleotides 8201-8434 in Genbank Accession No. M74568;
   ii) presence of G at a nucleotide position corresponding to position 1209 in Genbank Accession No. M74568 encoding an Alanine at position 24 in the N protein;
   iii) presence of G at a nucleotide position corresponding to position 779 in Genbank Accession No. M74568 encoding an Arginine at position 51 in the NS2 protein;
   iv) presence of one or more nucleotides corresponding to the nucleotides in Genbank Accession No. M74568 selected from the group consisting of: G5639 and T7481; and
   v) presence of one or more nucleotides corresponding to the nucleotides in Genbank Accession No. M74568 selected from the group consisting of: C404 in the NS1 gene, G1181 in the N gene, C6215 in the F gene, C7214 in the F gene, G7701 in the M2 gene, A8197 in the M2-2 gene, G8198 in the M2-2 gene, and A13633 in the L gene, and
   wherein the RSV genome or antigenome comprises one or more dimorphisms selected from the group consisting of: (i) A/G dimorphism at nucleotide position 285 in the NS1 gene resulting in a mixture of amino acid assignments S/G at amino acid position 63 (ii) C/T dimorphism at nucleotide position 900 in the NS2 gene; and (iii) T/G dimorphism at nucleotide position 4311 in the SH gene resulting in a mixture of amino acid assignments N/K at amino acid position 3.

2. The method of claim 1, wherein the single dose of the composition comprises about $10^{3.0}$ to about $10^{7.0}$ plaque-forming units (PFU) of RSV particles.

3. The method of claim 1, wherein the single dose of the composition comprises about $10^{5.0}$ to about $10^{6.0}$ plaque-forming units (PFU) of RSV particles.

4. The method of claim 1, wherein the single dose is administered in about 0.2 ml to about 1 ml total volume per subject.

5. The method of claim 1, wherein the single dose is administered in about 0.5 ml total volume per subject.

6. The method of claim 1, wherein the RSV particle is live attenuated.

7. The method of claim 1, wherein the subject is less than about 18 months of age.

8. The method of claim 1, wherein the route of administration is intranasal, intramuscular or subcutaneous.

9. The method of claim 1, wherein the composition is administered via nasal drops.

10. The method of claim 1, wherein the composition is administered via nasal spray.

11. The method of claim 1, wherein the composition is administered via nasal powder.

12. The method of claim 1, wherein the RSV particle exhibits restricted replication in the subject.

13. The method of claim 1, wherein the RSV particle exhibits enhanced immunogenicity in the subject.

14. The method of claim 1, wherein the subject exhibits anamnestic response to wild type RSV infection.

\* \* \* \* \*